(12) United States Patent
Beers et al.

(10) Patent No.: US 10,400,163 B2
(45) Date of Patent: Sep. 3, 2019

(54) ORGANIC ELECTROLUMINESCENT MATERIALS AND DEVICES

(71) Applicant: Universal Display Corporation, Ewing, NJ (US)

(72) Inventors: Scott Beers, Flemington, NJ (US); Chuanjun (Sean) Xia, Lawrenceville, NJ (US); Suman Layek, Lawrenceville, NJ (US); Harvey Wendt, Medford Lakes, NY (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 502 days.

(21) Appl. No.: 13/762,612

(22) Filed: Feb. 8, 2013

(65) Prior Publication Data

US 2014/0225069 A1   Aug. 14, 2014

(51) Int. Cl.
| | | |
|---|---|---|
| H01L 51/54 | (2006.01) | |
| C09K 11/06 | (2006.01) | |
| C07F 15/00 | (2006.01) | |
| H01L 51/00 | (2006.01) | |
| H01L 51/50 | (2006.01) | |

(52) U.S. Cl.
CPC .......... *C09K 11/06* (2013.01); *C07F 15/0033* (2013.01); *H01L 51/0085* (2013.01); *C09K 2211/1029* (2013.01); *C09K 2211/1044* (2013.01); *C09K 2211/185* (2013.01); *H01L 51/0054* (2013.01); *H01L 51/0074* (2013.01); *H01L 51/0081* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,484,922 A * | 1/1996 | Moore et al. | H05B 33/14 313/503 |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,916,554 B2 * | 7/2005 | Ma et al. | C07F 15/004 313/504 |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Marie R. Yamnitzky
(74) *Attorney, Agent, or Firm* — Duane Morris LLP

(57) ABSTRACT

A compound according to Formula I and devices incorporating the same are described. The compound according to Formula I can have the structure

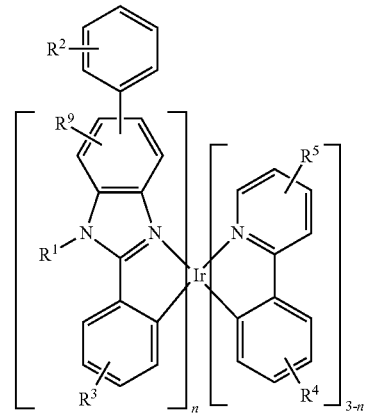

wherein $R^2$ represents mono, di, tri, tetra, penta substitutions or no substitution; $R^3$, $R^4$ and $R^5$ each represent mono, di, tri, tetra substitutions or no substitution; wherein $R^9$ represents mono, di, tri substitutions or no substitution; wherein $R^1$ is selected from the group consisting of alkyl, cycloalkyl, heteroalkyl, arylalkyl, alkoxy, aryloxy, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and $R^2$, $R^3$, $R^4$ $R^5$ and $R^9$ are each independently selected from the group consisting of all options for R1, hydrogen, deuterium, halide, amino, silyl, and combinations thereof; and wherein n is 1 or 2. The device can include the compound according to Formula I in an organic layer.

28 Claims, 3 Drawing Sheets

(56) References Cited

U.S. PATENT DOCUMENTS

| | | |
|---|---|---|
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,367,223 B2 * | 2/2013 | Xia et al. ............... 428/690 |
| 9,212,197 B2 * | 12/2015 | Kottas et al. ....... C07F 15/0033 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0141127 A1 | 6/2010 | Xia et al. |
| 2011/0227049 A1 * | 9/2011 | Xia et al. ............. C07F 15/0033 257/40 |
| 2012/0292600 A1 * | 11/2012 | Kottas et al. ................... 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0215645 | 2/2000 |
| WO | 03040257 | 5/2000 |
| WO | 0139234 | 5/2001 |
| WO | 02002714 | 1/2002 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006100298 | 9/2006 |
| WO | 20060098120 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 20111572339 A1 | 12/2011 |
| WO | 2007063754 | 2/2013 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3 (2007).

Baldo et al.,"Highly Efficient Phosphorescent Emission from Organic Electroluminescent Devices," Nature, vol. 395, 151-154, (1998).

Baldo et al.,"Very high-efficiency green organic light-emitting devices based on electrophosphorescence," Appl. Phys. Lett., vol. 75, No. 1, 4-6 (1999).

Gao, Zhiqiang et al., "Bright-Blue Electroluminescence From a Silyl-Substituted ter-(phenyiene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

(56) References Cited

OTHER PUBLICATIONS

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., "1,2,4-Triazole Derivative as an Electron Transport Layer in Organic Electroluminescent Devices," Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4'4"-Tri(N-carbazolyl)triphenylarnine (TCTA) and 4,4'4"-Tris(3-methylphenylphenyl-amino)triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,40-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al,, "Realizing Green Phosphorescent Light-Emitting Materials from Rhenium(I) Pyrazolato Dilmine Complexes," Inorg. Chem., 42(4):1248-1255 (2003).

Sakamoto, Youichi et al., "Synthesis, Characterization, and Electron-Transport Property of Perfluorinated Phenyiene Dendrimers," J. Am. Chem. Soc., 122(8):1832-1833 (2000).

Salbeck, J. et al., "Low Molecular Organic Glasses for Blue Electroluminescence," Synthetic Metals, 91:209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al:, "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al.,"A Novel Class of Phosphorescent Goid(III) Alkynyl-Based Organic Light-Emitting Devices with Tunable Colour," Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

Formula I

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as yellow/green emitters and devices, such as organic light emitting diodes, including the same as part of an organic layer.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

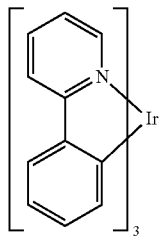

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound is provided that has the structure of Formula I shown below

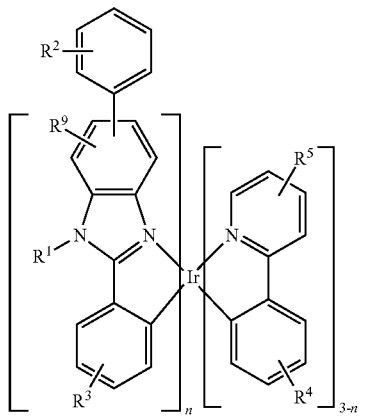

wherein $R^2$ represents mono, di, tri, tetra, penta substitutions or no substitution;

wherein $R^3$, $R^4$ and $R^5$ each represent mono, di, tri, tetra substitutions or no substitution;

wherein $R^9$ represents mono, di, tri substitutions or no substitution;

wherein $R^1$ is selected from the group consisting of alkyl, cycloalkyl, heteroalkyl, arylalkyl, alkoxy, aryloxy, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein $R^2$, $R^3$, $R^4$ $R^5$ and $R^9$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2.

According to another embodiment, a first device comprising a first organic light emitting device is also provided. The first device can include an anode, a cathode, and an organic layer, disposed between the anode and the cathode. The organic layer can include a compound of Formula I. The first device can be a consumer product, an organic light-emitting device, and/or a lighting panel.

BRIEF DESCRIPTION OF THE DRAWINGS

The present disclosure is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawings.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
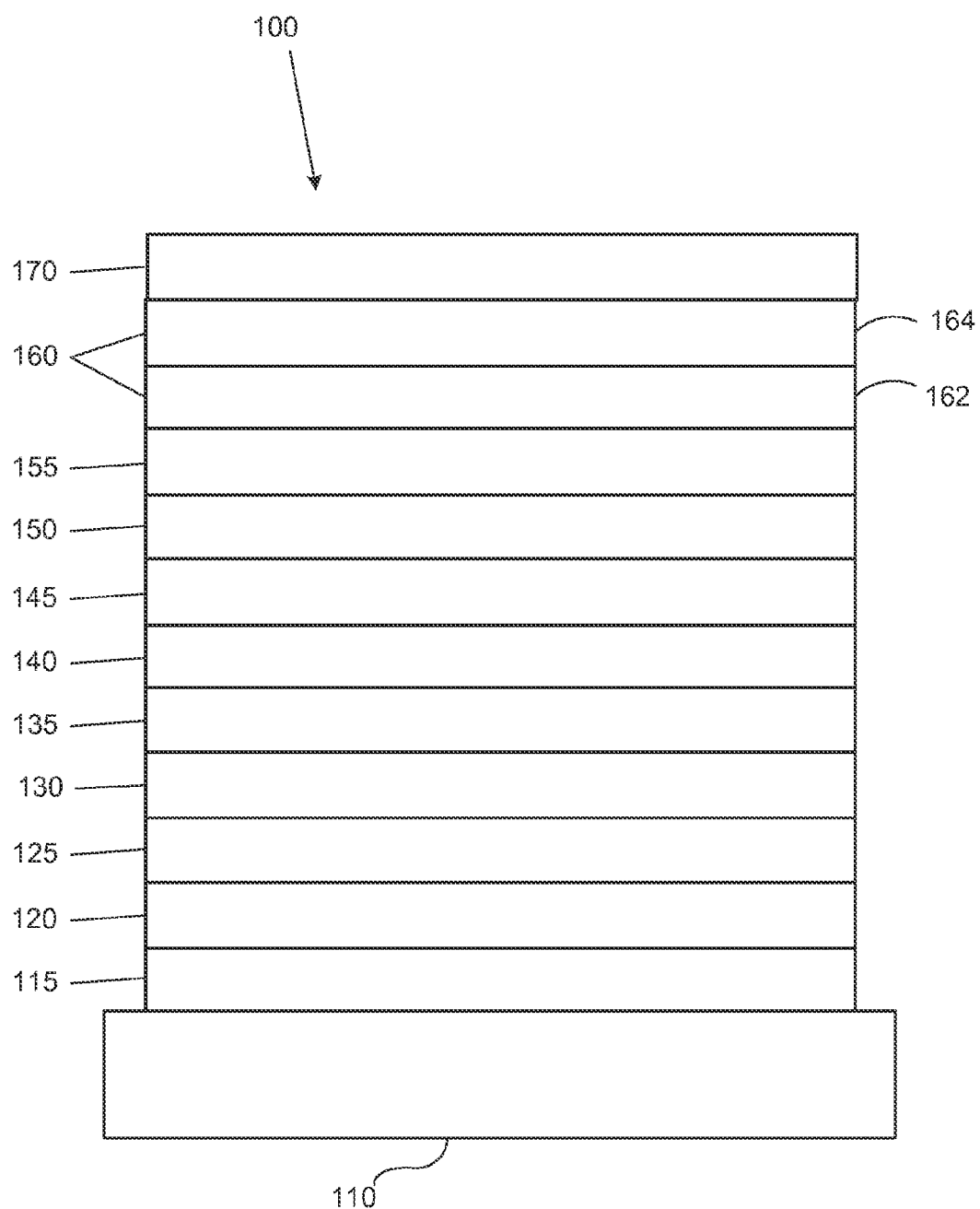
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
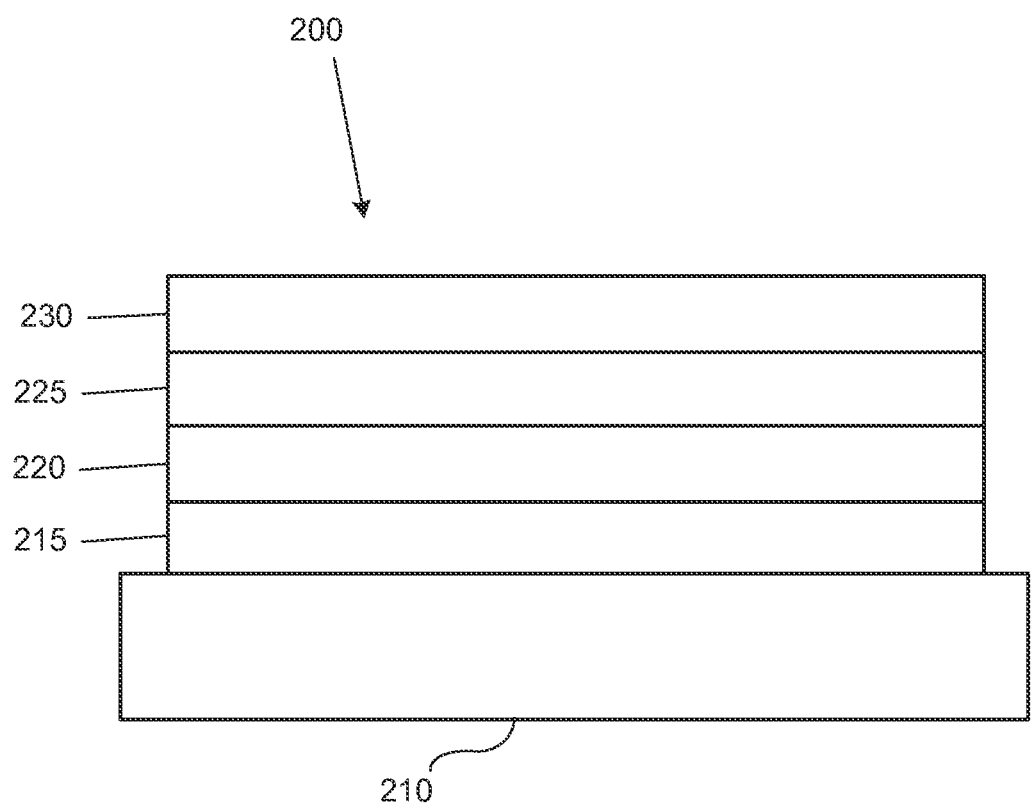
FIG. 2 shows an inverted organic light emitting device that does not have a separate electron transport layer.
Figure 3:
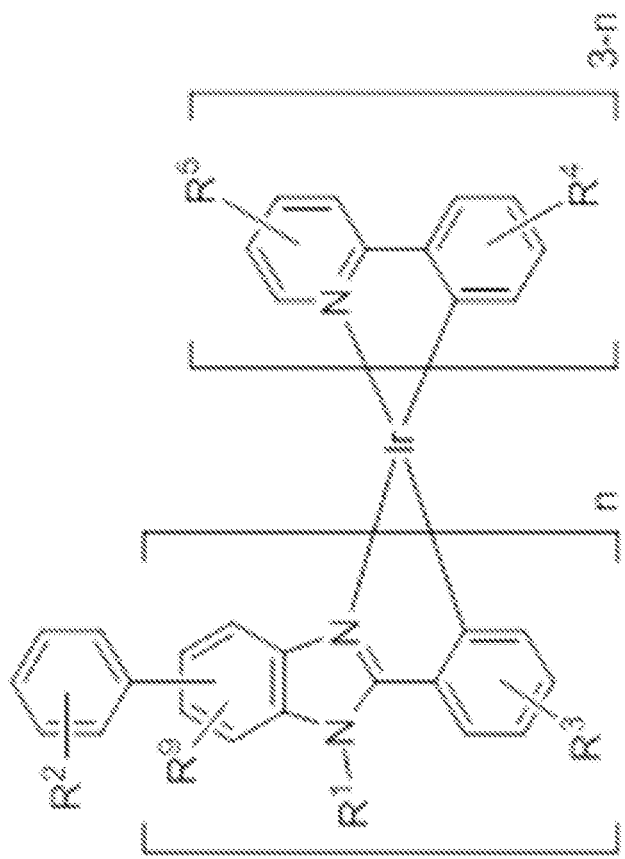
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

According to an embodiment, phenylbenzimidazole heteroleptic complexes are provided, which are unexpectedly suited as yellow and green emitters and that exhibit higher efficiency and lower driving voltages that expected when incorporated into OLED devices. In has been unexpectedly determined that attaching a pendant aromatic ring on the benzimidazole portion of Formula I, produces a new class of yellow/green phosphorescent emitters with a high efficiency and long device lifetime. This result was totally unexpected because the addition of pendant aromatic rings to either the LUMO, which is the benzimidazole portion of Formula I, or the HOMO portion of the ligand increases the conjugation, which would typically result in a significant red shift in emission.

The phenylbenzimidazole heteroleptic complexes, which may be advantageously used in OLEDs, have the structure of Formula I:

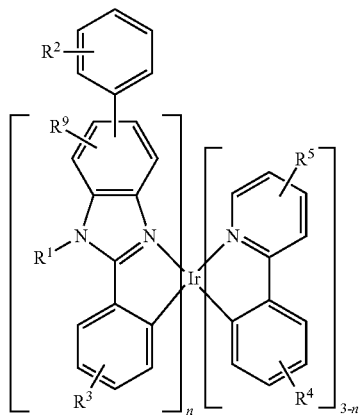

wherein $R^2$ represents mono, di, tri, tetra, penta substitutions or no substitution;

wherein $R^3$, $R^4$ and $R^5$ each represent mono, di, tri, tetra substitutions or no substitution;

wherein $R^9$ represents mono, di, tri substitutions or no substitution;

wherein $R^1$ is selected from the group consisting of alkyl, cycloalkyl, heteroalkyl, arylalkyl, alkoxy, aryloxy, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein $R^2$, $R^3$, $R^4R^5$ and $R^9$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2. In some embodiments, n=1, while n=2 in other embodiment.

The pendant aromatic ring extending from the benzimidazole portion of Formula I can be bonded in any of the four available positions of the benzene ring of the benzimidazole portion of Formula I. $R^9$ can be bonded to any remaining positions of the benzene ring of the benzimidazole portion of Formula I.

In some embodiments, the compound can be a green emitter. In some embodiments, the compound can emit in a range from 520 to 570 nm. In some embodiments, the compound can be blue shifted relative to a comparable compound without the pendant aromatic ring extending from the benzimidazole portion of Formula I.

In some embodiments, $R^1$ is selected from the group consisting of alkyl, cycloalkyl, heteroalkyl, arylalkyl, alkoxy, aryloxy, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In some embodiments, $R^2$, $R^3$, $R^4$, $R^5$ and $R^9$ are each independently selected from the group consisting of hydrogen, deuterium, alkyl, cycloalkyl, alkoxy, aryloxy, amino, silyl, aryl, heteroaryl, and combinations thereof.

In some embodiments, $R^1$ can be selected from the group consisting of aryl, heteroaryl, substituted aryl, and substituted heteroaryl.

In some embodiments, $R^1$ can be

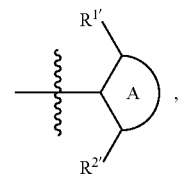

wherein $R^{1'}$ and $R^{2'}$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein at least one of $R^{1'}$ and $R^{2'}$ is not hydrogen or deuterium; and wherein A is 5-membered or 6-membered carbocyclic or heterocyclic aromatic ring that is optionally further substituted.

In some embodiments, (a) $R^2$ is mono, di, tri, tetra, or penta substituted, (b) $R^5$ is mono, di, tri or tetra substituted, or (c) both. In some embodiments, $R^5$ is mono, di, tri or tetra substituted. Where $R^5$ is at least monosubstituted. $R^5$ can be selected from the group consisting of hydrogen, deuterium, alkyl, cycloalkyl, aryl and combinations thereof.

As used herein, "substituted" indicates that a substituent other than H is bonded to the relevant carbon. Thus, where $R^2$ is monosubstituted, then one $R^2$ must be other than H. Similarly, where $R^3$ is disubstituted, the two of $R^3$ must be other than H. Similarly, where $R^2$ is unsubstituted $R^2$ is hydrogen for all available positions.

In some embodiments, $R^2$ is mono, di, tri, tetra or penta substituted. Where $R^2$ is at least monosubstituted, $R^2$ can be selected from the group consisting of hydrogen, deuterium, alkyl, cycloalkyl, aryl, and combinations thereof.

More specific examples of Formula I can include

Formula I(a)

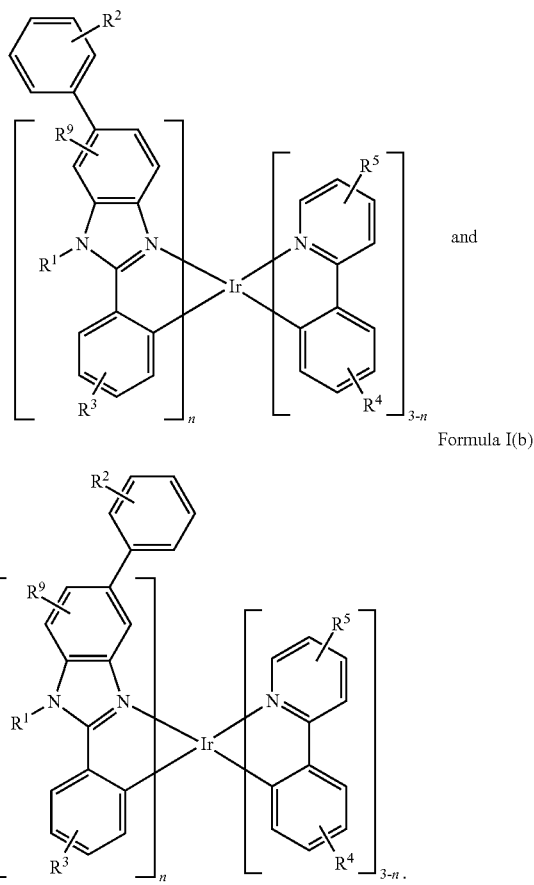

Formula I(b)

where $R^1$, $R^2$, $R^3$, $R^4$, $R^5$ and $R^9$ all have their meanings described elsewhere in this disclosure.

In some embodiments, Formula I can have the structure of Formula II shown below,

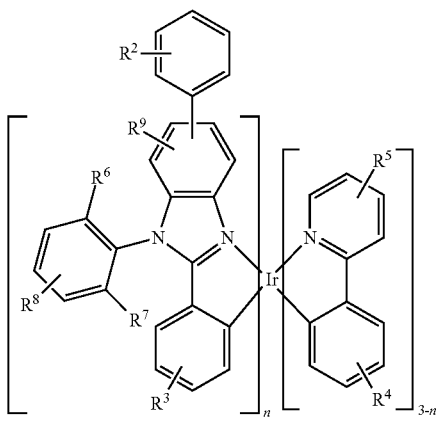

wherein $R^8$ represent mono, di, tri substitutions or no substitution, wherein $R^6$, $R^7$ and $R^8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and $R^1$, $R^2$, $R^3$, $R^4R^5$ and $R^9$ have their meanings as set forth elsewhere in this disclosure.

At least one of $R^6$ and $R^7$ can be selected from the group consisting of alkyl, cycloalkyl, aryl, and combinations thereof. Both $R^6$ and $R^7$ can be selected from the group consisting of alkyl, cycloalkyl, aryl, and combinations thereof.

In some embodiments of Formula II, $R^8$ is at least monosubstituted and is selected from the group consisting of hydrogen, deuterium, alkyl, cycloalkyl, aryl, and combinations thereof.

In some embodiments of Formula II, (a) at least one of $R^5$ and $R^8$ is mono, di, tri, or tetra substituted, (b) $R^2$ represents mono, di, tri, tetra, penta substitutions, or (c) both.

In some embodiments, moieties $R^2$, $R^3$, $R^4$, $R^5$, $R^6$, $R^7$, $R^8$ and $R^9$ are each independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2-methylphenyl, 2,6-dimethylphenyl, 2,4,6-trimethylphenyl, 2-isopropylphenyl, 2,6-diisopropylphenyl, 2,4,6-triisopropylphenyl, 2-phenylphenyl, 2,6-diphenylphenyl, 2,4,6-triphenylphenyl, and combinations thereof.

More specific examples of Formula II include:

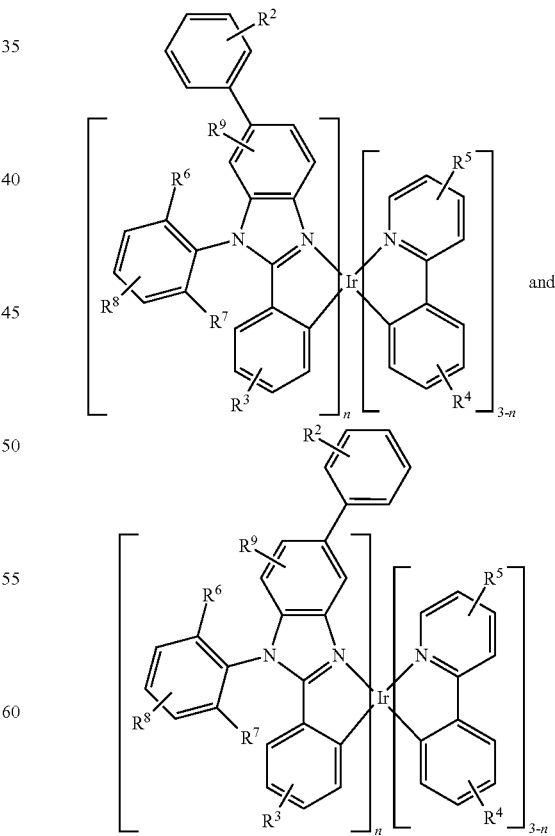

where $R^1$, $R^2$, $R^3R^4$, $R^5$, $R^6$, $R^7$, $R^8$ and $R^9$ all have their meanings described elsewhere in this disclosure.

Unless otherwise specified all options for $R^1$, $R^2$, $R^3$, $R^4$, $R^5$, $R^6$, $R^7$, $R^8$ and $R^9$ applicable to Formula I are equally applicable to Formula II, and all options for $R^1$, $R^2$, $R^3$, $R^4$, $R^5$, $R^6$, $R^7$, $R^8$ and $R^9$ applicable to Formula II are equally applicable to Formula I. Similarly, any combination of $R^1$, $R^2$, $R^3$, $R^4$, $R^5$, $R^6$, $R^7$, $R^8$ and $R^9$ described herein is envisioned regardless of whether the description is a combination of what are referred to as different embodiments. This applies regardless of where the options for $R^1$, $R^2$, $R^3$, $R^4$, $R^5$, $R^6$, $R^7$, $R^8$ and $R^9$ are listed.

In some embodiments, the phenylbenzimidazole heteroleptic complex can be selected from the group consisting of Compound 1

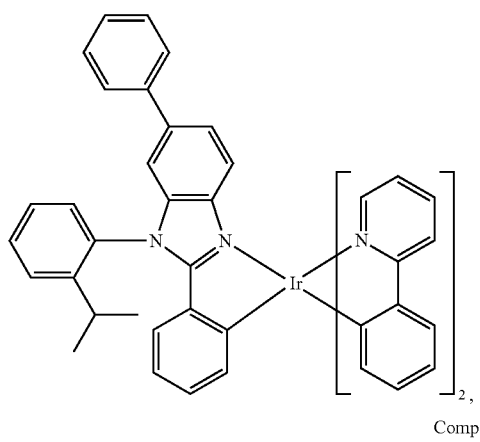

Compound 2

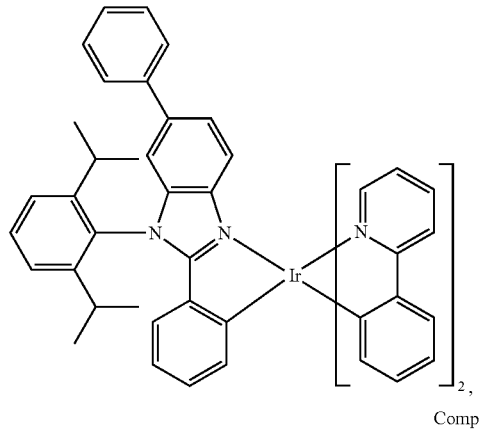

Compound 3

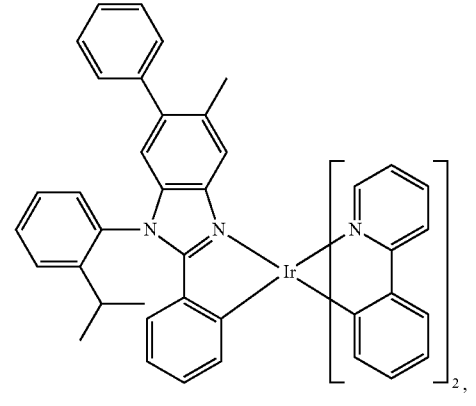

Compound 4

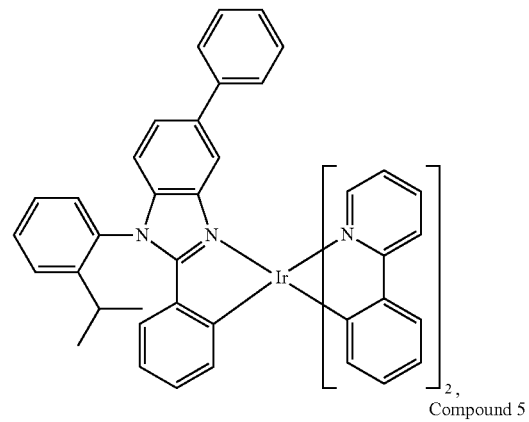

Compound 5

Compound 6

Compound 7

Compound 8
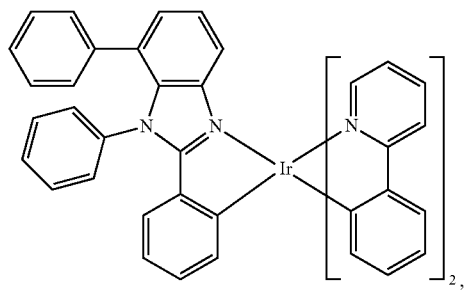
Compound 9
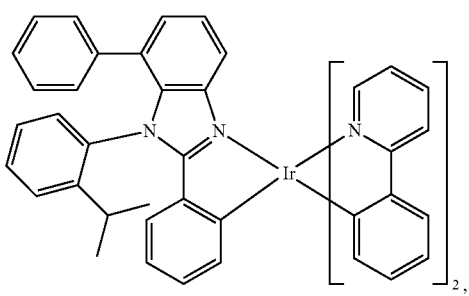
Compound 10
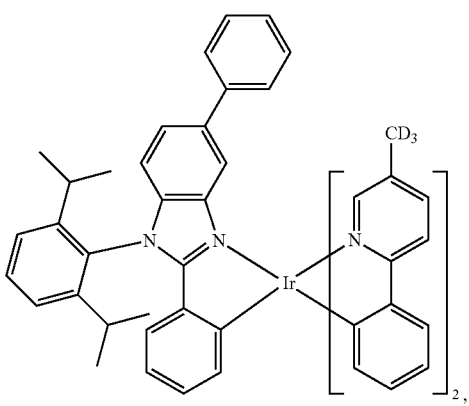
Compound 11
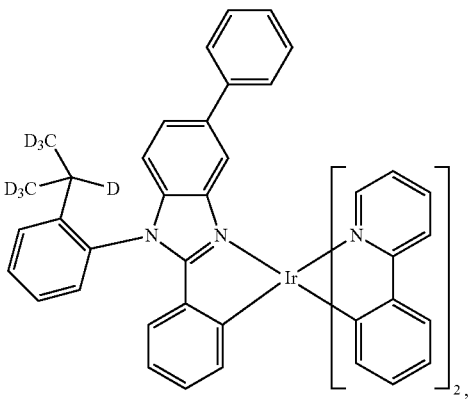
Compound 12
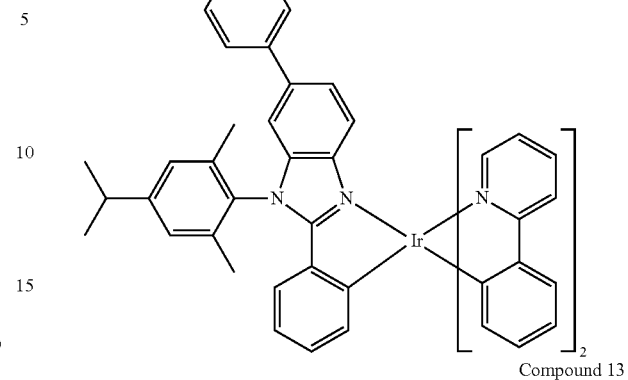
Compound 13
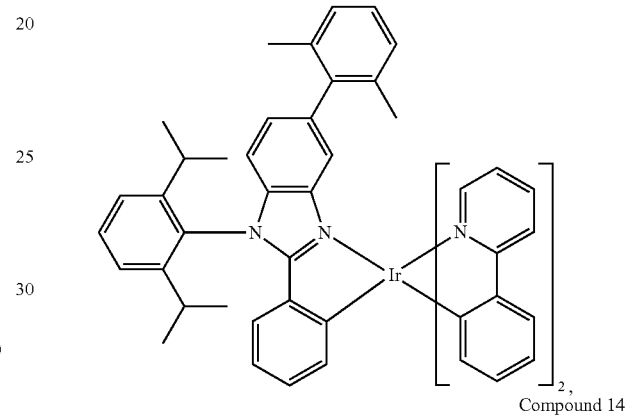
Compound 14
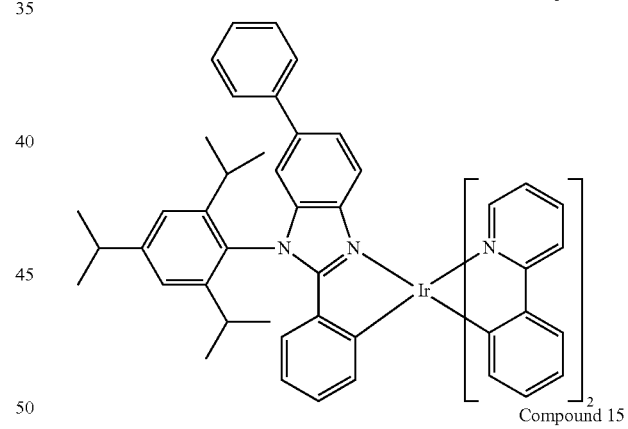
Compound 15
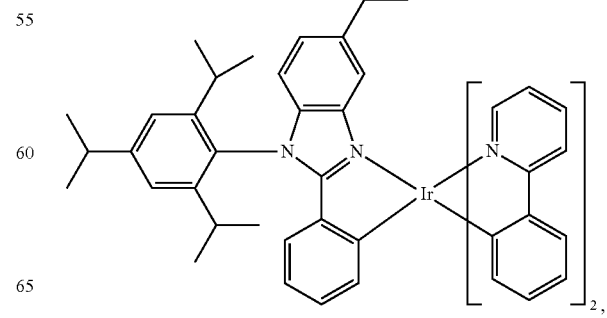

Compound 16
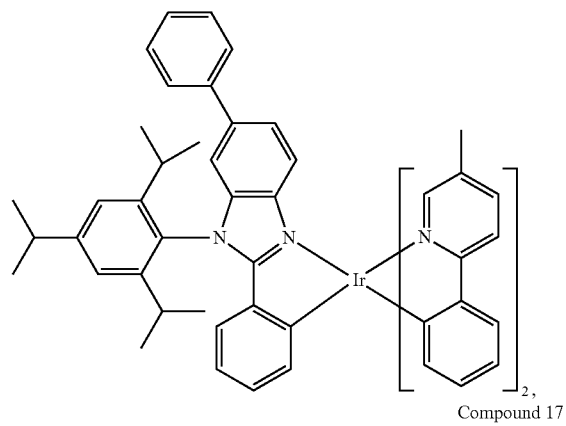
Compound 17
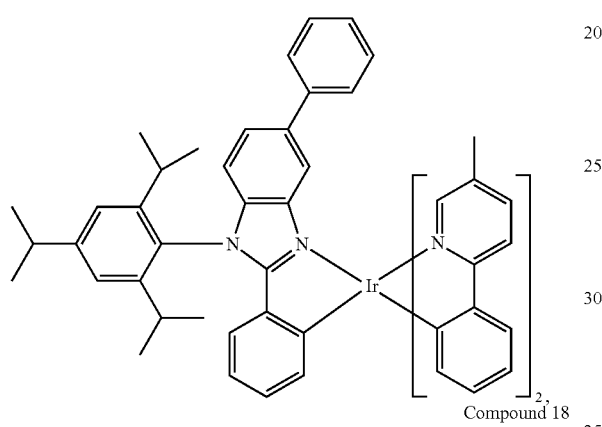
Compound 18
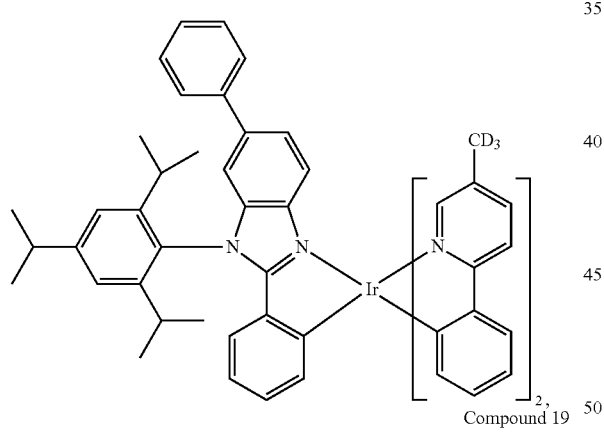
Compound 19
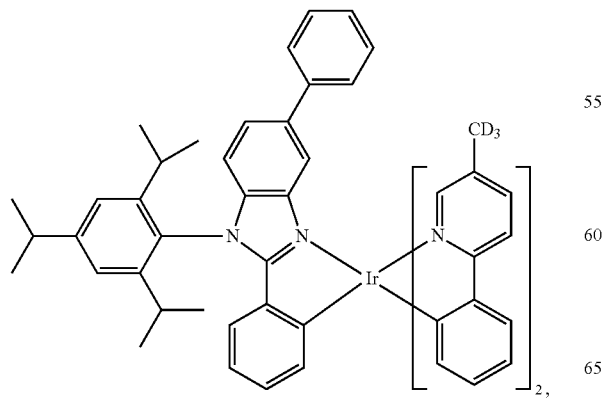
Compound 20
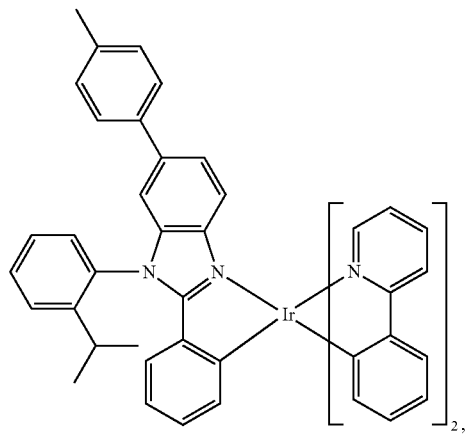
Compound 21
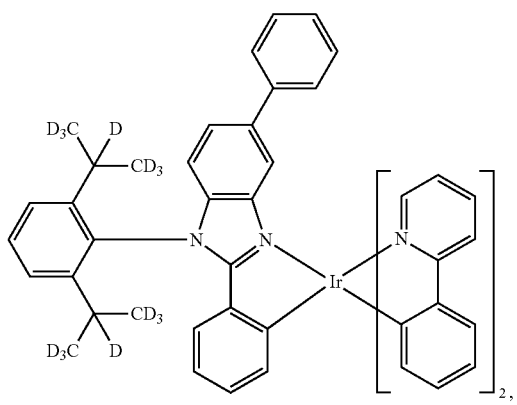
Compound 22
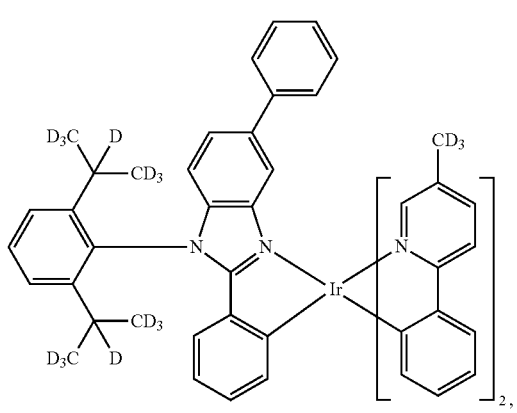

Compound 23
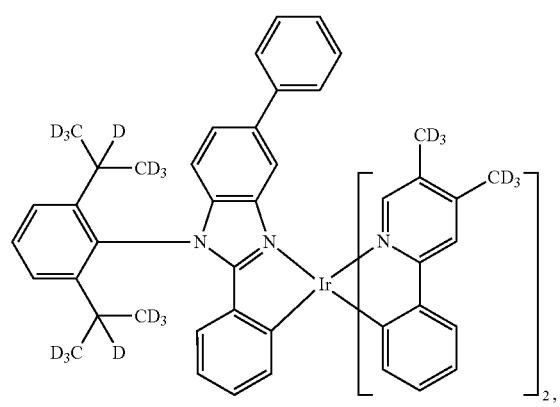
Compound 24
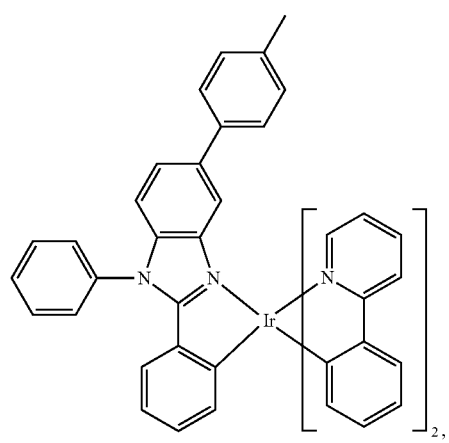
Compound 25
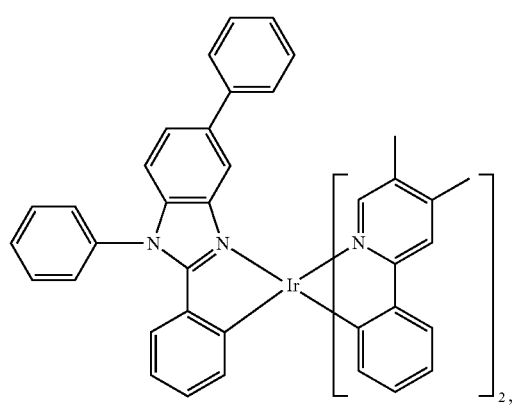
Compound 26
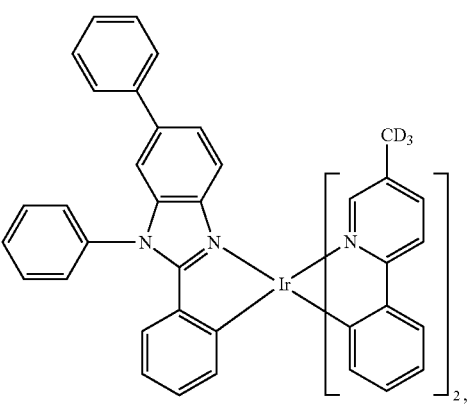
Compound 27
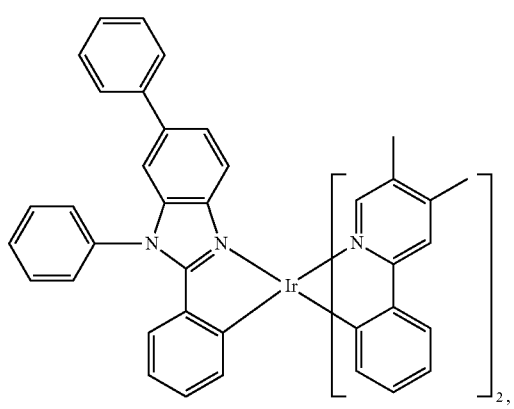
Compound 28
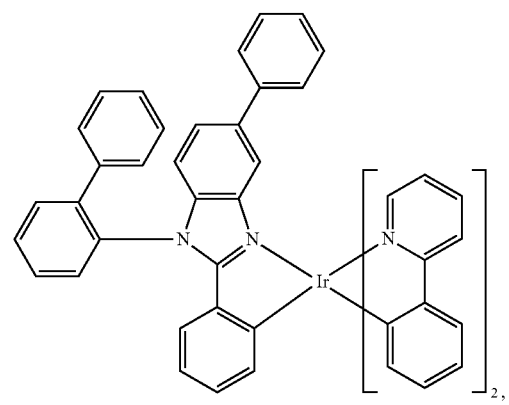

-continued

Compound 29

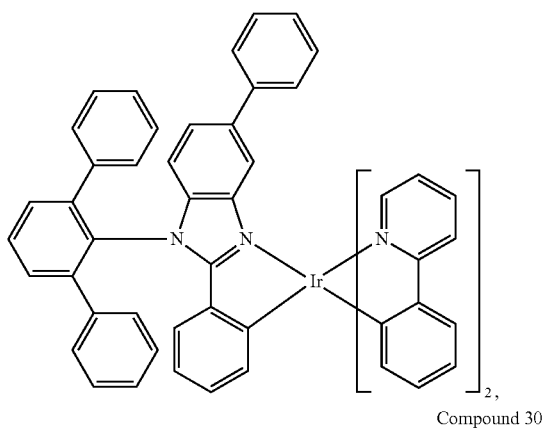

Compound 30

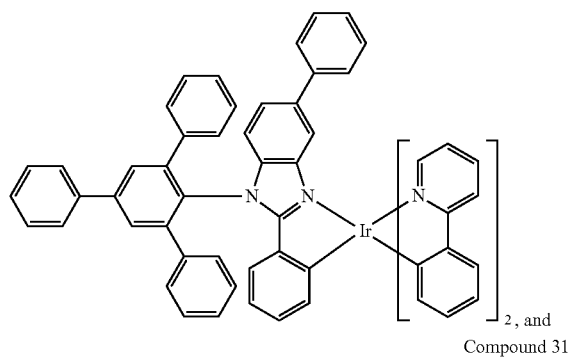

Compound 31

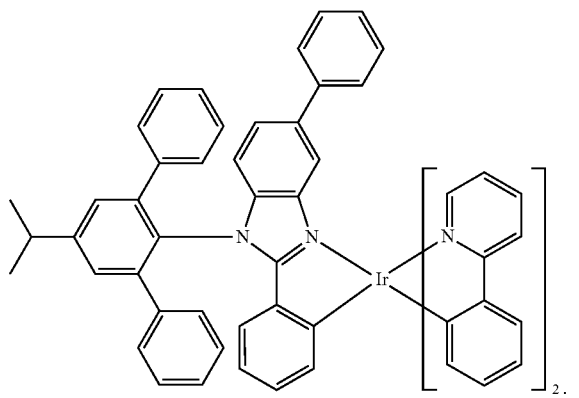

According to another aspect of the present disclosure, a first device is also provided. The first device includes an anode, a cathode, and an organic layer disposed between the anode and the cathode. The organic layer can include a compound according to Formulas I and II, and their variations as described.

The first device can be one or more of a consumer product, an organic light-emitting device and a lighting panel. The organic layer can be an emissive layer and the compound can be an emissive dopant in some embodiments, while the compound can be a non-emissive dopant in other embodiments.

The organic layer can also include a host. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound selected from the group consisting of carbazole, dibenzothiophene, dibenzofuran, dibenzoselenophene, azacarbazole, aza-dibenzothiophene, aza-dibenzofuran, and aza-dibenzoselenophene. The "aza" designation in the fragments described above, i.e., aza-dibenzofuran, aza-dibenzonethiophene, etc., means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein. The host can include a metal complex. The host can be a specific compound selected from the group consisting of:

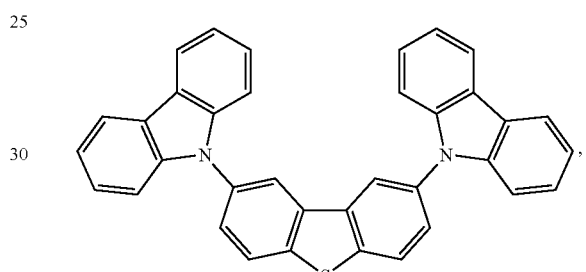

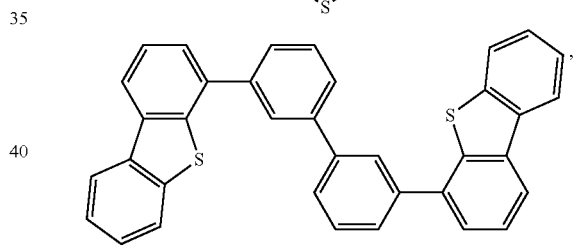

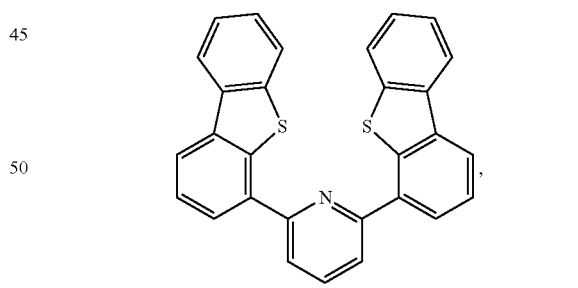

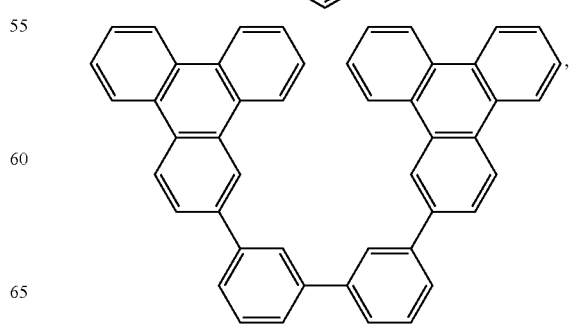

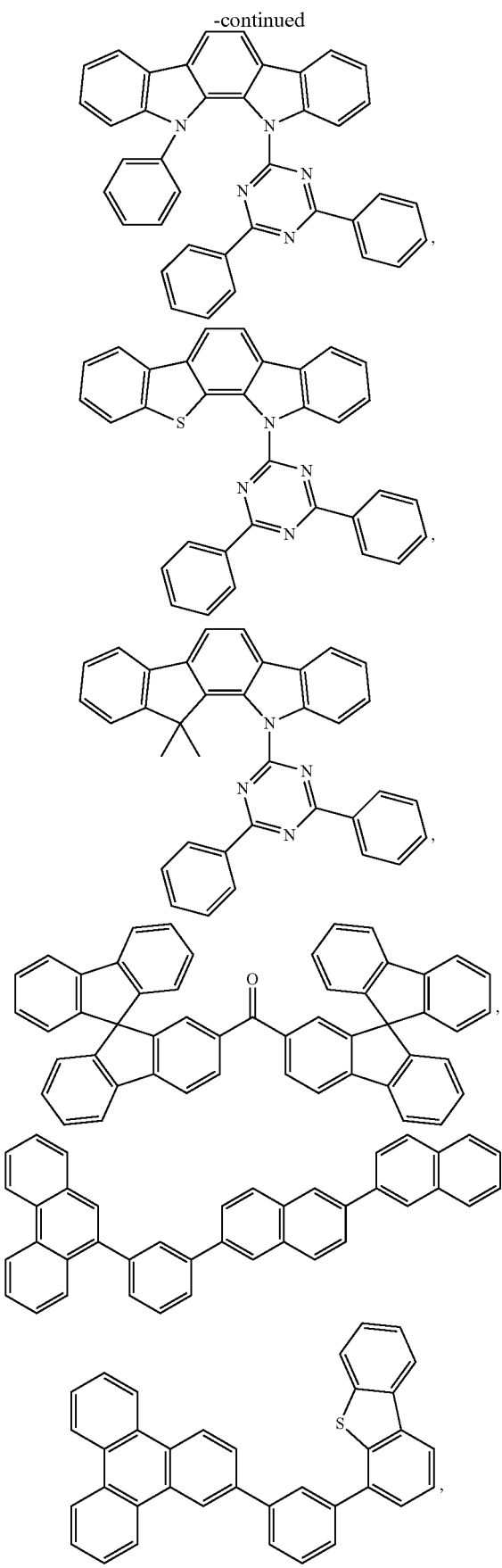

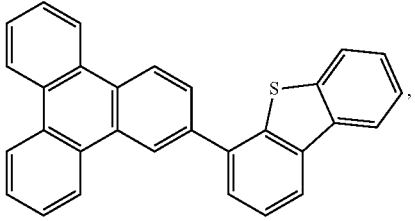

and combinations thereof.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

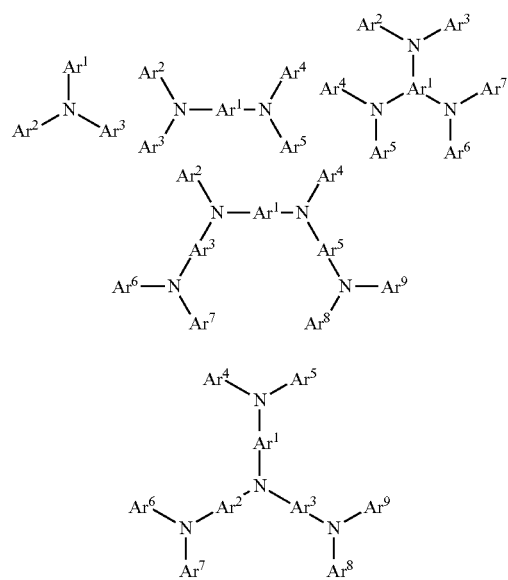

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

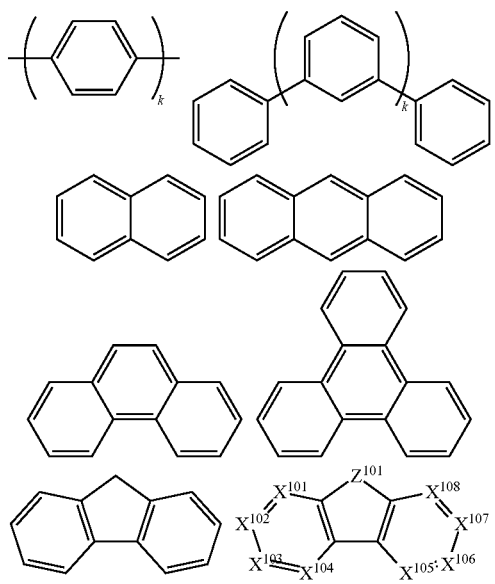

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

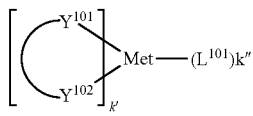

Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative.

In another aspect, $(Y^{101}\text{-}Y^{102})$ is a carbene ligand.

In another aspect, Met is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

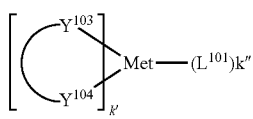

Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

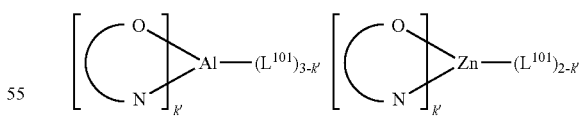

(O—N) is a bidentate ligand, having metal coordinated to atoms O and N.

In another aspect, Met is selected from Ir and Pt.

In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

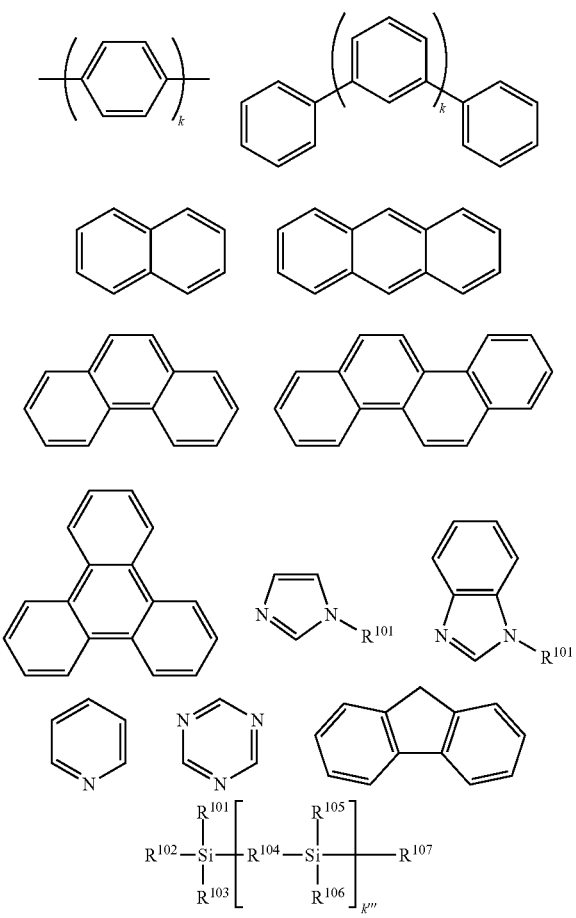

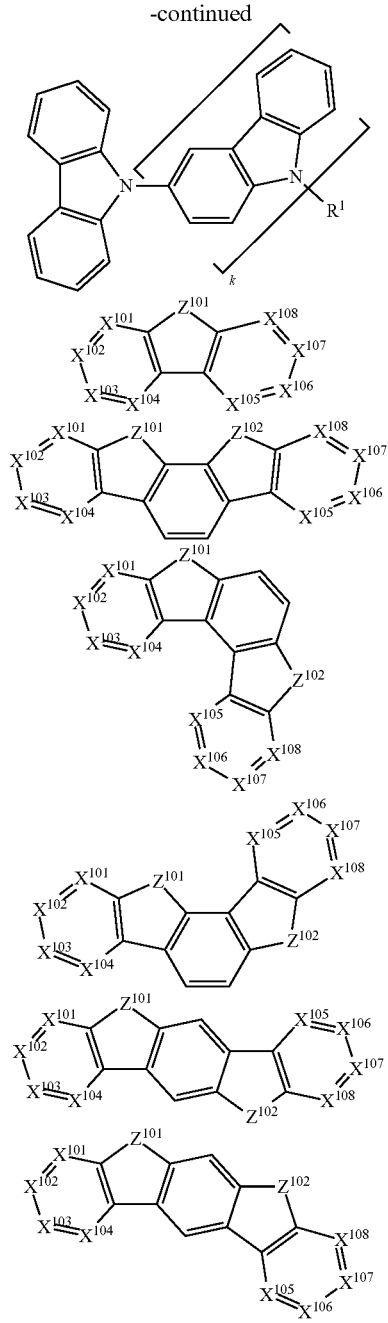

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20 or 1 to 20; k''' is an integer from 0 to 20.

$X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

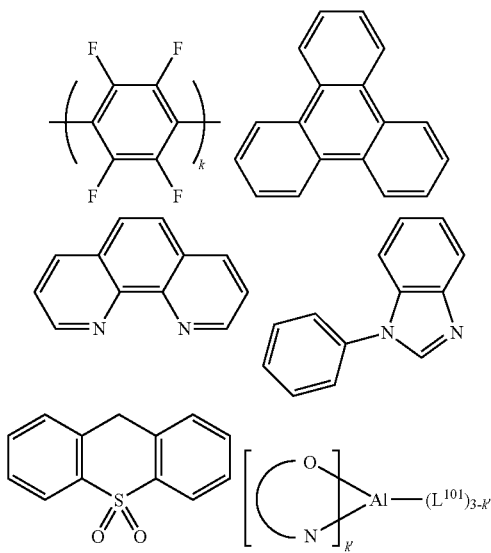

k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

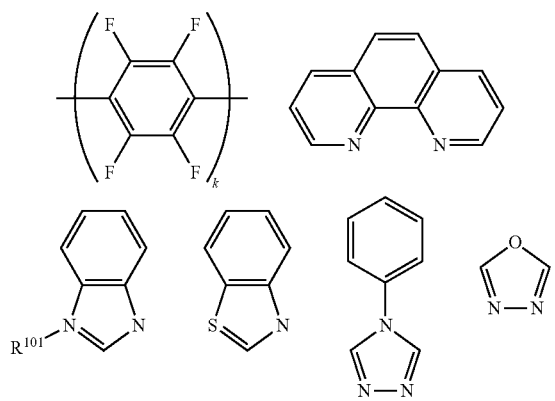

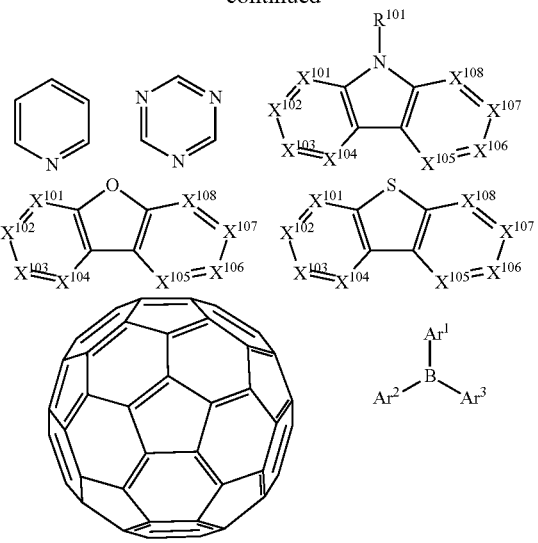

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

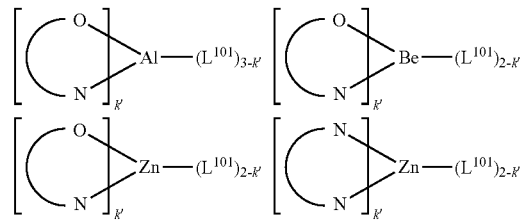

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |

TABLE 1-continued
| MATERIAL | EXAMPLES OF MATERIAL | PUBLICATIONS |
|---|---|---|
| Triarylamine or polythiophene polymers with conductivity dopants | 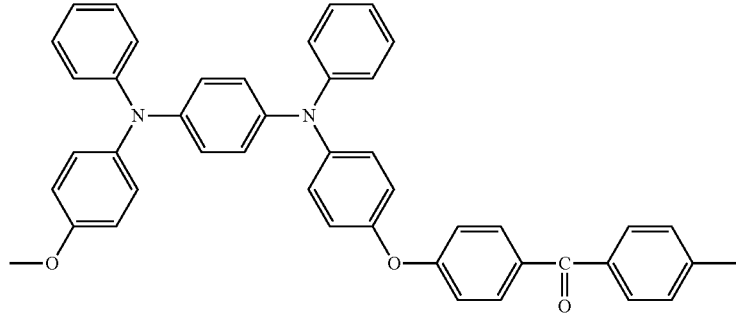 and 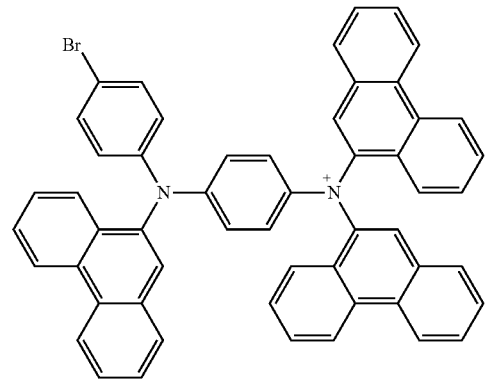 [SMILES: Brc1ccc(N(c2ccc(N(c3cc4ccccc4c4ccccc34)c3cc4ccccc4c4ccccc34)cc2)c2cc3ccccc3c3ccccc23)cc1] 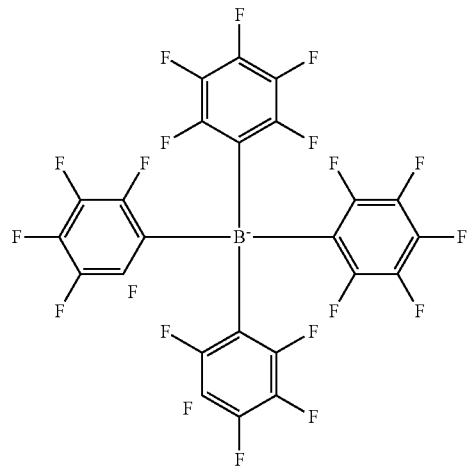 | EP1725079A1 |
| Organic compounds with conductive inorganic compounds, such as molybdenum and tungsten oxides | 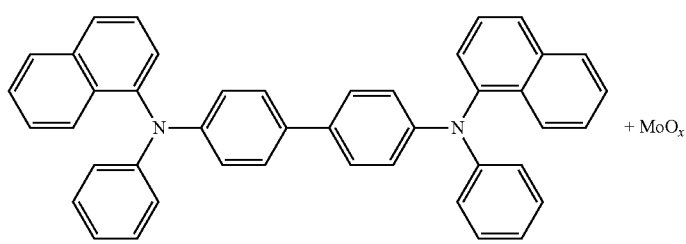 [SMILES: c1ccc(N(c2ccc(-c3ccc(N(c4ccccc4)c4cccc5ccccc45)cc3)cc2)c2cccc3ccccc23)cc1] + MoO$_x$ | US20050123751 SID Symposium Digest, 37, 923 (2006) WO2009018009 |

TABLE 1-continued

| MATERIAL | EXAMPLES OF MATERIAL | PUBLICATIONS |
|---|---|---|
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 1-continued
| MATERIAL | EXAMPLES OF MATERIAL | PUBLICATIONS |
|---|---|---|
| Hole transporting materials | | |
| Triarylamines (e.g., TPD, α-NPD) | 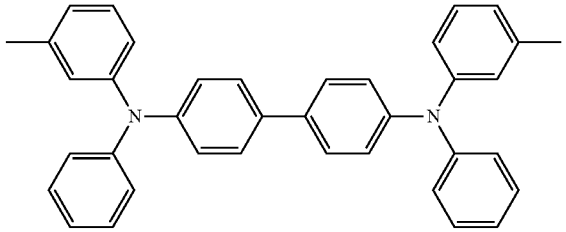 | Appl. Phys. Lett. 51, 913 (1987) |
| | 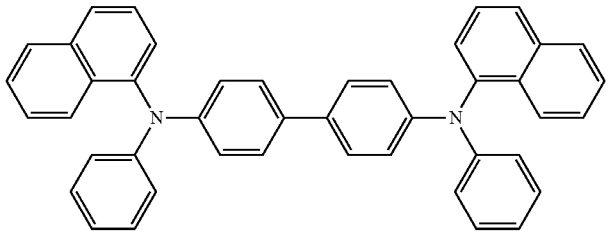 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 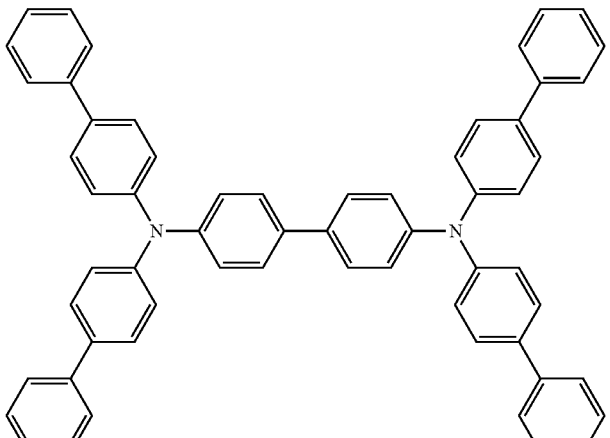 | EP650955 |
| | 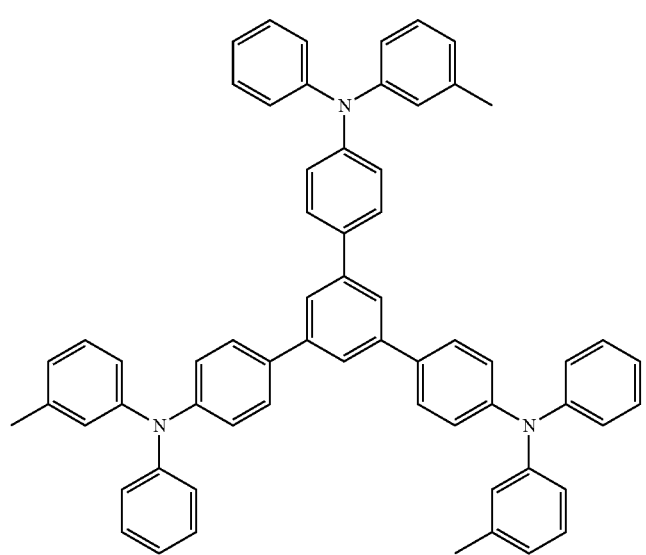 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 1-continued
| MATERIAL | EXAMPLES OF MATERIAL | PUBLICATIONS |
|---|---|---|
| | 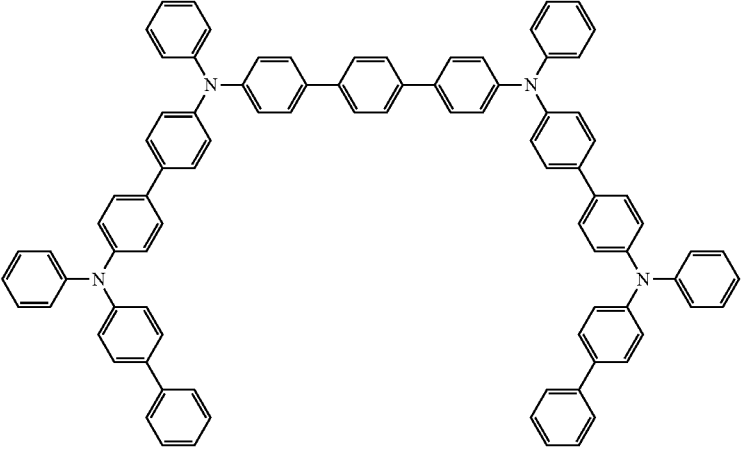 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 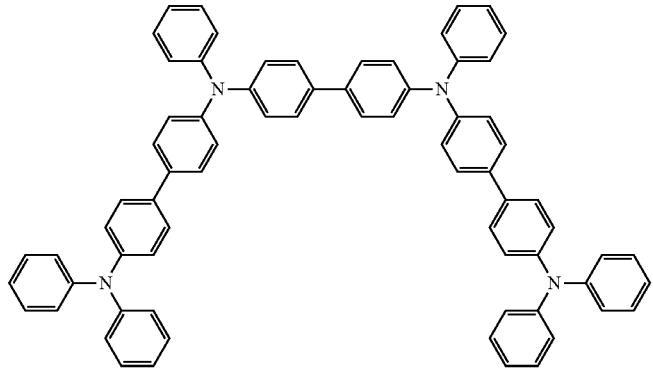 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 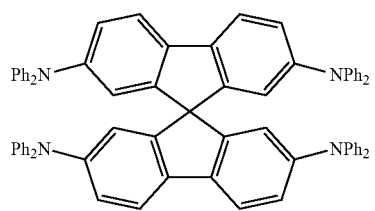 | Synth. Met. 91, 209 (1997) |
| Arylamine carbazole compounds | 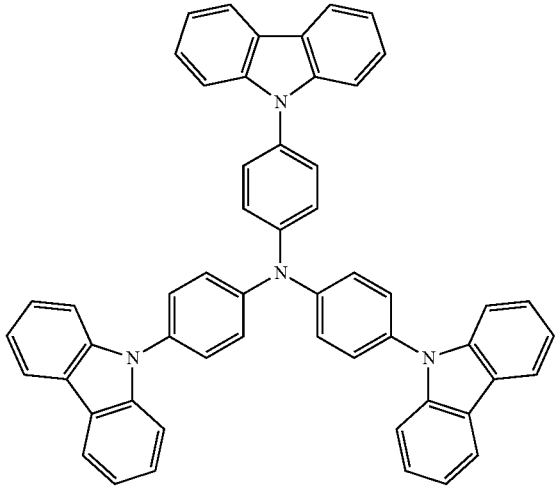 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 1-continued
| MATERIAL | EXAMPLES OF MATERIAL | PUBLICATIONS |
|---|---|---|
| Triarylamine with (di)benzothiophene/ (di)benzofuran | 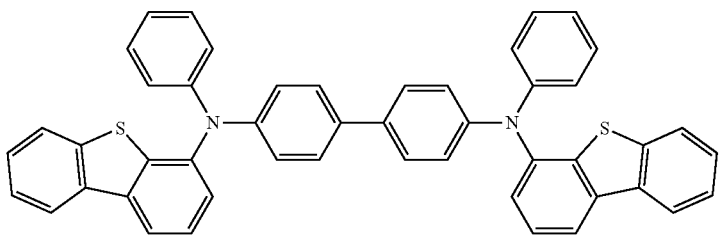 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 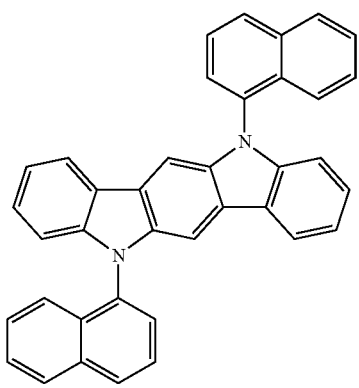 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 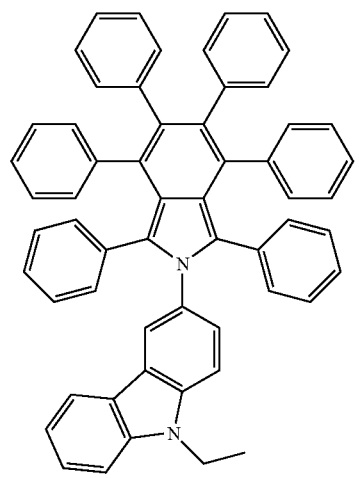 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 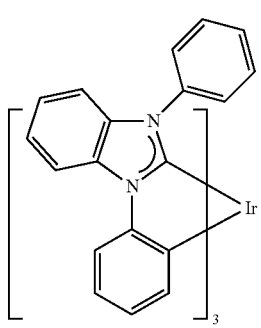 | US20080018221 |

TABLE 1-continued
| MATERIAL | EXAMPLES OF MATERIAL | PUBLICATIONS |
|---|---|---|
| Phosphorescent OLED host materials | | |
| Red hosts | | |
| Arylcarbazoles | 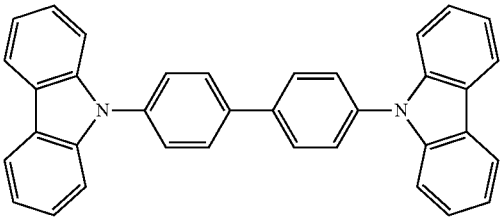 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 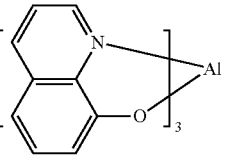 | Nature 395, 151 (1998) |
| | 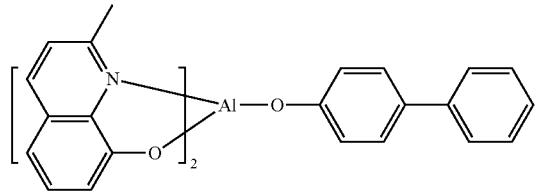 | US20060202194 |
| | 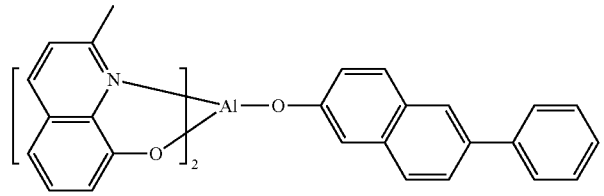 | WO2005014551 |
| | 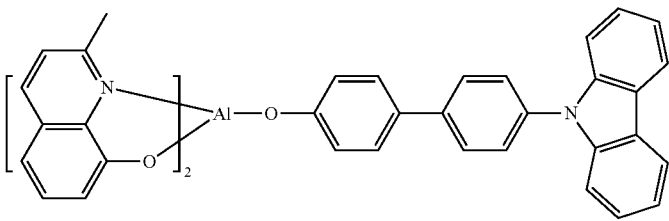 | WO2006072002 |
| Metal phenoxybenzothiazole compounds | 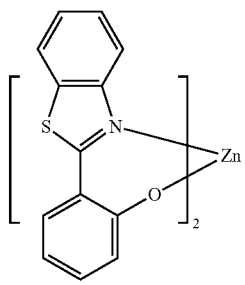 | Appl. Phys, Lett. 90, 123509 (2007) |
| Conjugated oligomers and polymers (e.g., polyfluorene) | 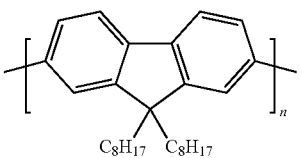 | Org. Electron. 1, 15 (2000) |

TABLE 1-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
|---|---|---|
| Arylcarbazoles | | Appl. Phys. Lett. 78, 1622 (2001) |
| | | US20030175553 |
| | | WO2001039234 |

TABLE 1-continued
| MATERIAL | EXAMPLES OF MATERIAL | PUBLICATIONS |
| --- | --- | --- |
| Aryltriphenylene compounds | 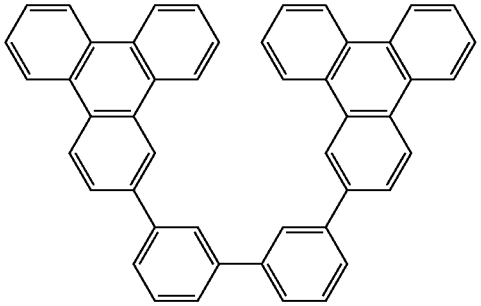 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 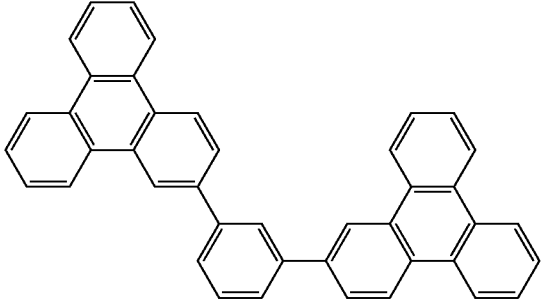 [SMILES: c1cc(-c2ccc3c4ccccc4c4ccccc4c3c2)cc(-c2ccc3c4ccccc4c4ccccc4c3c2)c1] | US20060280965 |
| | 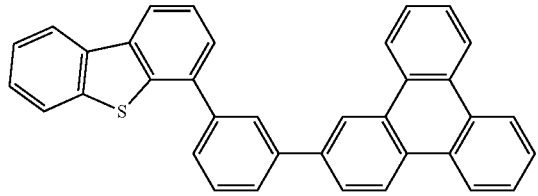 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 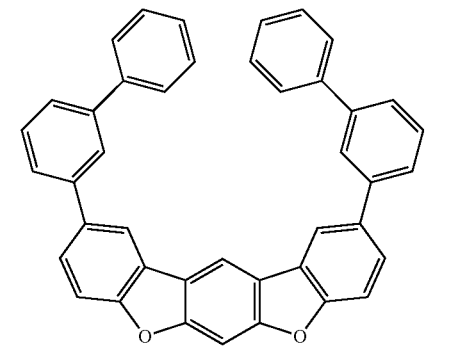 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 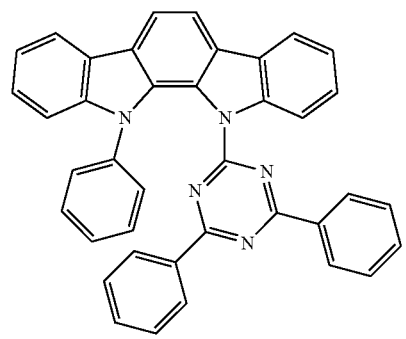 [SMILES: c1ccc(-c2nc(-c3ccccc3)nc(-n3c4ccccc4c4ccc5c6ccccc6n(-c6ccccc6)c5c43)n2)cc1] | WO2008056746 |

| MATERIAL | EXAMPLES OF MATERIAL | PUBLICATIONS |
| --- | --- | --- |
| | | WO2010107244 |
| Aza-carbazole/ DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |

TABLE 1-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 1-continued

| MATERIAL | EXAMPLES OF MATERIAL | PUBLICATIONS |
| --- | --- | --- |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

| MATERIAL | EXAMPLES OF MATERIAL | PUBLICATIONS |
|---|---|---|
| Metal phenoxypyridine compounds | 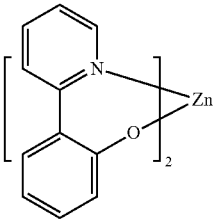 | WO2005030900 |
| Metal coordination complexes (e.g., Zn, Al with N^N ligands) | 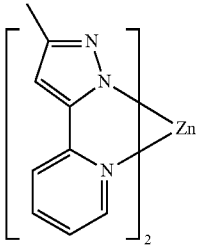 | US20040137268, US20040137267 |
| Blue hosts | | |
| Arylcarbazoles | 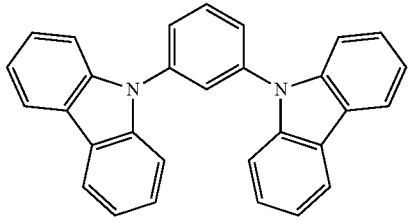 [SMILES: c1cc(-n2c3ccccc3c3ccccc32)cc(-n2c3ccccc3c3ccccc32)c1] | Appl. Phys. Lett. 82, 2422 (2003) |
| | 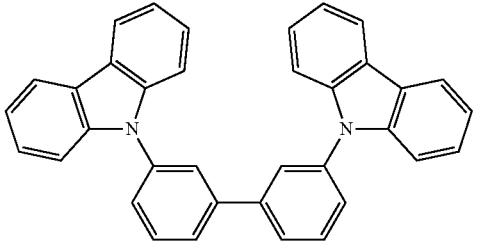 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 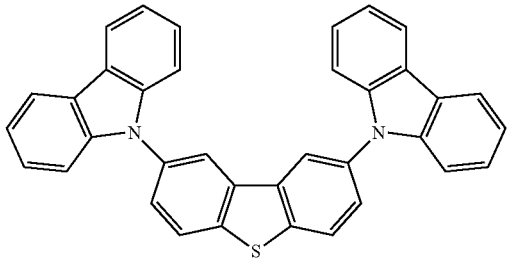 [SMILES: c1ccc2c(c1)c1ccccc1n2-c1ccc2sc3ccc(-n4c5ccccc5c5ccccc54)cc3c2c1] | WO2006114966, US20090167162 |
| | 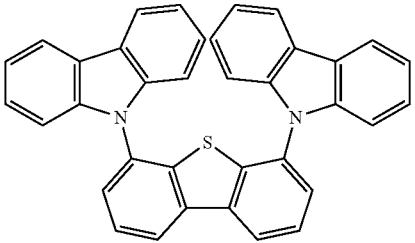 [SMILES: c1cc(-n2c3ccccc3c3ccccc32)c2sc3c(-n4c5ccccc5c5ccccc54)cccc3c2c1] | US20090167162 |

TABLE 1-continued
| MATERIAL | EXAMPLES OF MATERIAL | PUBLICATIONS |
|---|---|---|
| | 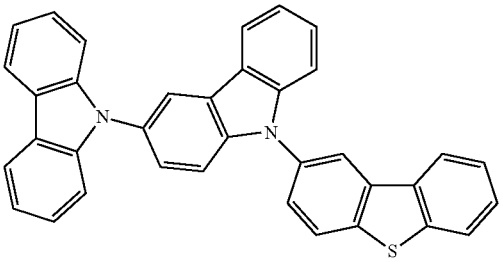 [SMILES: c1ccc2c(c1)sc1ccc(-n3c4ccccc4c4cc(-n5c6ccccc6c6ccccc65)ccc43)cc12] | WO2009086028 |
| | 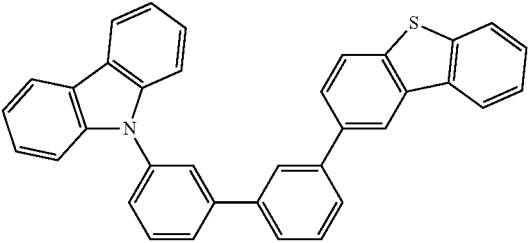 [SMILES: c1cc(-c2cccc(-n3c4ccccc4c4ccccc43)c2)cc(-c2ccc3sc4ccccc4c3c2)c1] | US20090030202, US20090017330 |
| | 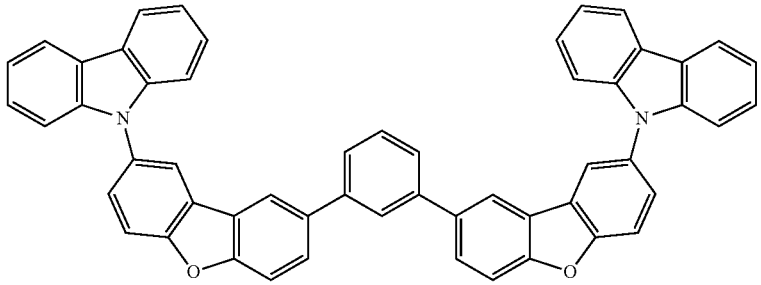 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 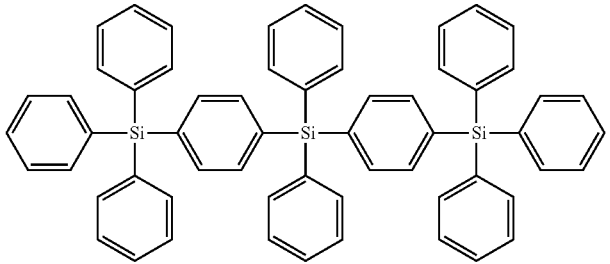 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 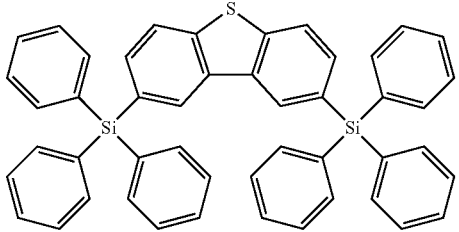 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE 1-continued

| MATERIAL | EXAMPLES OF MATERIAL | PUBLICATIONS |
|---|---|---|
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater.<br>19, 739<br>(2007) |

TABLE 1-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE 1-continued

| MATERIAL | EXAMPLES OF MATERIAL | PUBLICATIONS |
| --- | --- | --- |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

| MATERIAL | EXAMPLES OF MATERIAL | PUBLICATIONS |
|---|---|---|
| | 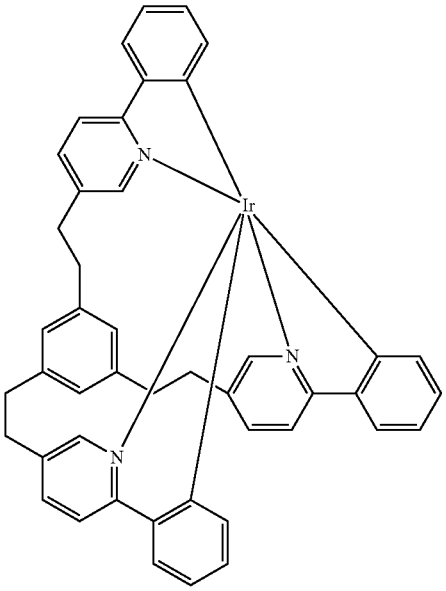 | U.S. Pat. No. 7,332,232 |
| | 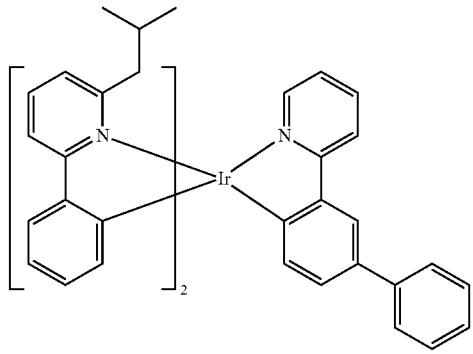 | US20090108737 |
| | 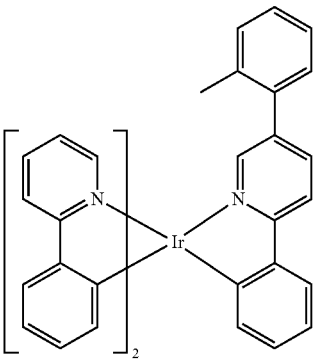 | WO2010028151 |

TABLE 1-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE 1-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670 JP2007123392 |
| | | WO2010086089, WO2011044988 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 1-continued

| MATERIAL | EXAMPLES OF MATERIAL | PUBLICATIONS |
|---|---|---|
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

| MATERIAL | EXAMPLES OF MATERIAL | PUBLICATIONS |
| --- | --- | --- |
|  | 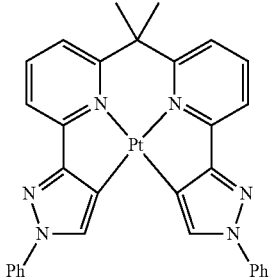 | US20060263635 |
|  | 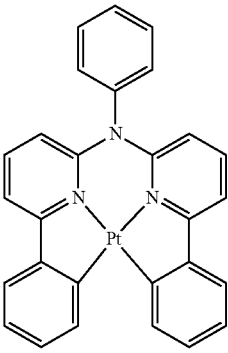 | US20060182992<br>US20070103060 |
| Cu complexes | 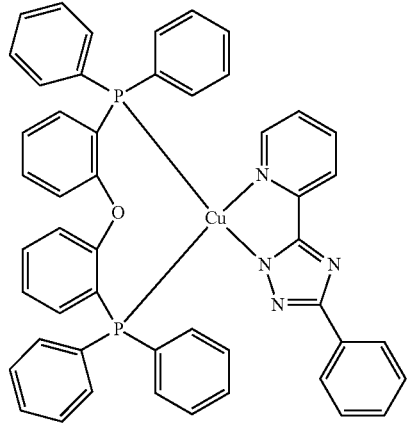 | WO2009000673 |
|  | 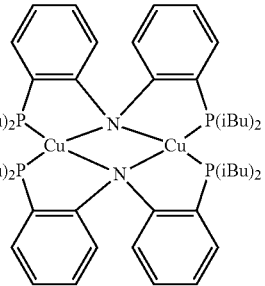 | US20070111026 |

TABLE 1-continued

| MATERIAL | EXAMPLES OF MATERIAL | PUBLICATIONS |
| --- | --- | --- |
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |
| Deuterated organometallic complexes | | US20030138657 |

TABLE 1-continued
| MATERIAL | EXAMPLES OF MATERIAL | PUBLICATIONS |
|---|---|---|
| Organometallic complexes with two or more metal centers | 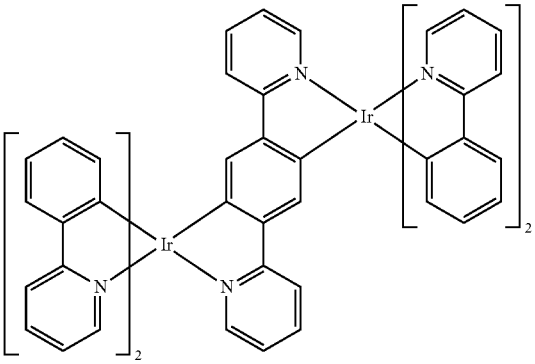 | US20030152802 |
| | 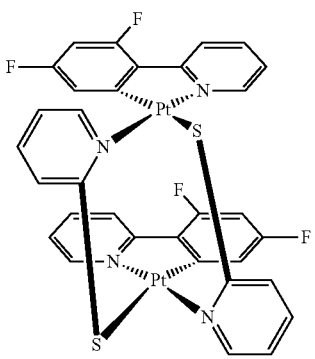 | U.S. Pat. No. 7,090,928 |
| Blue dopants | | |
| Iridium(III) organometallic complexes | 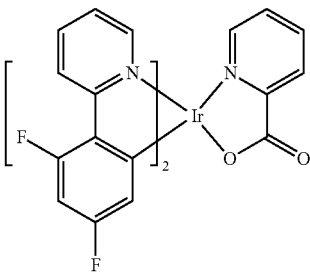 | WO2002002714 |
| | 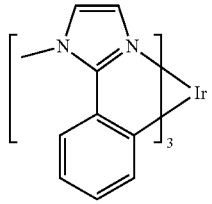 | WO2006009024 |
| | 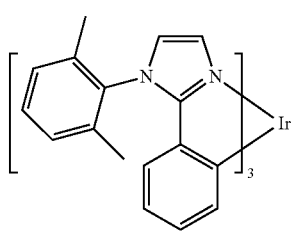 | US20060251923<br>US20110057559<br>US20110204333 |

TABLE 1-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 1-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |

TABLE 1-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 1-continued
| MATERIAL | EXAMPLES OF MATERIAL | PUBLICATIONS |
|---|---|---|
|  | 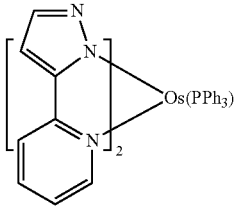 | Organometallics 23, 3745 (2004) |
| Gold complexes | 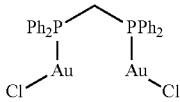 | Appl. Phys. Lett. 74, 1361 (1999) |
| Platinum(II) complexes | 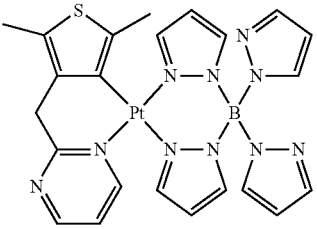 | WO2006098120, WO2006103874 |
| Pt tetradentate complexes with at least one metal-carbene bond | 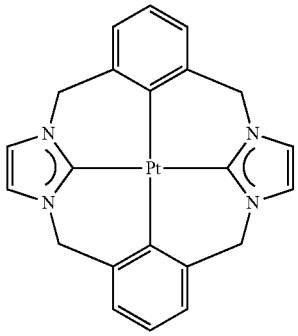 | U.S. Pat. No. 7,655,323 |
| Exciton/hole blocking layer materials | | |
| Bathocuprine compounds (e.g., BCP, BPhen) | 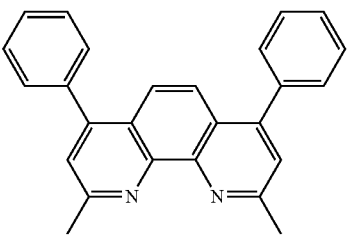 [SMILES: Cc1cc(-c2ccccc2)c2ccc3c(-c4ccccc4)cc(C)nc3c2n1] | Appl. Phys. Lett. 75, 4 (1999) |
|  | 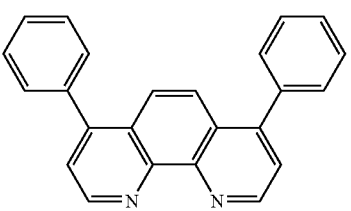 [SMILES: c1ccc(-c2ccnc3c2ccc2c(-c4ccccc4)ccnc23)cc1] | Appl. Phys. Lett. 79, 449 (2001) |

| MATERIAL | EXAMPLES OF MATERIAL | PUBLICATIONS |
|---|---|---|
| Metal 8-hydroxyquinolates (e.g., BAlq) | 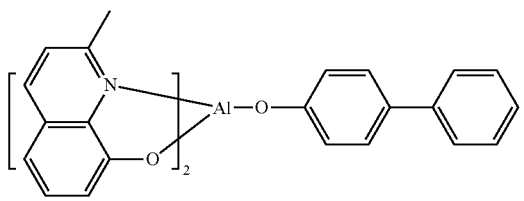 | Appl. Phys. Lett. 81, 162 (2002) |
| 5-member ring electron deficient heterocycles such as triazole, oxadiazole, imidazole, benzoimidazole | 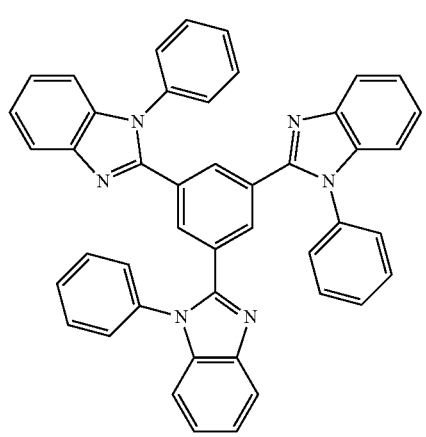 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 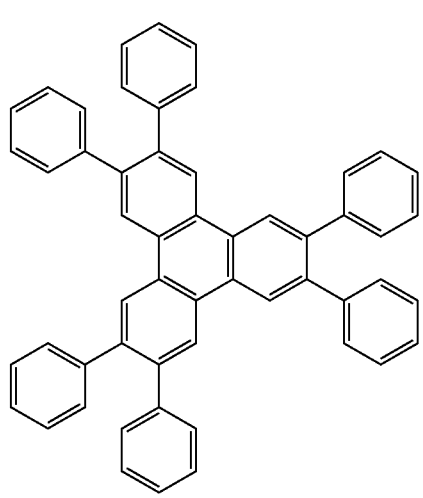 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued

| MATERIAL | EXAMPLES OF MATERIAL | PUBLICATIONS |
|---|---|---|
| Fluorinated aromatic compounds | | Appl. Phys. Lett. 79. 156 (2001) |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

TABLE 1-continued

| MATERIAL | EXAMPLES OF MATERIAL | PUBLICATIONS |
| --- | --- | --- |
| | Electron transporting materials | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) U.S. Pat. No. 7,230,107 |

TABLE 1-continued

| MATERIAL | EXAMPLES OF MATERIAL | PUBLICATIONS |
| --- | --- | --- |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued

| MATERIAL | EXAMPLES OF MATERIAL | PUBLICATIONS |
|---|---|---|
| Siloie compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |
| Triazine complexes | | US20040036077 |

TABLE 1-continued

| MATERIAL | EXAMPLES OF MATERIAL | PUBLICATIONS |
|---|---|---|
| Zn (N^N) complexes | 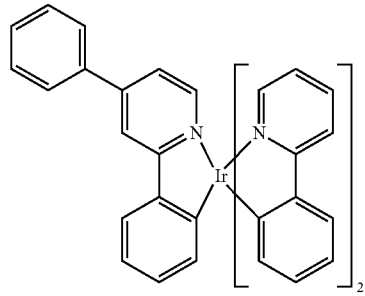 | U.S. Pat. No. 6,528,187 |

EXPERIMENTAL

Comparative Data—Peak Emission Wavelength

For phosphorescent iridium complexes, the HOMO/LUMO levels often determine their emission properties. Within the same ligand family, introducing substitutions to alter the HOMO/LUMO levels can result in blue shift or red shift. For example, extending conjugation of the ligand where the LUMO is located on the ligand can significantly red shift the emission. For example, tris(2-phenylpyridine) iridium(III) emits around 517 nm in dichloromethane solution at room temperature. By substituting the pyridine ring with a phenyl group on one of the ligands, Compound Y has a yellow emission with peak wavelength at 578 nm under the same condition. The phenyl substitution significantly lowered the LUMO of the complex, resulting in 61 nm red shift.

Compound Y

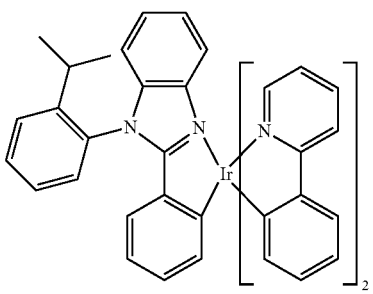

U.S. Patent Application Publication No. 20100141127 discloses comparative Compound A (below) and reports a green emission with a peak wavelength of 518 nm in 2-methyltetrahydrofuran at room temperature.

Compound A

Compound 4

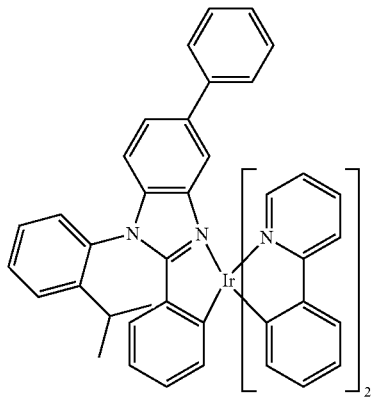

The lowest unoccupied molecular orbital (LUMO) of comparative Compound A is located on the benzimidazole part of the ligand. When a phenyl substitution is introduced to the benzene ring, as in Compound 4 (above), it was expected that the emission should be significantly red-shifted compared to comparative Compound A because the phenyl substitution would lower the LUMO of the complex. This would prevent Compound 4 for being useful as a green emitter.

Cyclic voltammetry confirms that the LUMO was indeed lower for Compound 4. The reduction potentials of comparative Compound A and Compound 4 were measured to be −2.71 V and −2.66 V vs Fc/Fc$^+$, respectively. However, Compound 4 unexpectedly showed a green emission with peak wavelength at 514 nm, which is about 4 nm blue shifted compared to comparative compound A in solution at room temperature. Therefore, the inventive compounds showed unexpected photophysical properties. In addition, it was discovered that inventive compounds showed higher efficiency and lower driving voltage in OLED devices.

Synthesis of Compound 1

Preparation of 3-fluoro-4-nitro-1,1'-biphenyl

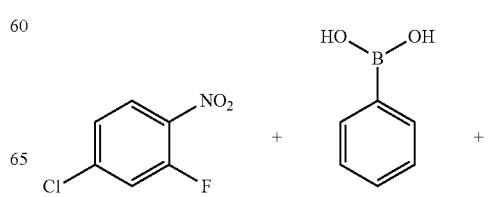

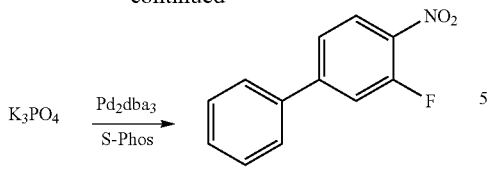

4-chloro-2-fluoro-1-nitrobenzene (15 g, 85 mmol), phenylboronic acid (15.63 g, 128 mmol), potassium phosphate monohydrate (59.0 g, 256 mmol) were added to 428 mL 8:1 mixture of toluene and water. The reaction mixture was degassed for 20 minutes and $Pd_2dba_3$ (0.782 g, 0.854 mmol) and S-Phos (1.40 grams, 3.42 mmol) were added. Degassing continued for another 10 minutes and reaction mixture was heated to reflux for 5 h. The sample was purified by column chromatographed to give 11.5 grams (62%) of the 3-fluoro-4-nitro-1,1'-biphenyl.

Preparation of N-(2-isopropylphenyl)-4-nitro-[1,1'-biphenyl]-3-amine

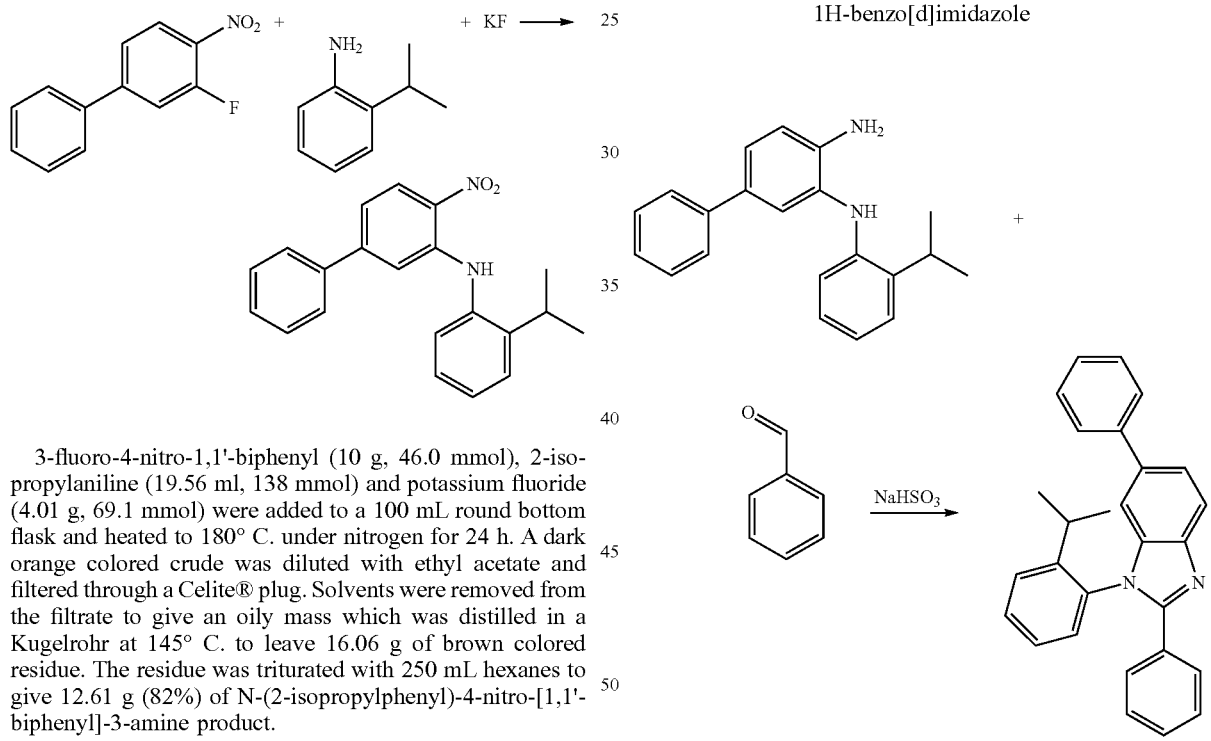

3-fluoro-4-nitro-1,1'-biphenyl (10 g, 46.0 mmol), 2-isopropylaniline (19.56 ml, 138 mmol) and potassium fluoride (4.01 g, 69.1 mmol) were added to a 100 mL round bottom flask and heated to 180° C. under nitrogen for 24 h. A dark orange colored crude was diluted with ethyl acetate and filtered through a Celite® plug. Solvents were removed from the filtrate to give an oily mass which was distilled in a Kugelrohr at 145° C. to leave 16.06 g of brown colored residue. The residue was triturated with 250 mL hexanes to give 12.61 g (82%) of N-(2-isopropylphenyl)-4-nitro-[1,1'-biphenyl]-3-amine product.

Preparation of N3-(2-isopropylphenyl)-[1,1'-biphenyl]-3,4-diamine

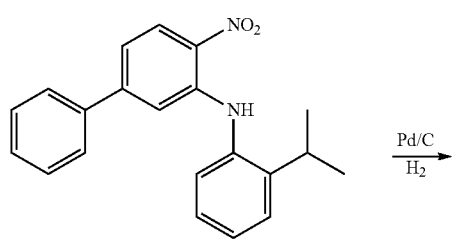

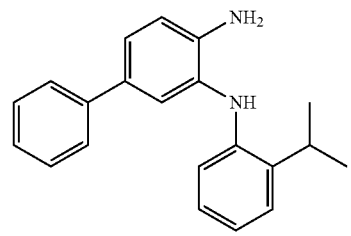

To a flask containing 10% palladium on charcoal (1.26 g, 1.184 mmol), N-(2-isopropylphenyl)-4-nitro-[1,1'-biphenyl]-3-amine (12.68 g, 38.1 mmol) dissolved in 200 mL ethanol and 20 mL glacial acetic acid was added. The reaction mixture was hydrogenated at 50 psi for 4 h. The crude reaction mixture was filtered through a Celite® pad and the filtrate was evaporated on the rotovap followed by Kugelrohr to give 11.5 g (99%) of N3-(2-isopropylphenyl)-[1,1'-biphenyl]-3,4-diamine product.

Preparation of 1-(2-isopropylphenyl)-2,6-diphenyl-1H-benzo[d]imidazole

N3-(2-isopropylphenyl)-[1,1'-biphenyl]-3,4-diamine (12.6 g, 41.7 mmol), sodium bisulfite (7.80 g, 75.0 mmol) and benzaldehyde (5.10 ml, 50.0 mmol) were added to 200 mL DMF and heated to 125° C. for 18 h. The crude product was poured over brine and extracted with ethyl acetate. The organic layer was washed with brine and finally dried over $MgSO_4$. The organic solvents were removed under reduced pressure and the crude was purified by column chromatography using 1:1 DCM/hexanes followed by 1-3% ethyl acetate/DCM as eluent. 1-(2-isopropylphenyl)-2,6-diphenyl-1H-benzo[d]imidazole (9.89 g, 25.5 mmol, 61.1% yield) was isolated from first batch of recrystallization from boiling hexanes and DCM.

Synthesis of Compound 1

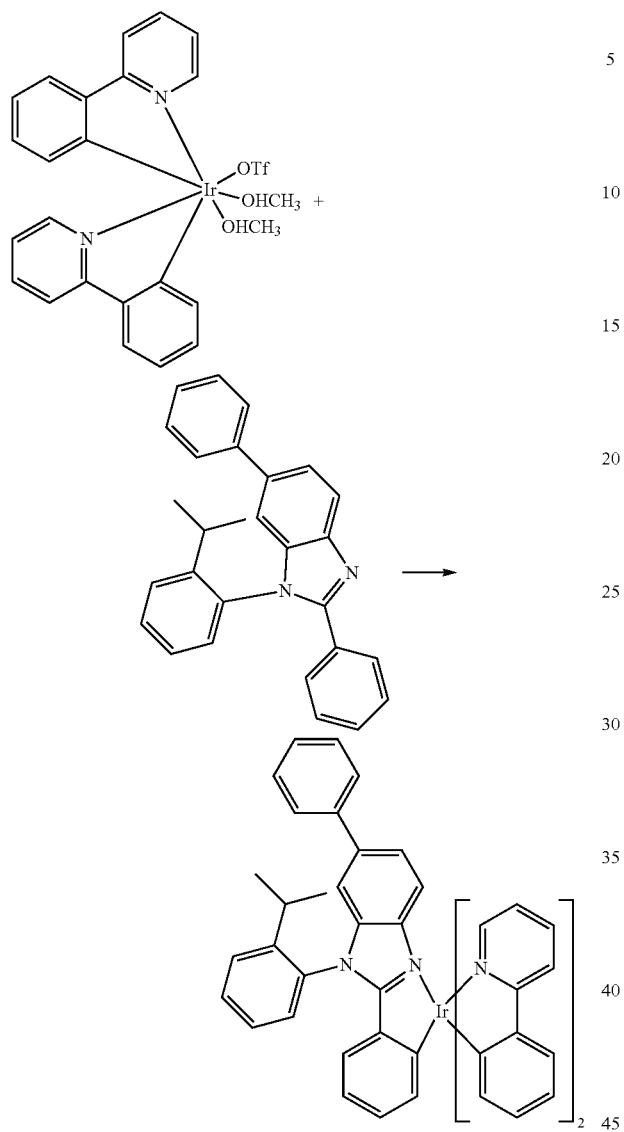

Iridium complex (2.0 g, 2.80 mmol) and 1-(2-isopropylphenyl)-2,6-diphenyl-1H-benzo[d]imidazole (4.35 g, 11.21 mmol) were added to 100 mL ethanol and degassed for 30 minutes. Reaction mixture was heated to reflux for 18 h. Cooled reaction mixture was filtered thru a Celite® plug. Precipitates were purified by column chromatography. 1.77 g (71%) of Compound 1 product was obtained.

Synthesis of Compound 2

Preparation of N-(2,6-di-isopropylphenyl)-4-nitro-[1,1'-biphenyl]-3-amine

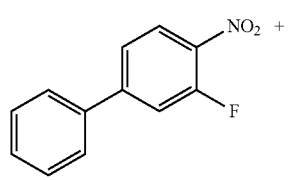

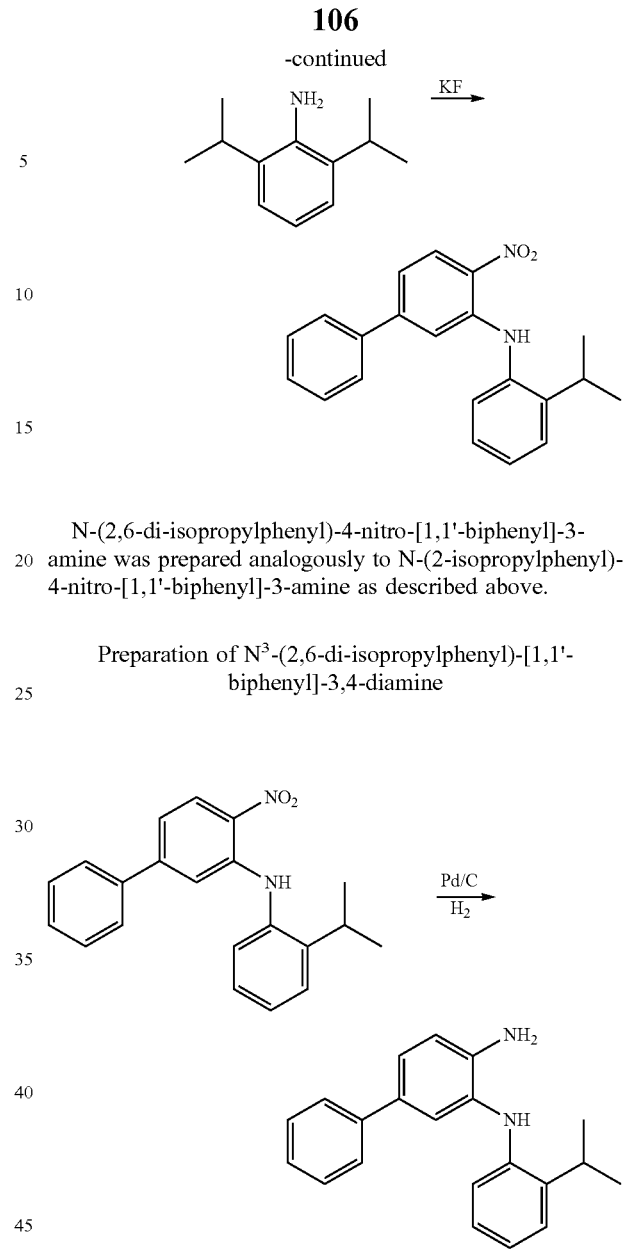

N-(2,6-di-isopropylphenyl)-4-nitro-[1,1'-biphenyl]-3-amine was prepared analogously to N-(2-isopropylphenyl)-4-nitro-[1,1'-biphenyl]-3-amine as described above.

Preparation of $N^3$-(2,6-di-isopropylphenyl)-[1,1'-biphenyl]-3,4-diamine

N3-(2,6-di-isopropylphenyl)-[1,1'-biphenyl]-3,4-diamine was prepared analogously to N3-(2-isopropylphenyl)-[1,1'-biphenyl]-3,4-diamine as described above.

Preparation of 1-(2,6-di-isopropylphenyl)-2,6-diphenyl-1H-benzo[d]imidazole

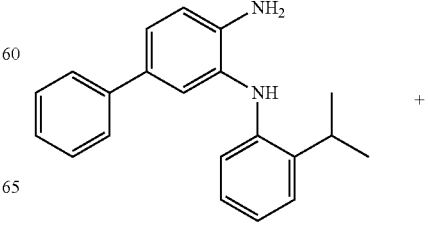

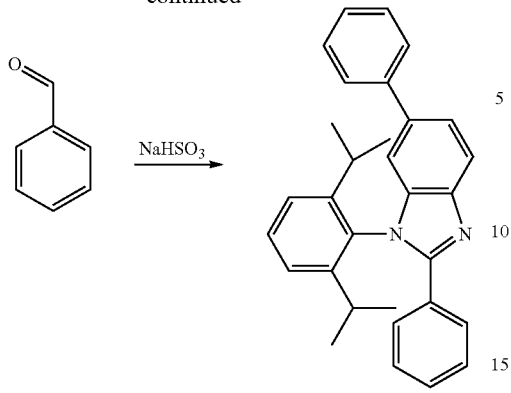

1-(2,6-di-isopropylphenyl)-2,6-diphenyl-1H-benzo[d]imidazole was prepared analogously to 1-(2-isopropylphenyl)-2,6-diphenyl-1H-benzo[d]imidazole as described above.

Synthesis of Compound 2

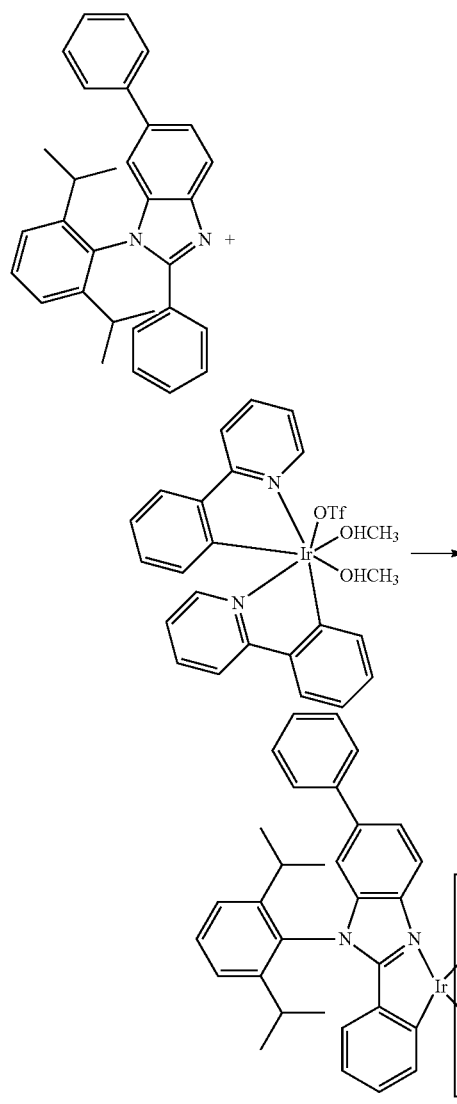

1-(2,6-diisopropylphenyl)-2,6-diphenyl-1H-benzo[d]imidazole (3.0 g, 6.97 mmol) and Iridium complex (1.66 g, 2.32 mmol) were added to a 250 mL round bottom flask. Ethanol (50 mL) was added and the suspension was stirred to reflux for two days. The crude suspension was filtered through Celite®. The cake was washed with methanol and then dissolved in DCM. The crude product was purified by column chromatography. 1.33 grams of Compound 2 was collected.

Synthesis of Compound 3

Preparation of 5-fluoro-2-methyl-4-nitro-1,1'-biphenyl

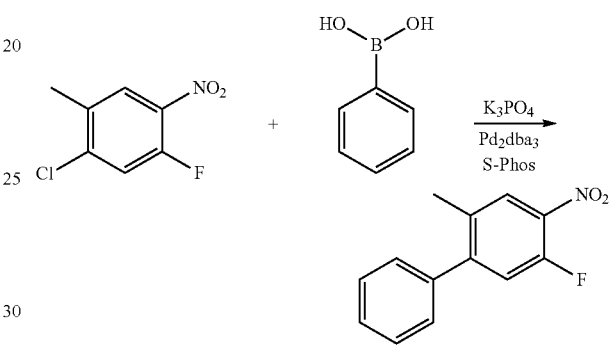

1-chloro-5-fluoro-2-methyl-4-nitrobenzene (20.0 g, 106 mmol), phenylboronic acid (15.44 g, 127 mmol), S-Phos (3.46 g, 8.44 mmol) and potassium phosphate (67.2 g, 317 mmol) were added to a 1 L flask. The reaction mixture was diluted with toluene (400 ml) and water (100 ml). The mixture was degassed for 10 min before addition of Pd$_2$dba$_3$ (1.932 g, 2.110 mmol). The reaction mixture was stirred in an oil bath at 100° C. for 4 hours. Gas chromatography indicated total consumption of starting material. The mixture was then cooled to ambient temperature and filtered through a plug of Celite®. The cake was washed with ethyl acetate. The layers were separated. The product (5-fluoro-2-methyl-4-nitro-1,1'-biphenyl) was purified by column chromatography to give a pale orange solid (22.73 grams, 93%).

Preparation of N-(2-isopropylphenyl)-6-methyl-4-nitro-[1,1'-biphenyl]-3-amine

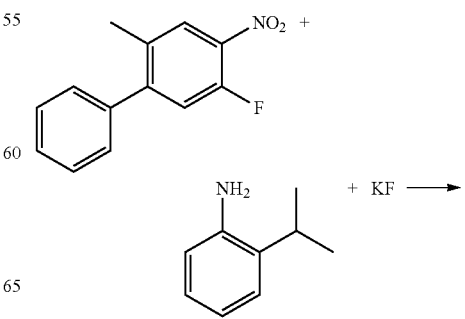

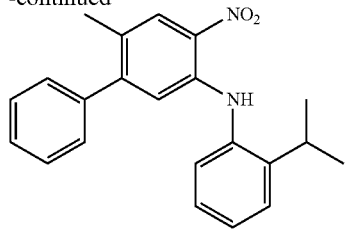

5-fluoro-2-methyl-4-nitro-1,1'-biphenyl (10.0 g, 43.2 mmol), 2-isopropylaniline (18.18 ml, 130 mmol), and potassium fluoride (3.77 g, 64.9 mmol) was added to a 100 mL round bottom flask. The flask was equipped with a condenser and was evacuated and backfilled with nitrogen. The mixture was stirred in an oil bath at 180° C. After 22 hours, the temperature was raised 10 degrees and the mixture was stirred for another 12 hours. The mixture was then diluted with ethyl acetate and washed with saturated sodium bicarbonate. The organic layer was dried and concentrated. This was placed on the Kugelrohr at 155° C. to remove excess aniline. The residue in the flask was triturated in hexane to give 11.0 grams (73.4%) of N-(2-isopropylphenyl)-6-methyl-4-nitro-[1,1'-biphenyl]-3-amine as an orange powder.

Preparation of N3-(2-isopropylphenyl)-6-methyl-[1,1'-biphenyl]-3,4-diamine

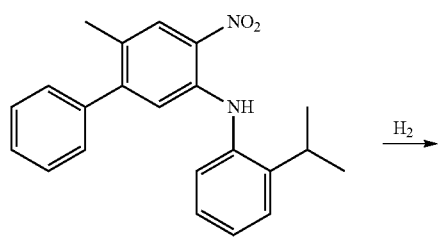

N-(2-isopropylphenyl)-6-methyl-4-nitro-[1,1'-biphenyl]-3-amine (11.0 g, 31.8 mmol) was added to a hydrogenation bottle. Ethanol and Pd/C 10% (3.0 grams) were added. This mixture was hydrogenated at 35 psi for 4 hours. The mixture was filtered through Celite® and evaporated. This was filtered through a plug of silica gel using 10% ethyl acetate in DCM to give 10.0 grams (100%) of desired product, N3-(2-isopropylphenyl)-6-methyl-[1,1'-biphenyl]-3,4-diamine.

Preparation of 1-(2-isopropylphenyl)-5-methyl-2,6-diphenyl-1H-benzo[d]imidazole

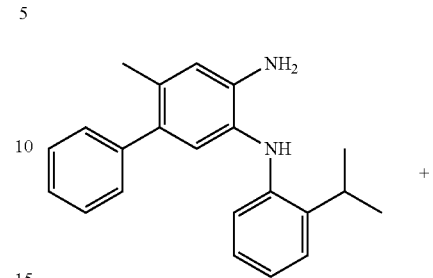

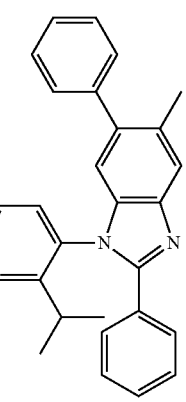

N3-(2-isopropylphenyl)-6-methyl-[1,1'-biphenyl]-3,4-diamine, (10.0 grams, 31.6 mmol), sodium bisulfite (5.92 grams, 56.9 mmol) and benzaldehyde (3.85 mL, 37.9 mmol) and DMF (100 mL) were combined in a 500 mL round bottom flask, which was placed in an oil bath at 125° C. for 18 hours. GCMS showed proper mass and that the reaction was complete. This was diluted with water and ethyl acetate. The organic layer was washed with water and the crude was purified by column chromatography to give 10.68 grams (84%) of 1-(2-isopropylphenyl)-5-methyl-2,6-diphenyl-1H-benzo[d]imidazole product.

Synthesis of Compound 3

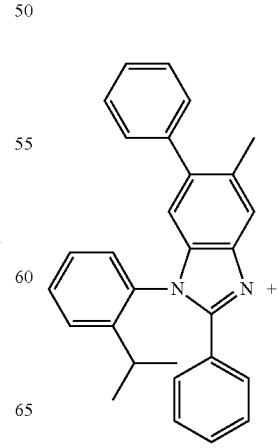

-continued

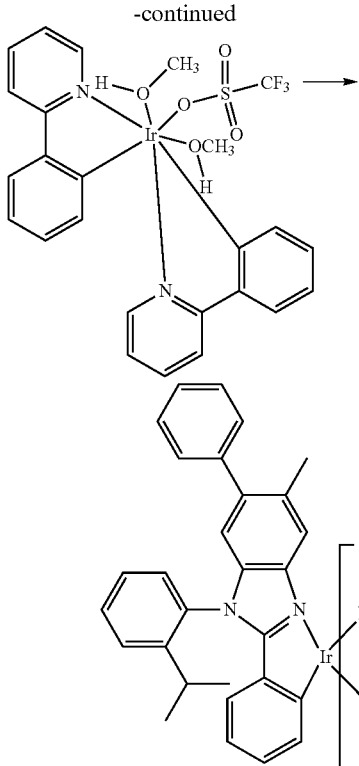

Iridium triflate complex (2.96 g, 4.14 mmol) and 1-(2-isopropylphenyl)-5-methyl-2,6-diphenyl-1H-benzo[d]imidazole (5.0 g, 12.42 mmol) were added to a 250 mL round bottom flask. Ethanol (100 mL) was added. The mixture was refluxed for 26 hours. The mix was filtered through celite. The cake was washed with ethanol and hexane. The funnel was moved to a different filtration flask and the product was extracted with DCM. The filtrate was adsorbed onto Celite® and chromatographed (silica gel). Elution with 1:1 DCM-hexane gave 1.72 grams (46%) of Compound 3.

Synthesis of Compound 4

Preparation of N-(2-isopropylphenyl)-3-nitro-[1,1'-biphenyl]-4-amine

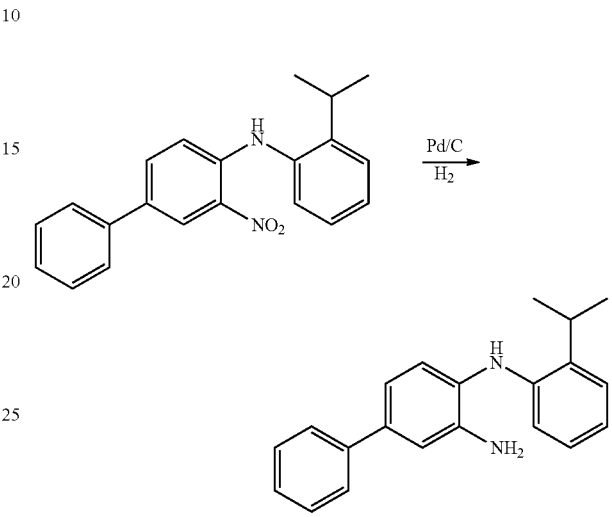

4-fluoro-3-nitro-1,1'-biphenyl (5 g, 23.02 mmol), 2-isopropylaniline (16.30 ml, 115 mmol) and potassium fluoride (2.006 g, 34.5 mmol) were mixed together and heated to 180° C. under nitrogen for 24 h. Dark orange color crude material was diluted with ethyl acetate and filtered through a Celite® plug. Solvents were removed from filtrate under reduced pressure to give an oily mass which was distilled again at a higher temperature to remove residual 2-isopropylaniline and yield 8 g brown colored residue. The residue was triturated with 250 mL hexanes to give 7.5 g N-(2-isopropylphenyl)-3-nitro-[1,1'-biphenyl]-4-amine.

Preparation of N4-(2-isopropylphenyl)-[1,1'-biphenyl]-3,4-diamine

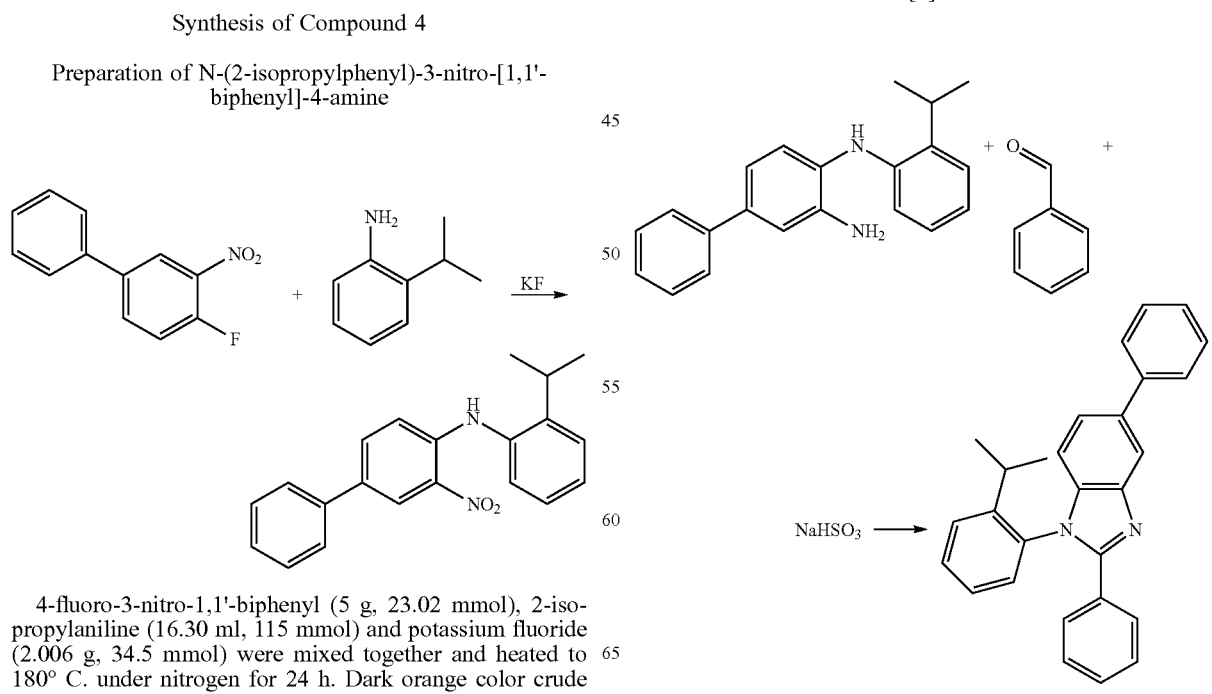

N-(2-isopropylphenyl)-3-nitro-[1,1'-biphenyl]-4-amine (7.5 g, 22.56 mmol) and 10% Pd/Charcoal (0.75 g, 22.56 mmol) were added to a degassed mixture of 200 mL 4:1 ethanol and acetic acid. The mixture was hydrogenated at 50 psi for 3 h and filtered through a Celite® pad. N4-(2-isopropylphenyl)-[1,1'-biphenyl]-3,4-diamine (4.9 g, 72% yield) was isolated after evaporation of the filtrate under reduced pressure.

Preparation of 1-(2-isopropylphenyl)-2,5-diphenyl-1H-benzo[d]imidazole

N4-(2-isopropylphenyl)-[1,1'-biphenyl]-3,4-diamine (4.9 g, 16.20 mmol), benzaldehyde (1.984 ml, 19.44 mmol) and sodium sulfite (3.03 g, 29.2 mmol) were added to 80 mL DMF and heated to 125° C. for 24 h under air. The reaction mixture was filtered through a Celite® pad and the filtrate was distilled under reduced pressure (410 mTorr, 180° C.) to remove DMF and other low boiling components and yield a brown color crude material, which was ca. 95% product. The product was purified by column chromatography using 5-10% ethyl acetate/hexanes as eluent over silica gel. The isolated material was recrystallized from hot hexane and DCM to give 1-(2-isopropylphenyl)-2,5-diphenyl-1H-benzo[d]imidazole (4.05 g, 64% yield) as white crystalline material.

Synthesis of Compound 4

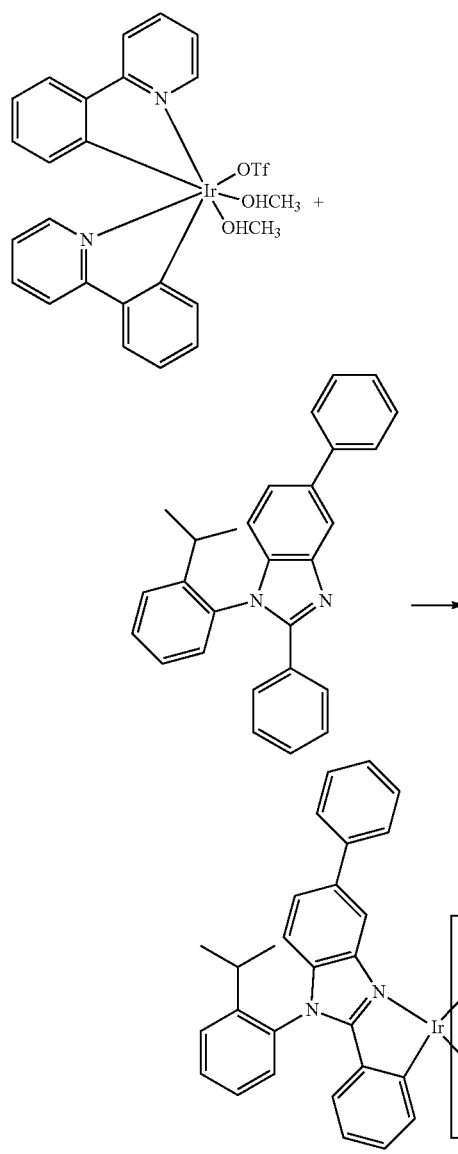

Iridium complex (2.450 g, 3.43 mmol) and 1-(2-isopropylphenyl)-2,5-diphenyl-1H-benzo[d]imidazole (4 g, 10.30 mmol) were added to 125 mL ethanol and degassed for 30 minutes. The reaction mixture was heated to reflux for 24 h. The yellow color reaction mixture was then cooled to room temperature and filtered through a Celite® pad. The precipitates were washed with ethanol followed by hexanes and finally re-dissolved in DCM to give a yellow color solution. Organic solvents were removed under reduced pressure from the combined filtrate to give a yellow color crude compound which was purified by silica gel column chromatography to obtain 0.4 g of Compound 4.

Synthesis of Compound 5

Preparation of N-(2,6-diisopropylphenyl)-3-nitro-[1,1'-biphenyl]-4-amine

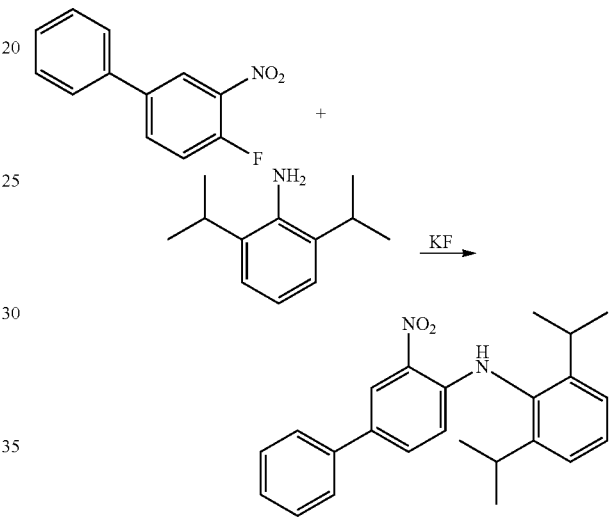

4-fluoro-3-nitro-1,1'-biphenyl (5 g, 23.02 mmol), 2,6-diisopropylaniline (20.41 g, 115 mmol) and potassium fluoride (2.006 g, 34.5 mmol) were heated to 180° C. under nitrogen for 24 h. The dark orange color crude was diluted with ethyl acetate and filtered through a Celite® plug. The filtrate was evaporated to give an oily mass which was distilled under reduced pressure to produce a brown colored residue. The residue was triturated with 250 mL hexanes to give 7.5 g of material. 6 g of N-(2,6-diisopropylphenyl)-3-nitro-[1,1'-biphenyl]-4-amine was isolated from this material after column chromatography using 10% ethyl acetate/hexanes as eluent over silica gel.

Preparation of N4-(2,6-diisopropylphenyl)-[1,1'-biphenyl]-3,4-diamine

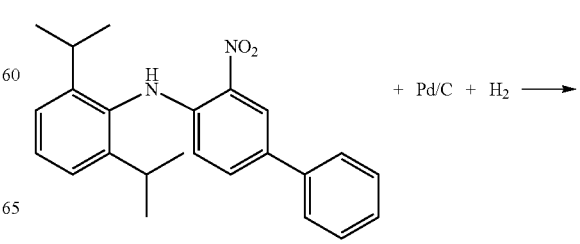

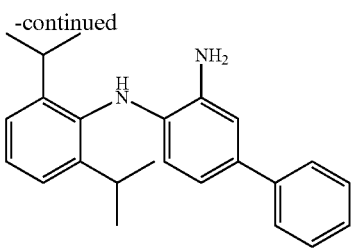

N-(2,6-diisopropylphenyl)-3-nitro-[1,1'-biphenyl]-4-amine (6 g, 16.02 mmol) was hydrogenated with 0.6 g 10% palladium on charcoal in a 9:1 mixture of ethanol and acetic acid for 2 h at 50 psi. The reaction mixture was filtered through a Celite® plug and the filtrate was evaporated under reduced pressure. The isolated material was purified by column chromatography over silica gel using 10% ethyl acetate and hexanes as an eluent over silica gel. A total of 5.3 g (96%) of N4-(2,6-diisopropylphenyl)-[1,1'-biphenyl]-3,4-diamine was obtained.

Preparation of 1-(2,6-diisopropylphenyl)-2,5-diphenyl-1H-benzo[d]imidazole

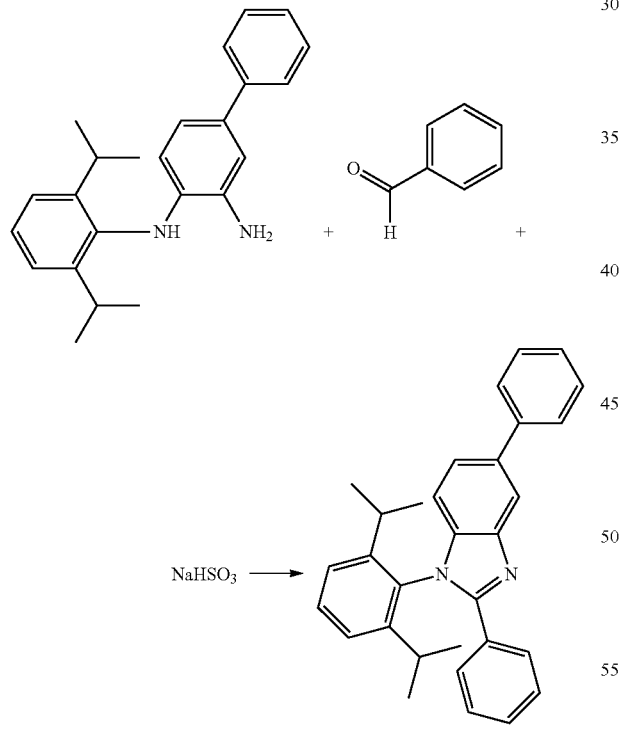

N⁴-(2,6-diisopropylphenyl)-[1,1'-biphenyl]-3,4-diamine (5.3 g, 15.38 mmol), benzaldehyde (1.884 ml, 18.46 mmol) and sodium bisulfite (2.88 g, 27.7 mmol) were added to 80 mL DMF and the mixture was heated to 125° C. for 18 h. The reaction mixture was cooled to room temperature, filtered through a Celite® plug and later distilled (at 520 micron, 170° C.) to give a brown color solid. The solid was re-dissolved in DCM and washed with brine twice and dried over MgSO₄. Solvents were removed under reduced pressure from this material and it was purified by silica gel column chromatography using 5-8% ethyl acetate/hexanes as eluent to give a light brown color material. This material was recrystallized from hexanes and DCM to give 6.0 g of 1-(2,6-diisopropylphenyl)-2,5-diphenyl-1H-benzo[d]imidazole as colorless crystals Synthesis of Compound 5

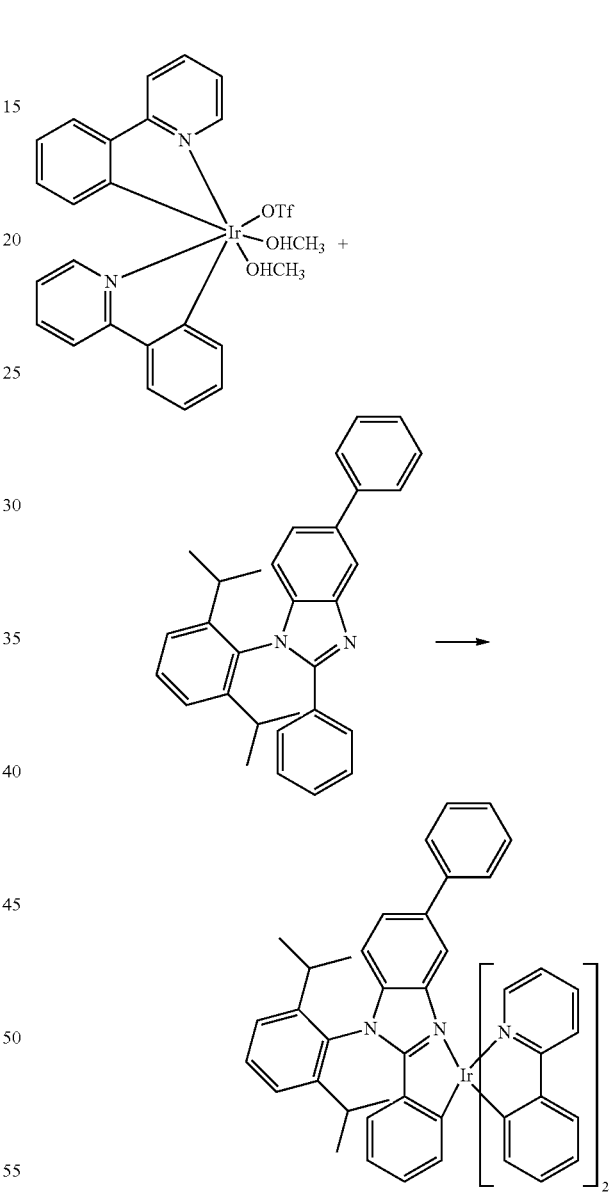

Iridium triflate complex (1.658 g, 2.322 mmol) and 1-(2,6-diisopropylphenyl)-2,5-diphenyl-1H-benzo[d]imidazole (3 g, 6.97 mmol) were added to 80 mL ethanol and degassed for 30 minutes. The mixture was refluxed under nitrogen gas for 24 h. The reaction mixture was filtered through a Celite® plug. The precipitates were re-dissolved in DCM and organic solvents were removed from this solution under reduced pressure to give a yellow color solid. The solid was purified by column chromatography over silica gel to give 0.6 g of Compound 5.

Synthesis of Compound 6

Preparation of N-(2-ethylphenyl)-3-nitro-[1,1'-biphenyl]-4-amine

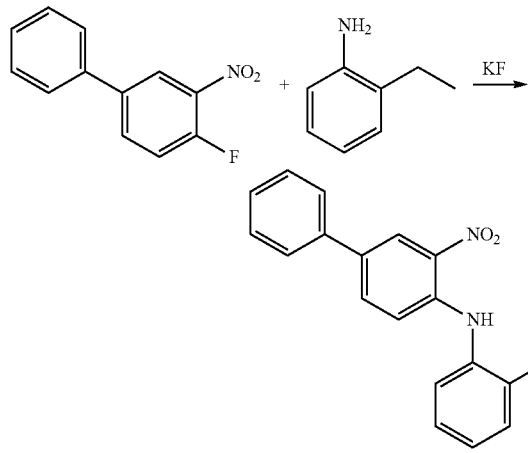

4-fluoro-3-nitro-1,1'-biphenyl (14.7 g, 67.7 mmol), potassium fluoride (5.90 g, 102 mmol) and 2-ethylaniline (41.7 ml, 338 mmol) were combined in a 250 ml single neck round bottom flask and attached condenser. The system was evacuated and purged with nitrogen twice and then the reaction mixture was heated under nitrogen in an oil bath set at 200° C. overnight. The reaction mixture was cooled then diluted with dichloromethane. The precipitate was filtered off with filter paper and washed with dichloromethane. The solution was concentrated down, then the unreacted ethyl aniline was removed by Kugelrohr set at 150° C. to get 21.7 g of a crude oil. The crude sample was loaded onto a silica gel column and was purified using 97/3 hexane/ethyl acetate solvent system. Fractions containing only the desired product were evaporated to get 13.8 g of red oil for a 64% yield.

Preparation of N4-(2-ethylphenyl)-[1,1'-biphenyl]-3,4-diamine

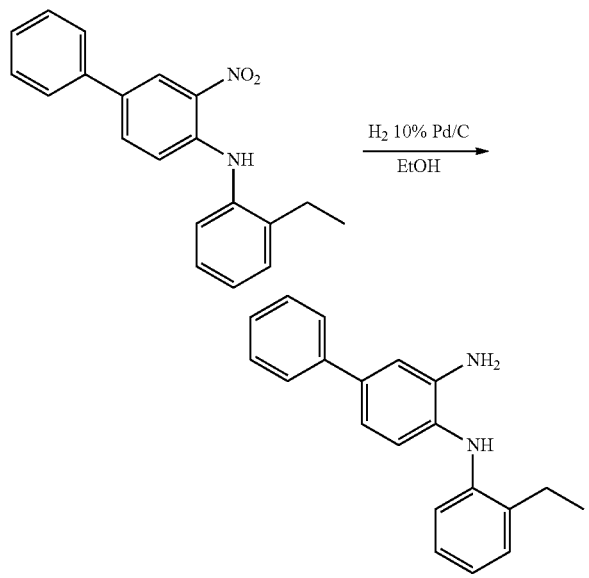

10% Palladium on carbon (2.306 g, 2.167 mmol) was added to a 500 ml hydrogenation bottle and placed under nitrogen. 200 ml ethanol was used to transfer N-(2-ethylphenyl)-3-nitro-[1,1'-biphenyl]-4-amine (13.8 g, 43.3 mmol) to the hydrogenation bottle. The reaction was filtered through Celite® using dichloromethane. The solvent was evaporated to give 11.7 g of a light orange solid. The solid was dissolved in 30 ml DCM and loaded onto a silica gel column then purified using 90/10 then 85/15 hexane/ethyl acetate. Fractions containing the desired product were combined and evaporated in vacuo to get 10.1 g of a purple solid for an 81% yield.

Preparation of 1-(2-ethylphenyl)-2,5-diphenyl-1H-benzo[d]imidazole

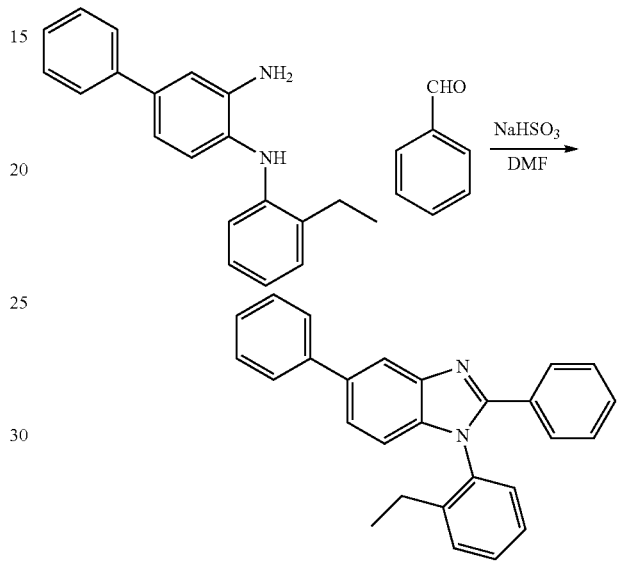

$N^4$-(2-ethylphenyl)-[1,1'-biphenyl]-3,4-diamine (5.0 g, 17.34 mmol) was dissolved in 85 ml DMF in a 250 ml single neck round bottom flask. Sodium bisulfite (2.71 g, 26.0 mmol) then benzaldehyde (3.16 ml, 31.2 mmol) were added to the reaction mixture. A condenser was attached and the system was evacuated and purged with nitrogen twice. The reaction was heated overnight in an oil bath set at 125° C. The reaction was poured into 400 mL water to get a pink milky suspension then extracted twice with ethyl acetate. The combined organic portions were washed twice with brine. The solution was dried with sodium sulfate, filtered, and evaporated to give 9.1 g of dark red oil. The red oil was purified to give 6.0 g of red solid for a 92% yield.

Synthesis of Compound 6

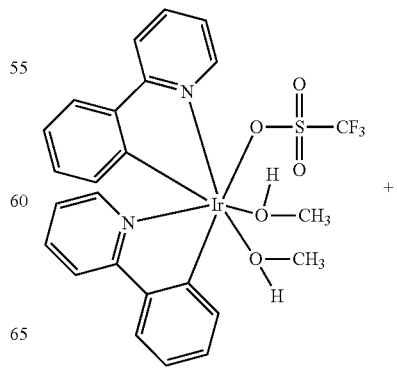

119
-continued

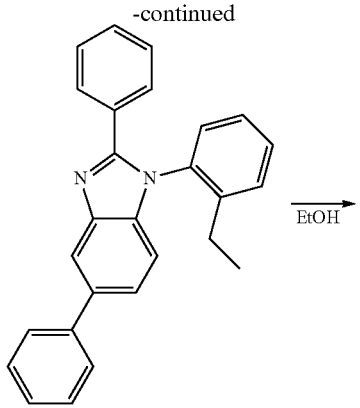

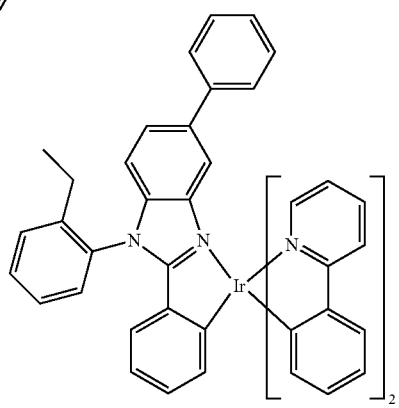

1-(2-ethylphenyl)-2,5-diphenyl-1H-benzo[d]imidazole (2.99 g, 7.99 mmol) and iridium complex (1.9 g, 2.66 mmol) were dissolved in 70 mL ethanol in a 250 mL single neck round bottom flask. A condenser was attached then the system was evacuated and purged with nitrogen three times. The brown solution was heated to a vigorous reflux in an oil bath overnight. Celite® was added to the cooled reaction and filtered through Celite® in a sintered filter funnel. The Celite® was washed well with ethanol (400 ml). The Celite® was then washed with dichloromethane. The dichloromethane solution was evaporated to yield 1.9 g of a yellow solid. The crude sample was absorbed on Celite® and purified on a silica gel column using 50-75% DCM in hexane solvent system. The fractions containing the product were combined and evaporated to get 0.90 of Compound 6.

Synthesis of Compound 7

Preparation of N-(2,6-diethylphenyl)-3-nitro-[1,1'-biphenyl]-4-amine

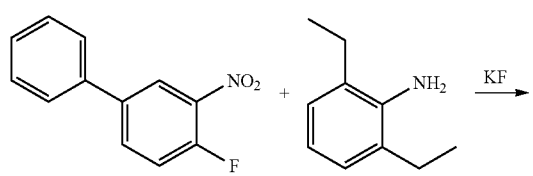

120
-continued

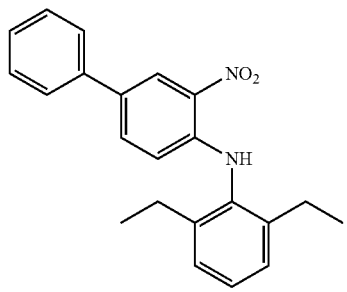

4-fluoro-3-nitro-1,1'-biphenyl (6.5 g, 29.9 mmol) and potassium fluoride (2.61 g, 44.9 mmol) were added to a 250 mL round bottom flask. Next, 2,6-diethylaniline (19.72 ml, 120 mmol) was added and the flask was evacuated and backfilled with nitrogen. The flask was stirred in an oil bath at 200° C. for 24 h. The reaction mixture was cooled and diluted with DCM. The resulting mixture was filtered and concentrated on a rotovap. Next the flask was placed on the Kugelrohr and heated to 155° C. The residue was chromatographed on a silica gel column and eluted with 5% ethyl acetate in hexane to get 6.36 grams (61%) of orange solid.

Preparation of N4-(2,6-diethylphenyl)-[1,1'-biphenyl]-3,4-diamine

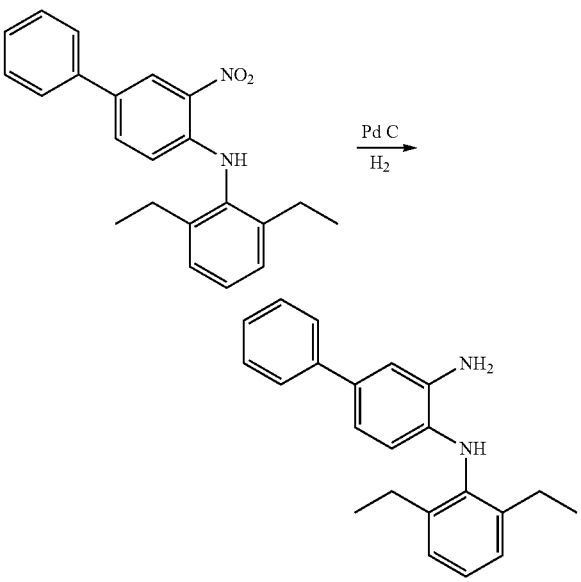

N-(2,6-diethylphenyl)-3-nitro-[1,1'-biphenyl]-4-amine (6.3 g, 18.19 mmol) was added to a hydrogenation bottle. Ethyl acetate (200 mL) was added. The mixture was hydrogenated at 40 psi for 2 h. The mixture was then filtered. The product was chromatographed on a 150 gram column which was eluted with 10-15% ethyl acetate in hexane to give the product 5.1 grams (81%), which was a purple oil.

121

Preparation of 1-(2,6-diethylphenyl)-2,5-diphenyl-1H-benzo[d]imidazole

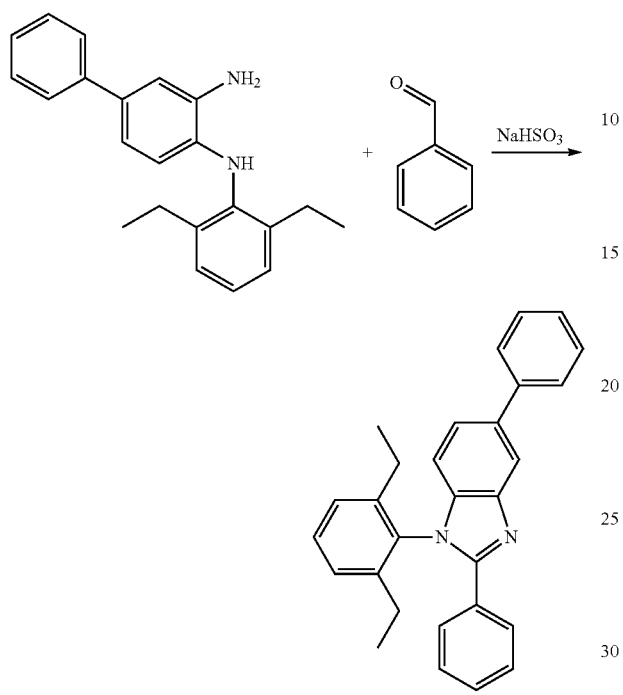

N⁴-(2,6-diethylphenyl)-[1,1'-biphenyl]-3,4-diamine (5.06 g, 15.99 mmol) and benzaldehyde (1.958 ml, 19.19 mmol) were added to a 500 mL round bottom flask. The reaction mixture was diluted with DMF (100 mL). Sodium bisulfite (3.00 g, 28.8 mmol) was added and the mixture was stirred in an oil bath at 125° C. for 20 h. This was diluted with water and ethyl acetate. The organic layer was separated and washed with brine. The crude was chromatographed on a 150 gram column eluted with 10-15% ethyl acetate in hexane. 4.74 grams (74%) of a 1-(2,6-diethylphenyl)-2,5-diphenyl-1H-benzo[d]imidazole in the form of a pale green foam was obtained.

Synthesis of Compound 7

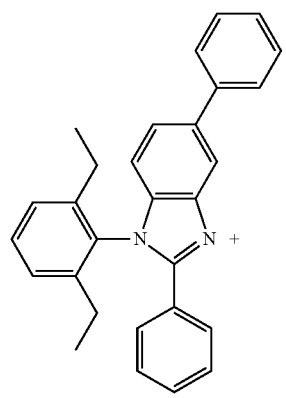

122

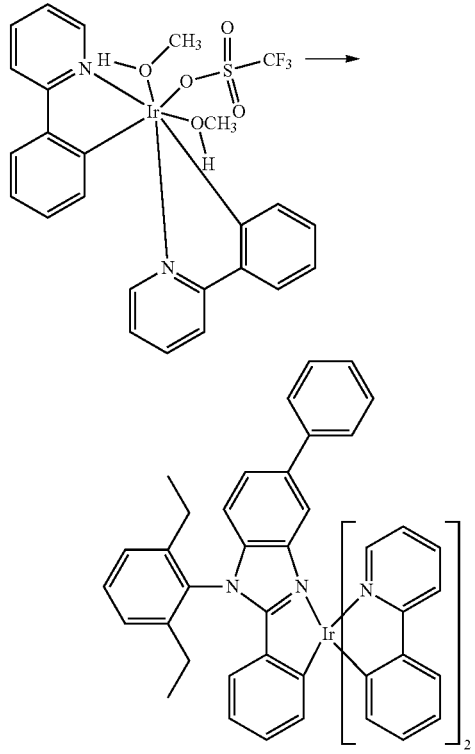

Iridium triflate complex (2.78 g, 3.89 mmol) and 1-(2,6-diethylphenyl)-2,5-diphenyl-1H-benzo[d]imidazole (4.7 g, 11.68 mmol) were added to a 500 mL round bottom flask. Ethanol was added and the mixture was stirred at reflux for 22 h. The mixture was filtered through Celite® and the cake was washed first with ethanol and hexane, then the funnel was moved to a second filter flask and the product was extracted with DCM. The filtrate was evaporated. The product was chromatographed on a silica gel column which was eluted with 1:1 hexane-DCM. 2.1 grams of Compound 7 product was obtained.

Synthesis of Compound 8

Preparation of 2-fluoro-3-nitro-1,1'-biphenyl

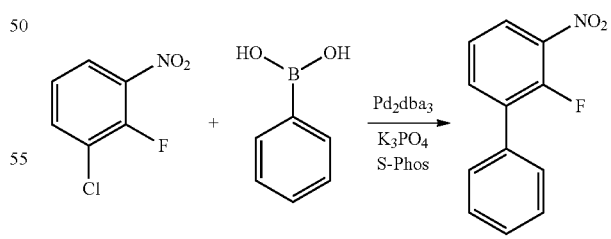

1-chloro-2-fluoro-3-nitrobenzene (15 g, 85 mmol), phenylboronic acid (20.84 g, 171 mmol) and potassium phosphate monohydrate (59.0 g, 256 mmol) were added to 600 mL 9:1 mixture of toluene and water. Reaction mixture was degassed for 20 minutes by bubbling nitrogen gas and tris(dibenzylideneacetone)dipalladium(0) (0.782 g, 0.854 mmol) was added. Degassing continued for another 10 minutes and the reaction mixture was heated to reflux for 18 h. It was cooled to room temperature and poured over brine. The organic materials were extracted with ethyl acetate from the brine. Extracts were combined and dried over MgSO$_4$. Solvents were removed under reduced pressure and the crude thus obtained was purified by column chromatography over silica gel using 1-15% DCM/hexanes. 2-fluoro-3-nitro-1,1'-biphenyl (12.52 g, 57.6 mmol, 67.5% yield) was isolated a as light yellow colored oil.

Preparation of 3-nitro-N-phenyl-[1,1'-biphenyl]-2-amine

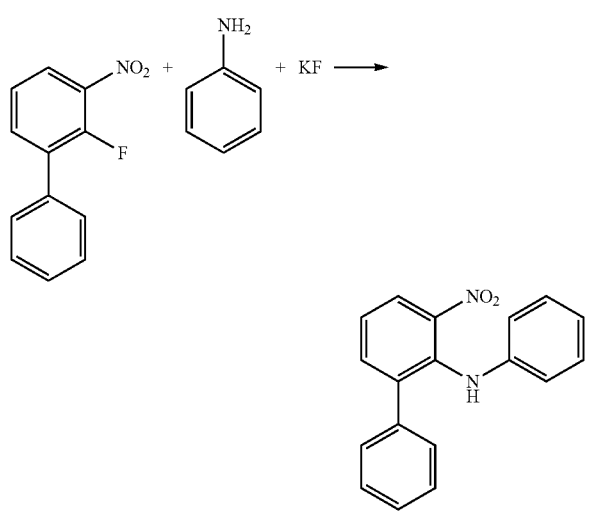

2-fluoro-3-nitro-1,1'-biphenyl (6 g, 27.6 mmol), aniline (12.86 g, 138 mmol) and potassium fluoride (3.21 g, 55.2 mmol) were heated to 180° C. for 18 h. The crude reaction mixture was diluted with ethyl acetate, filtered thru a Celite® pad and washed with brine. 3-nitro-N-phenyl-[1,1'-biphenyl]-2-amine (8 g, 27.6 mmol, 100% yield) was isolated from the crude material after removal of aniline by vacuum distillation.

Preparation of N2-phenyl-[1,1'-biphenyl]-2,3-diamine

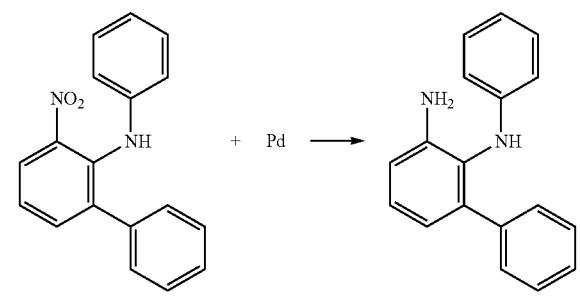

3-nitro-N-phenyl-[1,1'-biphenyl]-2-amine (8 g, 27.6 mmol) and 10% palladium on charcoal (0.8 g, 7.52 mmol) were added to 200 mL of an ethanol and acetic acid mixture (9:1) and hydrogenated at 50 psi. After filtration through a Celite® pad, the crude material was concentrated under reduced pressure and purified by column chromatography over silica gel using 1:1 DCM/hexanes followed by 1:9:10 ethylacetate/DCM/hexanes mixture. N2-phenyl-[1,1'-biphenyl]-2,3-diamine (7.19 g, 99% yield) was isolated as colorless oil.

Preparation of 1,2,7-triphenyl-1H-benzo[d]imidazole

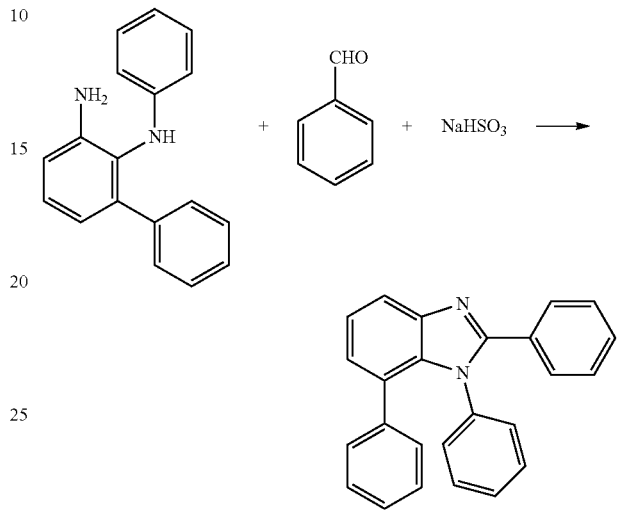

N$^2$-phenyl-[1,1'-biphenyl]-2,3-diamine (7.1 g, 27.3 mmol), benzaldehyde (2.89 g, 27.3 mmol) and sodium bisulfite (2.84 g, 27.3 mmol) were added to 130 mL DMF and heated to 125° C. for 12 h. Reaction mixture was cooled to room temperature and poured over 300 mL 5% LiCl solution. Precipitated material was filtered out and dried in a vacuum oven. Dried material was purified by column chromatography over silica gel using 5-10% ethyl acetate/DCM as eluent to give 1,2,7-triphenyl-1H-benzo[d]imidazole (8.02 g, 23.15 mmol, 85% yield) as a colorless solid.

Synthesis of Compound 8

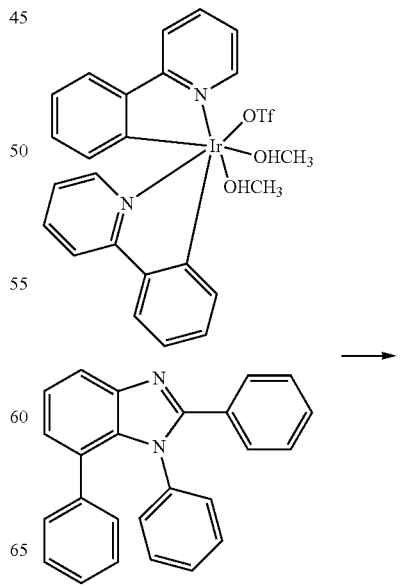

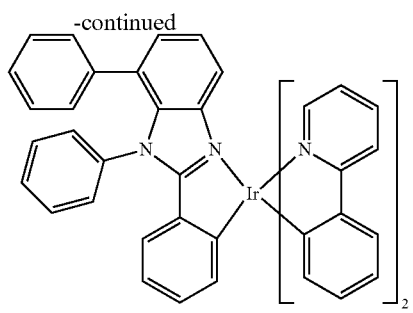

Iridium complex (1.717 g, 2.406 mmol) and 1,2,7-triphenyl-1H-benzo[d]imidazole (2.5 g, 7.22 mmol) were added to 80 mL ethanol and the reaction mixture was degassed for 30 minutes. It was refluxed for 48 h under inert environment. The reaction mixture was filtered through a celite) plug. The precipitates were collected and purified by column chromatography to give 0.29 g of Compound 8.

Synthesis of Compound 9

Preparation of N-(2-isopropylphenyl)-3-nitro-[1,1'-biphenyl]-2-amine

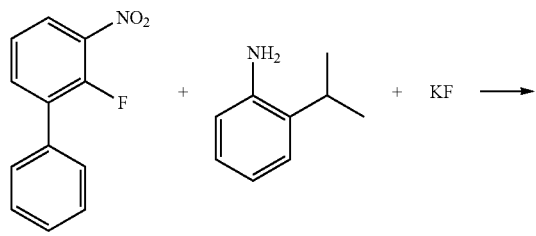

2-fluoro-3-nitro-1,1'-biphenyl (6 g, 27.6 mmol), 2-isopropylaniline (19.56 ml, 138 mmol) and potassium fluoride (3.21 g, 55.2 mmol) were heated to 180° C. for 18 h. The crude material was diluted with ethyl acetate, filtered through a Celite® pad and washed with brine. The organic layer was dried over MgSO$_4$ and solvents were removed under reduced pressure. The crude product was purified by vacuum distillation. N-(2-isopropylphenyl)-3-nitro-[1,1'-biphenyl]-2-amine (8.04 g, 88% yield) was obtained and used in the next step without further purification.

Preparation of N$^2$-(2-iospropylphenyl)-[1,1'-biphenyl]-2,3-diamine

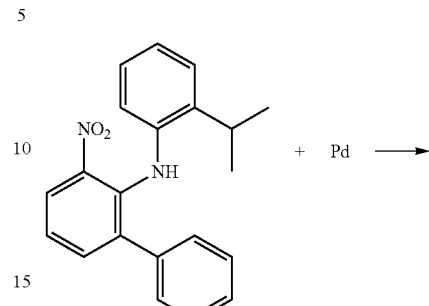

A mixture of N-(2-isopropylphenyl)-3-nitro-[1,1'-biphenyl]-2-amine (8.04 g, 24.19 mmol) and 10% palladium on charcoal (0.804 g, 7.55 mmol) was hydrogenated at 50 psi for 1 h. The reaction mixture was filtered through a Celite® plug. Organic solvents were removed from the filtrate under reduced pressure and crude N$^2$-(2-isopropylphenyl)-[1,1'-biphenyl]-2,3-diamine (6.42 g, 88% yield) material was used for the next step without further purification.

Preparation of 1-(2-isopropylphenyl)-2,7-diphenyl-1H-benzo[d]imidazole

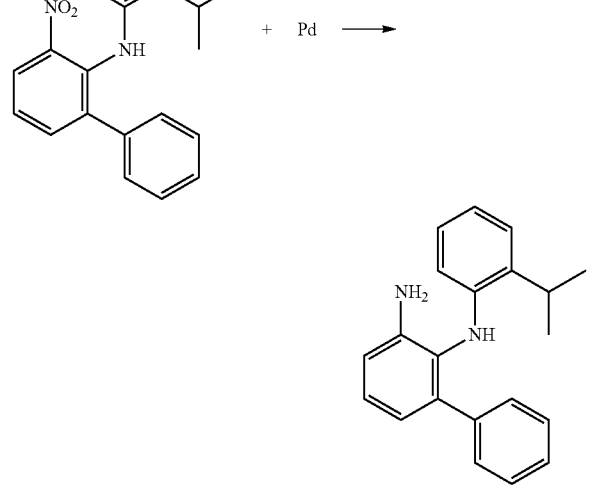

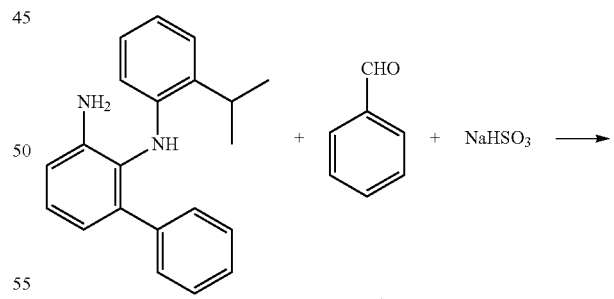

N$^2$-(2-isopropylphenyl)-[1,1'-biphenyl]-2,3-diamine (6.42 g, 21.23 mmol), benzaldehyde (4.06 g, 38.2 mmol) and sodium bisulfite (3.31 g, 31.8 mmol) were added to 105 mL DMF and heated at 125° C. for 12 h. The reaction mixture was cooled to room temperature and poured over 5% LiCl solution. The precipitated material was filtered out and dried in a vacuum oven. The dried material was chromatographed over silica gel using 5-10% ethyl acetate/DCM as eluent to give 1-(2-isopropylphenyl)-2,7-diphenyl-1H-benzo[d]imidazole (4.04 g, 10.40 mmol, 49.0% yield).

Synthesis of Compound 9

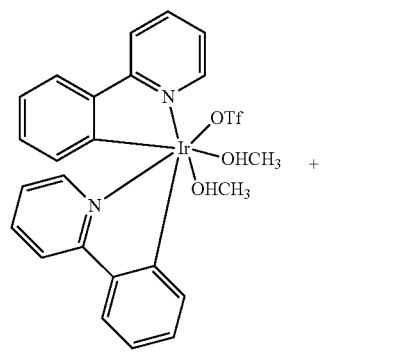

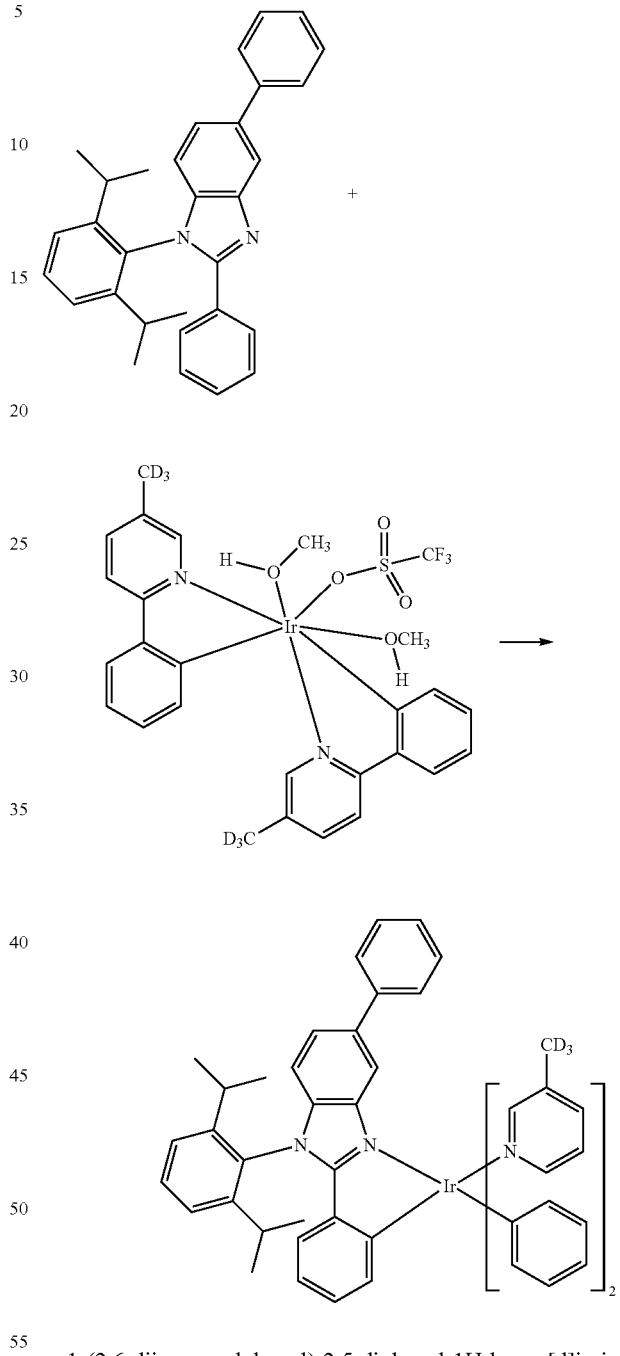

Synthesis of Compound 10

Iridium complex (1.837 g, 2.57 mmol) and 1-(2-isopropylphenyl)-2,7-diphenyl-1H-benzo[d]imidazole (3 g, 7.72 mmol) were added to 90 mL ethanol and degassed with bubbled nitrogen gas. The mixture was refluxed under nitrogen gas for 48 h then filtered through a Celite® plug. The precipitates were collected and purified by column chromatography using 7:3 DCM/hexanes as eluent. This material was further sublimed to give 0.5 g of Compound 9.

1-(2,6-diisopropylphenyl)-2,5-diphenyl-1H-benzo[d]imidazole (3.1 g, 7.20 mmol) and Iridium complex (1.80 g, 2.40 mmol) were added to a 250 mL round bottom flask. The reaction mixture was diluted with ethanol (100 ml) and then stirred at reflux for 26 H. The suspension was filtered through celite and the cake was washed first with ethanol and hexane and then with DCM. The product was chromatographed (silica gel). Using a mobile phase consisting of 1:1 DCM-hexane afforded 1.2 grams (52%) of Compound 10.

129

Synthesis of Compound II

Preparation of d$_7$-isopropyl zinc bromide

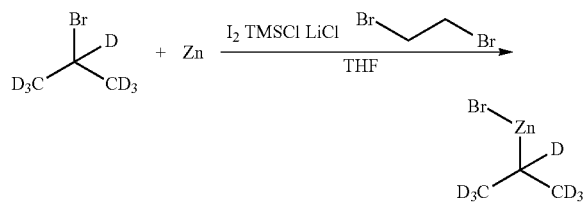

Zinc (10.06 g, 154 mmol) and lithium chloride (6.52 g, 154 mmol) were added to a 250 ml three neck round bottom flask. Septums were placed in the outside necks of the flask. The system was evacuated while heating with a heat gun to remove moisture then cooled. A condenser was attached, then the system was evacuated and placed under nitrogen. 80 ml anhydrous THF, and then 1,2-dibromoethane (0.199 ml, 2.307 mmol) were added via syringe through a septum. The reaction vessel was placed in an oil bath preheated to 60° C. for 20 min.

The reaction vessel was removed from the oil bath and allowed to cool to room temperature for 20 min. Chlorotrimethylsilane (0.769 ml, 0.769 mmol), then iodine (0.098 g, 0.385 mmol) dissolved in 0.5 ml THF were added to the reaction via syringe through a septum. The reaction vessel was placed back in the oil bath set at 60° C. for 20 min.

The reaction vessel was removed from the oil bath and allowed to cool to room temperature for 20 min. d7-isopropyl bromide (10 g, 77 mmol) was added directly via syringe through the septum. The reaction vessel was placed back in the oil bath now set at 50° C. overnight.

The reaction was removed from the oil bath and stopped the stirring. The prepared reagent was syringed directly from the flask and used as is for the next reaction.

Preparation of 2-d7-isopropylaniline

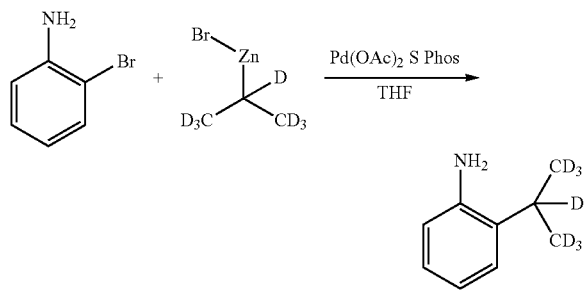

2-bromoaniline (8.0 g, 46.5 mmol), palladium(II) acetate (0.522 g, 2.325 mmol), and dicyclohexyl(2',6'-dimethoxy-[1,1'-biphenyl]-2-yl)phosphine (S Phos) (1.909 g, 4.65 mmol) were added to a 500 ml three neck round bottom flask. The system was evacuated and nitrogen added. 80 ml anhydrous THF was added via syringe then the reaction was cooled in an ice bath. The d7-isopropyl zinc bromide (15.18 g, 78 mmol) was transferred via syringe to the reaction. After the transfer was complete, the ice bath was removed and the reaction was stirred at room temperature overnight. The reaction was transferred to a separatory funnel with ethyl acetate and ammonium chloride solution. The aqueous portion was extracted twice with ethyl acetate. The combined organic portions were washed once with saturated brine solution, dried with sodium sulfate, filtered and evaporated to 8.8 g of crude brown oil. The crude was chromatographed using silica gel. The sample was purified using 95/5 then 90/10 hexane/ethyl acetate solvent systems, which gave complete separation of the desired product from impurities. The desired fractions were combined and evaporated in vacuo to produce 2.55 g of a brown oil for a 38.5% yield.

Preparation of 4-chloro-N-(2-d7-isopropylphenyl)-2-nitroaniline

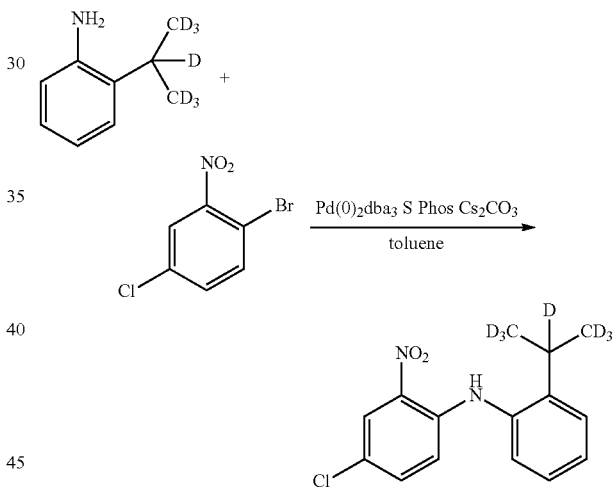

2-(d7-isopropyl) aniline (2.5 g, 17.57 mmol) and 1-bromo-4-chloro-2-nitrobenzene (4.16 g, 17.57 mmol) were dissolved in 80 ml toluene in a 250 ml three neck round bottom flask and an attached condenser. The solution was degassed for 20 min, then Cesium carbonate (8.59 g, 26.4 mmol), Pd(O)$_2$ dba$_3$ (0.322 g, 0.351 mmol), and dicyclohexyl(2',6'-dimethoxy-[1,1'-biphenyl]-2-yl)phosphine (S Phos) (0.577 g, 1.406 mmol) were each added in that order. The reaction mixture was heated to reflux overnight. The reaction mixture was transferred to a separatory funnel with ethyl acetate and ammonium chloride solution. The aqueous portion was extracted with ethyl acetate twice. The combined organic portions were washed once with saturated brine solution, dried with sodium sulfate, filtered and evaporated to yield 8.2 g of crude brown oil. The sample was then purified using column chromatography (silica gel) with a mobile phase consisting of 97.5/2.5 hexane/ethyl acetate solvent system. The desired product fractions were combined and evaporated to produce 3.1 g of 4-chloro-N-(2-d7-isopropylphenyl)-2-nitroaniline in the form of a red oil for a 59.2% yield.

Preparation of 4-chloro-N1-(2-d7-isopropylphenyl) benzene-1,2-diamine

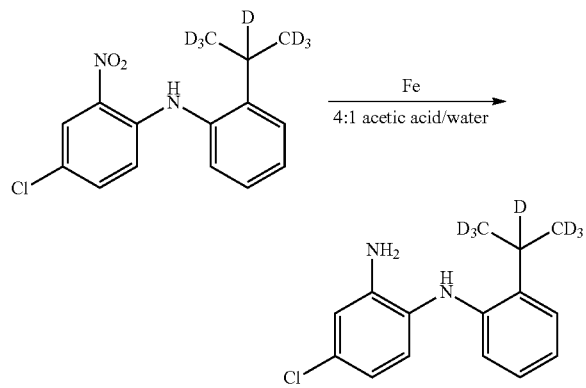

4-chloro-N-(2-d7-isopropylphenyl)-2-nitroaniline (3.0 g, 10.07 mmol) was dissolved in 50 ml acetic acid in a 250 ml three neck round bottom flask. 13 mL of water was added to get a suspension. 1 gram of iron was added every thirty minutes three times.

After three hours, the reaction mixture was filtered through celite to remove the iron, washed with water and then dichloromethane. The two phases were evaporated to get a wet, light brown solid. Water was added to the sample then sodium carbonate was added in portions with vigorous stirring until gas evolution ceased and the aqueous portion was basic. The mixture was transferred to a separatory funnel with ethyl acetate. The aqueous portion was a gray emulsion so the mixture was filtered through Celite® and washed well with ethyl acetate. The aqueous portion was partitioned off then further extracted with ethyl acetate twice. The combined organic portions were washed with brine solution twice, dried with sodium sulfate, filtered and evaporated in vacuo to afford 2.7 g of beige solid for a complete recovery of the desired 4-chloro-N1-(2-d7-isopropylphenyl)benzene-1,2-diamine product (100% yield).

Preparation of 5-chloro-1-(2-d7-isopropylphenyl)-2-phenyl-1H-benzo[d]imidazole

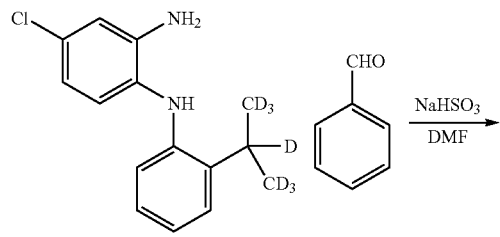

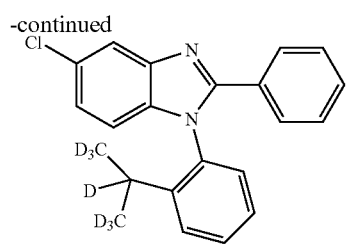

4-chloro-N1-(2-d7-isopropylphenyl)benzene-1,2-diamine (2.7 g, 10.08 mmol) was dissolved in 50 mL DMF in a 250 ml single neck round bottom flask. Sodium bisulfite (1.574 g, 15.12 mmol) then benzaldehyde (1.839 ml, 18.15 mmol) were added to the reaction. A condenser was attached, then the system was evacuated and purged with nitrogen twice. The reaction was heated overnight in an oil bath set at 125° C. The volume of the reaction was concentrated in vacuo then transferred to a separatory funnel with ethyl acetate and water. The aqueous was extracted with ethyl acetate three times. The combined ethyl acetate portions were washed with brine solution three times, dried with sodium sulfate, filtered then evaporated to yield 3.7 g of a brown solid.

The crude sample was then purified using silica gel column chromatography. The mobile phase consisted of 50/48/2 hexane/dichloromethane/ethyl acetate solvent system which gave complete separation from impurities. The desired fractions were combined and evaporated to get 3.25 g of a 5-chloro-1-(2-d7-isopropylphenyl)-2-phenyl-1H-benzo[d]imidazole in the form of a beige solid for a 91% yield.

Preparation of 1-(2-d7-isopropylphenyl)-2,5-diphenyl-1H-benzo[d]imidazole

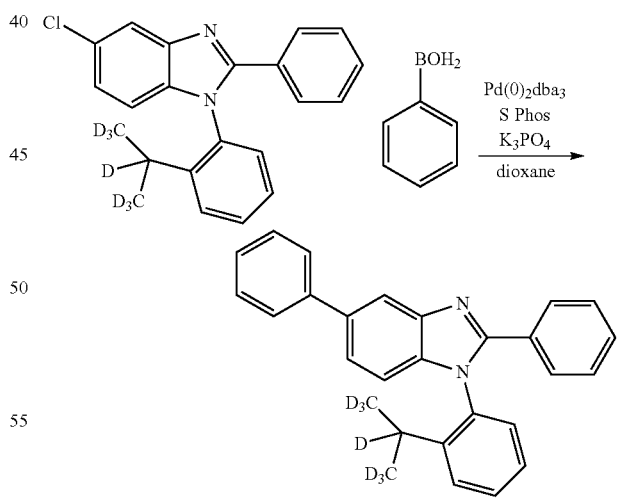

5-chloro-1-(2-d7-isopropylphenyl)-2-phenyl-1H-benzo [d]imidazole (3.0 g, 8.48 mmol) was dissolved in 100 ml dioxane in a 250 ml three neck round bottom flask, then nitrogen was purged directly into the solution for 20 min. Pd(O)$_2$ dba$_3$ (0.155 g, 0.170 mmol), dicyclohexyl(2',6'-dimethoxy-[1,1'-biphenyl]-2-yl)phosphine (S Phos) (0.278 g, 0.678 mmol), phenylboronic acid (1.550 g, 12.72 mmol), and potassium phosphate tribasic (5.40 g, 25.4 mmol) were added to the reaction mixture. The reaction mixture was heated to reflux for nine hours then cooled overnight.

GC/MS indicated the reaction was essentially complete. The reaction mixture was transferred to a separatory funnel with ethyl acetate and water. There was some black insoluble precipitate so some brine solution was added to help phase separation. The aqueous portion was extracted with ethyl acetate three times. The combined organic portions were washed with brine solution once, dried with sodium sulfate, filtered and evaporated to give 5 g of brown oil. The sample was chromatographed (silica gel) and purified with 85/15 hexane/ethyl acetate solvent system to get complete separation of the desired product from impurities. The desired fractions were combined evaporated to 3.24 g of 1-(2-d7-isopropylphenyl)-2,5-diphenyl-1H-benzo[d]imidazole in the form of a white solid for a 96.6% yield.

Synthesis of Compound 11

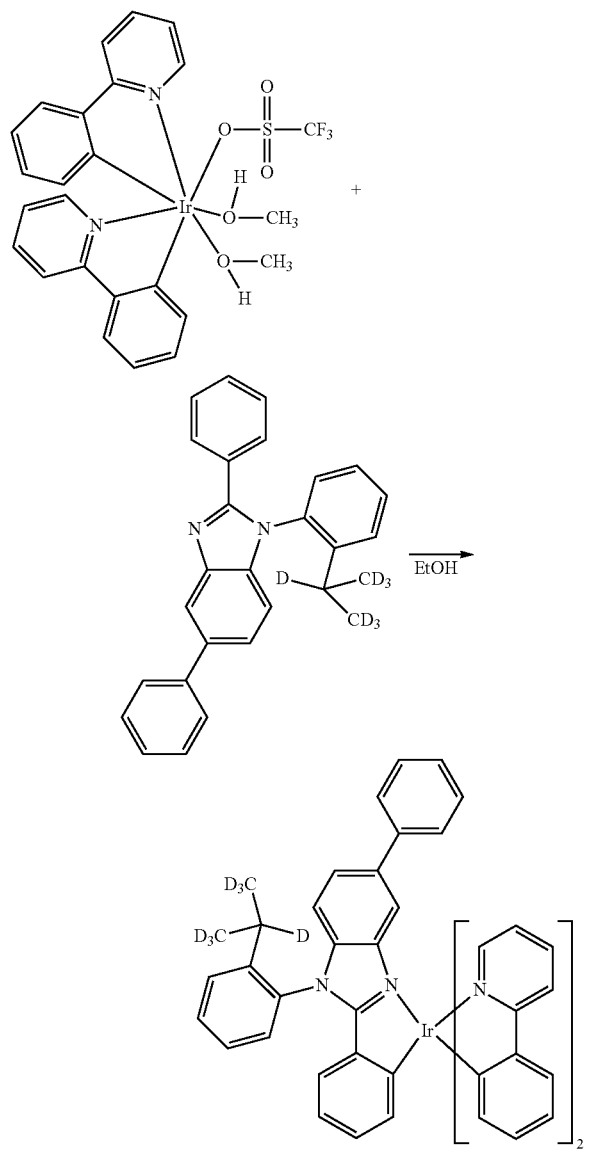

1-(2-d7-isopropylphenyl)-2,5-diphenyl-1H-benzo[d]imidazole (3.41 g, 8.62 mmol), Iridium complex (2.05 g, 2.87 mmol) and 70 ml ethanol were added to a 250 ml single neck round bottom flask. A condenser was attached, then the system was evacuated and purged with nitrogen three times. The brown solution was heated to a vigorous reflux in an oil bath for two days then cooled to room temperature. Celite® was added to the reaction and this was then filtered through Celite®. The Celite® was washed well with ethanol. The celite was next washed with dichloromethane then evaporated to recover 2.1 g of a yellow precipitate.

The crude sample was adsorbed on to 40 g celite and purified on a silica gel column eluted with 50/50 then 25/75 hexane/dichloromethane solvent system. This gave fractions which were combined and rotovaped down to get 1.13 g of compound 11 in the form of a yellow solid.

Device Examples

All example devices were fabricated by high vacuum (<10$^{-7}$ Torr) thermal evaporation. The anode electrode was 1200 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of the device examples consisted of sequentially, from the ITO surface, 100 Å of Compound B as the hole injection layer (HIL), 300 Å of 4,4'-bis[N-(1-naphthyl)-N-phenylamino]biphenyl (α-NPD) as the hole transporting layer (HTL), 300 Å of the compound of Formula I doped in with Compound C as host, with 10-15 wt % of the iridium phosphorescent compound as the emissive layer (EML), 50 Å of Compound C as a blocking layer (BL), 450 Å of Alq (tris-8-hydroxyquinoline aluminum) as the ETL. The comparative Example with Compound A was fabricated similarly to the Device Examples except that Compound A was used as the emitter in the EML.

The device results and data are summarized in Tables 2 and 3 from those devices. As used herein, NPD, Alq, Compound A, Compound B and Compound C have the following structures:

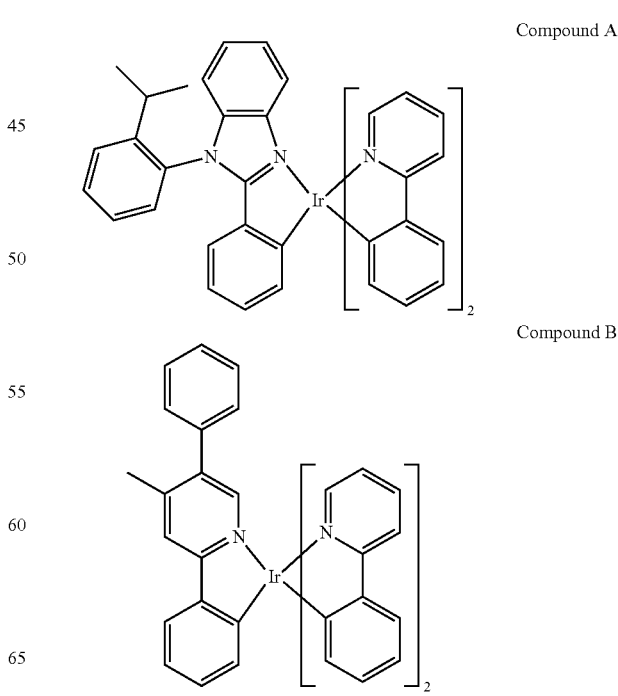

-continued

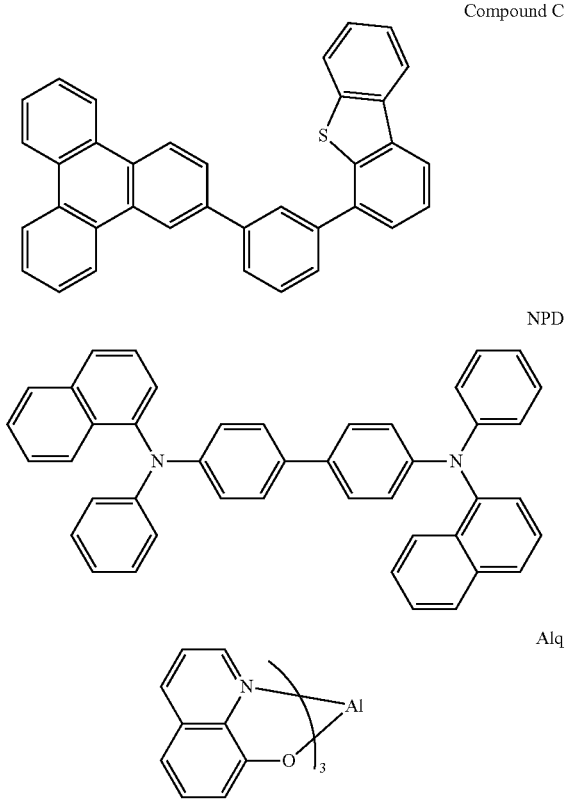

Compound C

NPD

Alq

TABLE 2

Structures of Inventive Example Devices and Comparative Example Device

| Example Devices | HIL (100 Å) | HTL (300 Å) | EML (300 Å, doping %) | BL (50 Å) | ETL (450 Å) |
|---|---|---|---|---|---|
| Comparative Example 1 | Compound B | NPD | Compound C | Compound A 10% | Compound C | Alq |
| Inventive Example 1 | Compound B | NPD | Compound C | Compound 1 10% | Compound C | Alq |
| Inventive Example 2 | Compound B | NPD | Compound C | Compound 2 10% | Compound C | Alq |
| Inventive Example 3 | Compound B | NPD | Compound C | Compound 3 10% | Compound C | Alq |
| Inventive Example 4 | Compound B | NPD | Compound C | Compound 4 10% | Compound C | Alq |
| Inventive Example 5 | Compound B | NPD | Compound C | Compound 5 15% | Compound C | Alq |

TABLE 3

| | VTE Device Results | | | | | | |
|---|---|---|---|---|---|---|---|
| | At 1000 nits | | | | | | |
| Example Devices | 1931 CIE x | 1931 CIE y | $\lambda_{max}$ (nm) | FWHM (nm) | Voltage (V) | LE (Cd/A) | EQE (%) | PE (lm/W) |
| Comparative Example 1 | 0.331 | 0.618 | 520 | 72 | 6.3 | 51.8 | 14.5 | 25.9 |
| Inventive Example 1 | 0.363 | 0.601 | 526 | 76 | 6.2 | 61.8 | 17.3 | 31.4 |
| Inventive Example 2 | 0.358 | 0.604 | 524 | 74 | 6.3 | 56.2 | 15.8 | 27.9 |
| Inventive Example 3 | 0.341 | 0.614 | 522 | 74 | 6.2 | 56.8 | 15.8 | 28.9 |
| Inventive Example 4 | 0.333 | 0.619 | 520 | 70 | 6.0 | 57.9 | 16.1 | 30.2 |
| Inventive Example 5 | 0.325 | 0.623 | 520 | 68 | 6.0 | 53.6 | 14.9 | 27.9 |

Table 3 summarizes the performance of the devices. The driving voltage (V), luminous efficiency (LE), external quantum efficiency (EQE) and power efficiency (PE) were measured at 1000 nits. As shown in Table 2 every inventive compound requires equal or slightly less voltage than the comparative example. Additionally, every inventive compound exhibited superior efficiency in virtually every category; LE, EQE and PE.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:
1. A compound having a structure selected from the group consisting of:

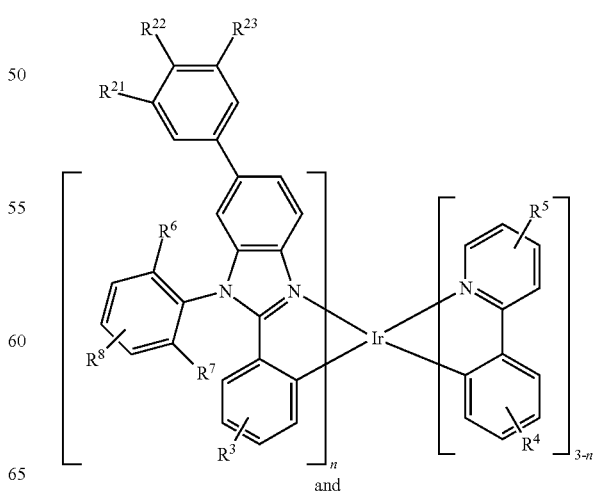

and

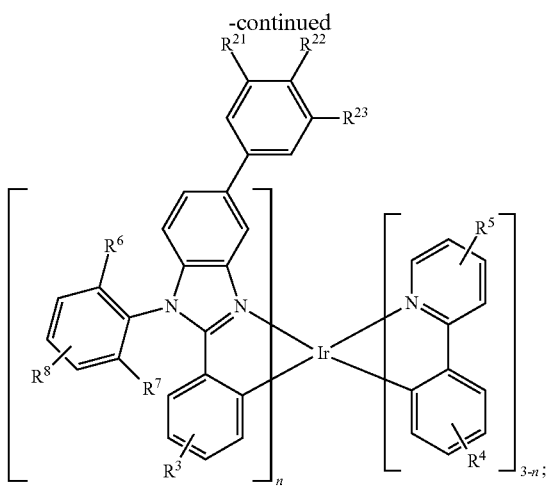

wherein R³, R⁴ and R⁵ each represent mono, di, tri, tetra substitutions or no substitution;
wherein R⁸ represents mono, di, tri substitutions or no substitution;
wherein R²¹, R²², R²³, R³, R⁴, R⁶, R⁷ and R⁸ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein each R⁵ is independently selected from the group consisting of hydrogen, deuterium, halide, alkyl, cycloalkyl, heteroalkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof; and
wherein n is 1 or 2.

2. The compound of claim 1, wherein n is 1.

3. The compound of claim 1, wherein R⁶ and R⁷ are each independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2-methylphenyl, 2,6-dimethylphenyl, 2,4,6-trimethylphenyl, 2-isopropylphenyl, 2,6-diisopropylphenyl, 2,4,6-triisopropylphenyl, 2-phenylphenyl, 2,6-diphenylphenyl, 2,4,6-triphenylphenyl, and combinations thereof;
wherein at least one of R⁶ and R⁷ is not hydrogen or deuterium.

4. The compound of claim 1, wherein at least one of R⁶ and R⁷ is selected from the group consisting of alkyl, cycloalkyl, aryl, and combinations thereof.

5. The compound of claim 1, wherein R⁶ and R⁷ are selected from the group consisting of alkyl, cycloalkyl, aryl, and combinations thereof.

6. The compound of claim 1, wherein R²¹, R²², R²³, R³, R⁴, R⁶, R⁷, and R⁸ are each independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2-methylphenyl, 2,6-dimethylphenyl, 2,4,6-trimethylphenyl, 2-isopropylphenyl, 2,6-diisopropylphenyl, 2,4,6-triisopropylphenyl, 2-phenylphenyl, 2,6-diphenylphenyl, 2,4,6-triphenylphenyl, and combinations thereof.

7. The compound of claim 1, wherein R⁸ is at least monosubstituted and at least one R⁸ is selected from the group consisting of deuterium, alkyl, cycloalkyl, aryl, and combinations thereof.

8. The compound of claim 1, wherein (a) at least one of R⁵ and R⁸ is substituted, (b) at least one of R²¹, R²², and R²³ is selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, or (c) both option (a) and option (b).

9. The compound of claim 1, wherein (a) at least one of R²¹, R²², and R²³ is selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, (b) R⁵ is mono, di, tri or tetra substituted, or (c) both.

10. The compound of claim 1, wherein R⁵ is mono, di, tri or tetra substituted.

11. The compound of claim 1, wherein R⁵ is at least monosubstituted and at least one R⁵ is selected from the group consisting of deuterium, alkyl, cycloalkyl, and combinations thereof.

12. The compound of claim 1, wherein at least one of R²¹, R²², and R²³ is selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

13. The compound of claim 1, wherein at least one of R²¹, R²², and R²³ is selected from the group consisting of deuterium, alkyl, cycloalkyl, aryl, and combinations thereof.

14. The compound of claim 1, wherein the compound of Formula I is selected from the group consisting of:

Compound 1

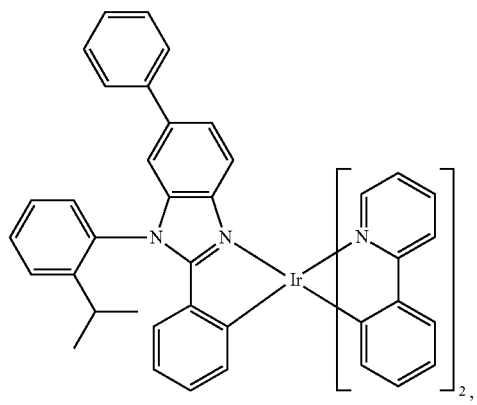

Compound 2
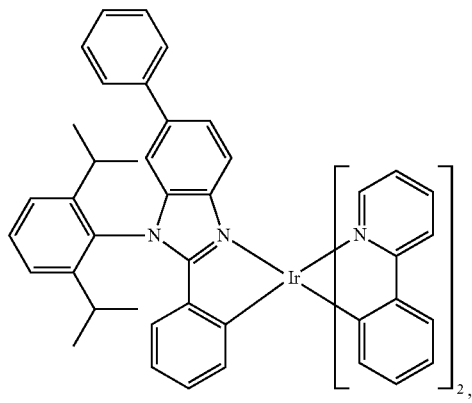
Compound 3
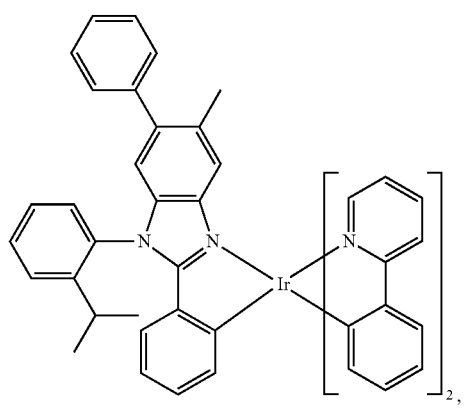
Compound 4
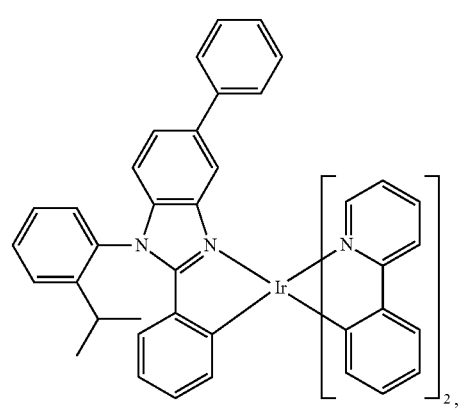
Compound 5
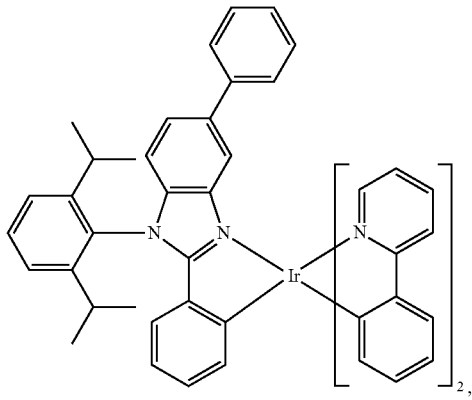
Compound 6
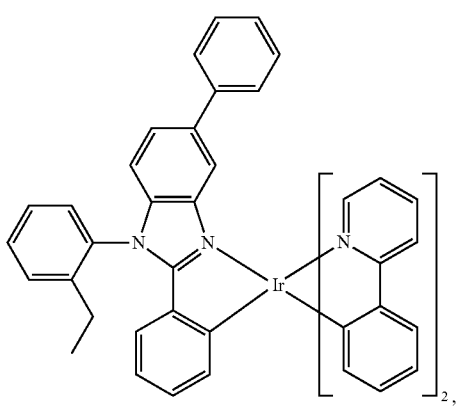
Compound 7
Compound 8
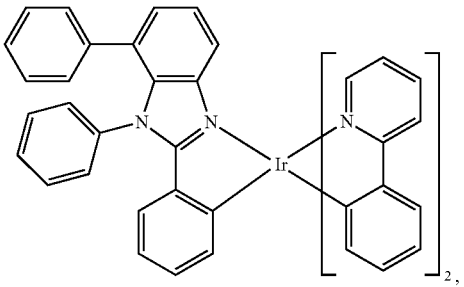

Compound 9
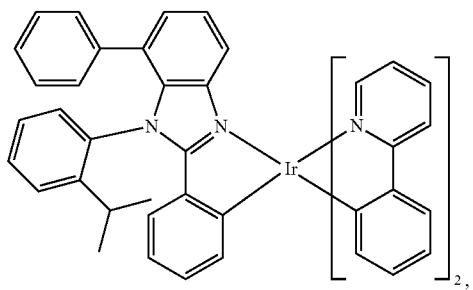
Compound 10
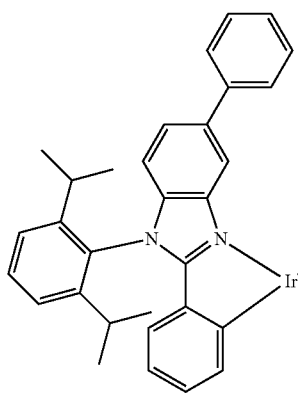
Compound 11
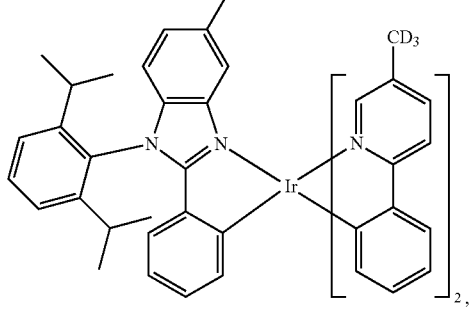
Compound 12
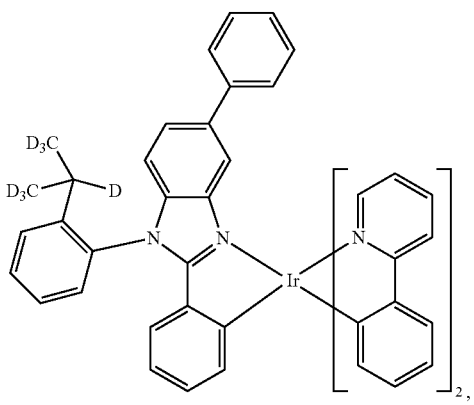
Compound 13
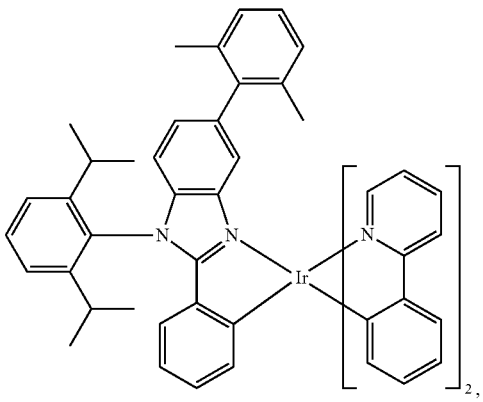
Compound 14
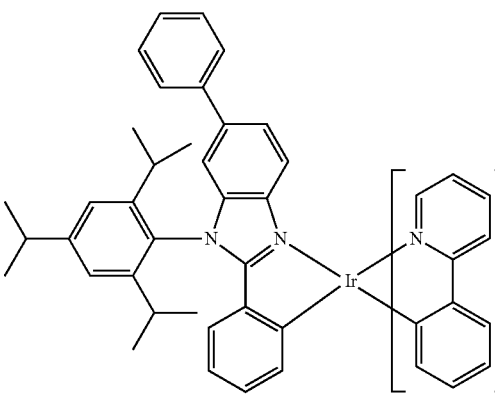
Compound 15
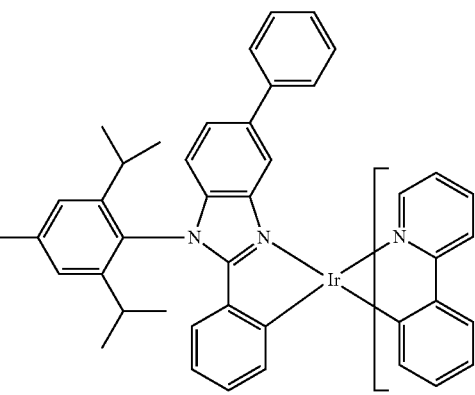

Compound 16
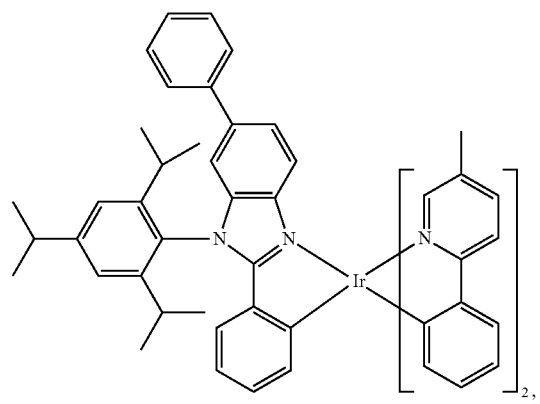
Compound 17
Compound 18
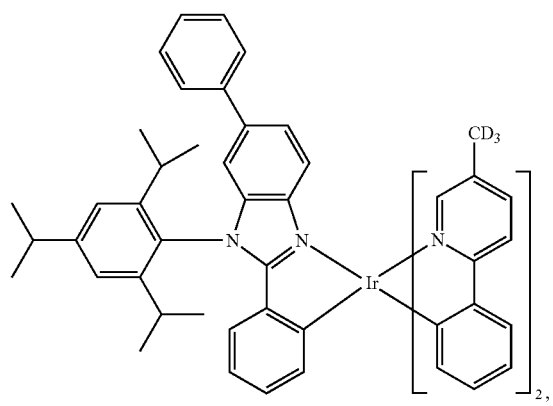
Compound 19
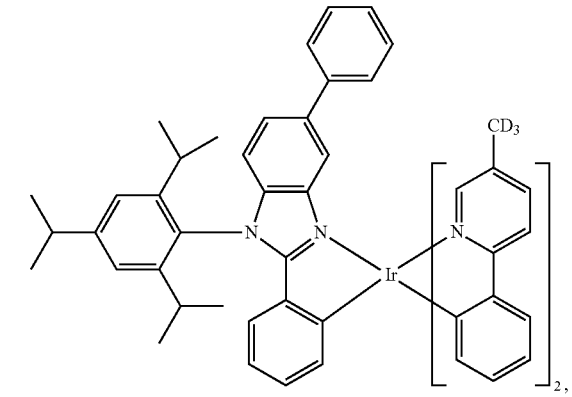
Compound 20
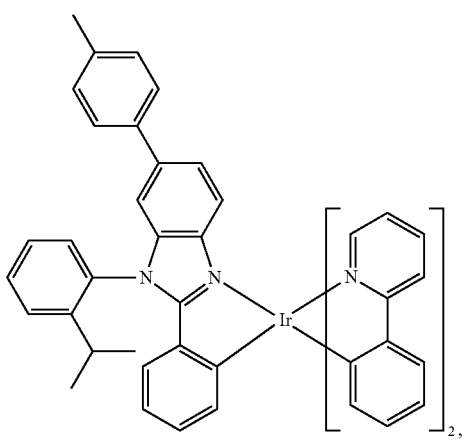
Compound 21

Compound 22
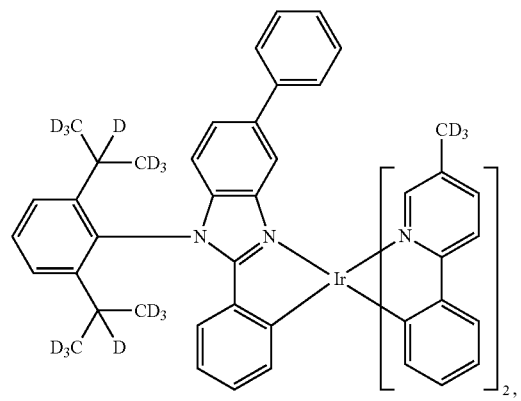
Compound 25
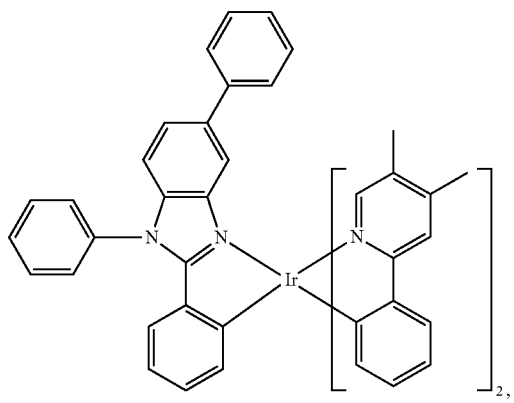
Compound 23
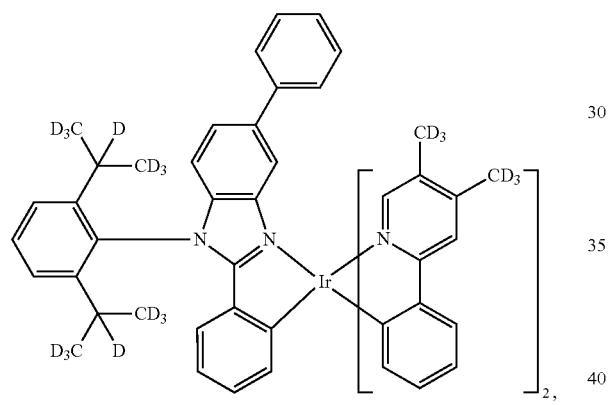
Compound 26
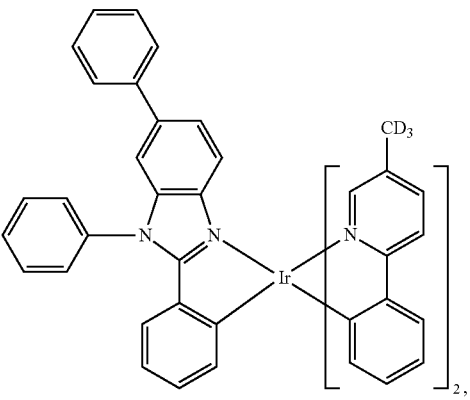
Compound 24
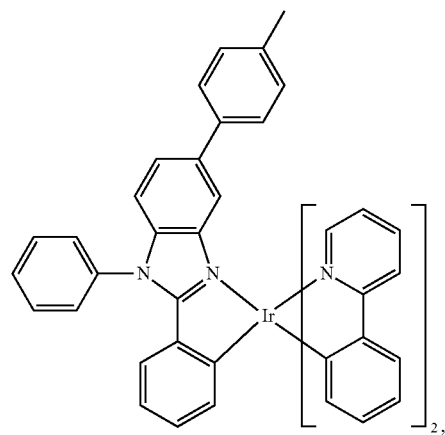
Compound 27
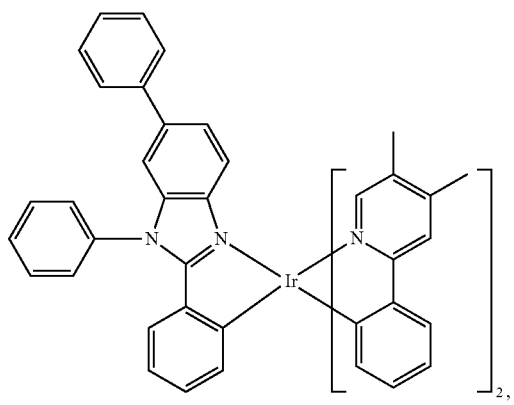

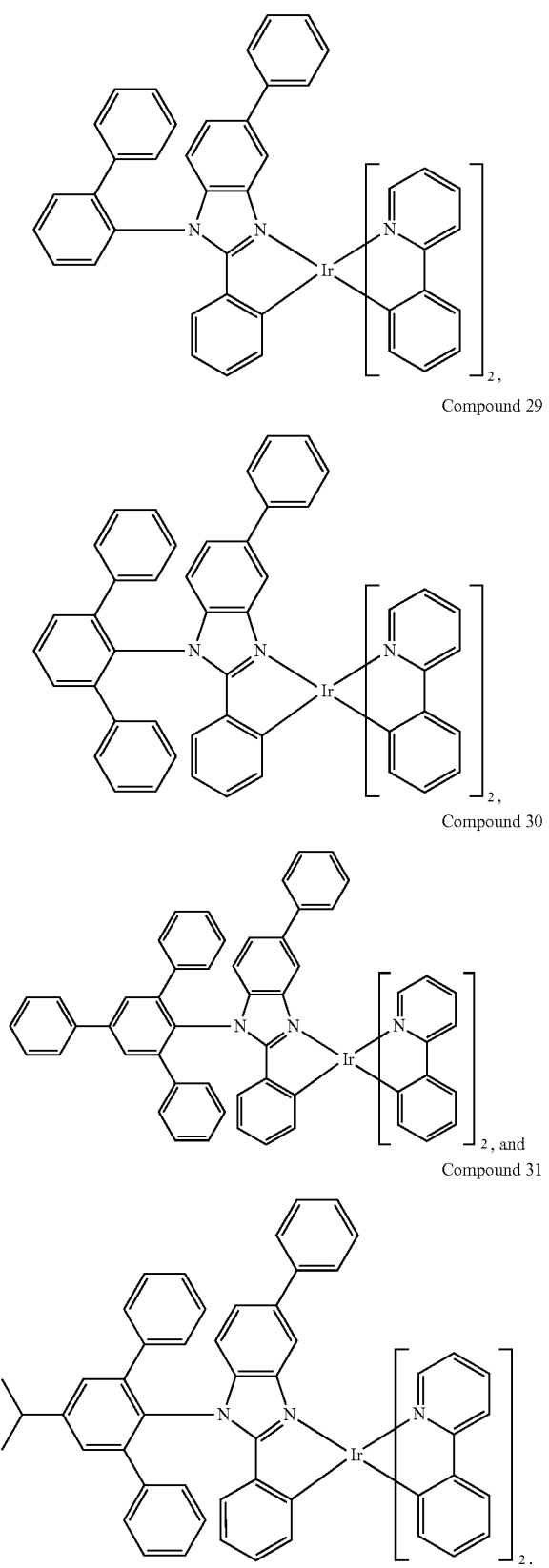

Compound 28

Compound 29

Compound 30

Compound 31

15. A first device comprising a first organic light emitting device, said first organic light emitting device comprising:
an anode;
a cathode; and
an organic layer, disposed between the anode and the cathode, comprising a compound having a structure selected from the group consisting of:

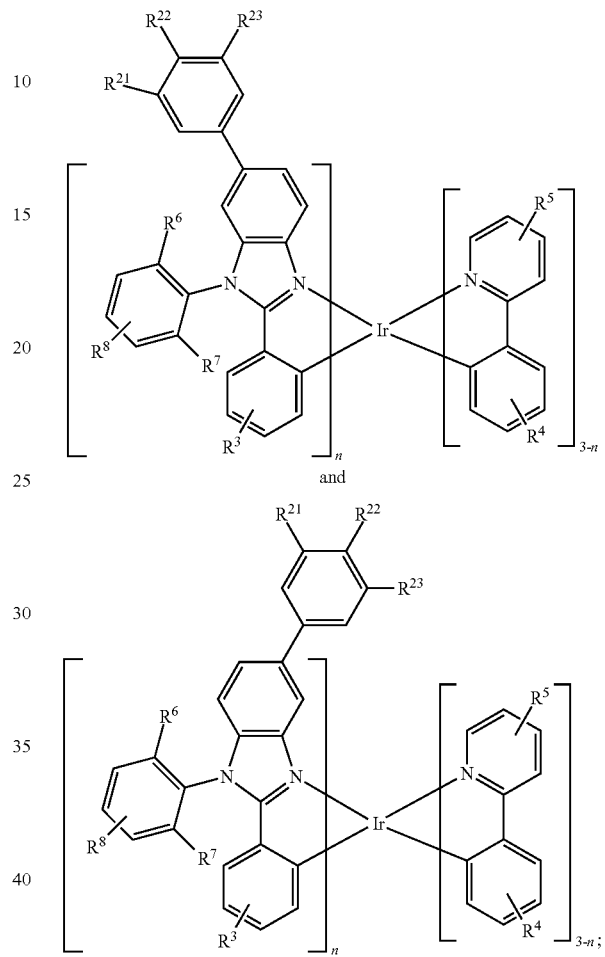

and wherein $R^3$, $R^4$ and $R^5$ each represent mono, di, tri, tetra substitutions or no substitution;
wherein $R^8$ represents mono, di, tri substitutions or no substitution;
wherein $R^{21}$, $R^{22}$, $R^{23}$, $R^3$, $R^4$, $R^6$, $R^7$ and $R^8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein each $R^5$ is independently selected from the group consisting of hydrogen, deuterium, halide, alkyl, cycloalkyl, heteroalkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof; and
wherein n is 1 or 2.

16. The first device of claim 15, wherein the first device is selected from the group consisting of a consumer product, an organic light-emitting device, and a lighting panel.

17. The first device of claim 15, wherein the organic layer is an emissive layer and the compound is an emissive dopant.

18. The first device of claim 15, wherein the organic layer is an emissive layer and the compound is a non-emissive dopant.

19. The first device of claim 15, wherein the organic layer further comprises a host.

20. The first device of claim 19, wherein the host comprises a triphenylene containing benzo-fused thiophene or benzo-fused furan;
   wherein the host is optionally substituted by an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, and $C_nH_{2n}-Ar_1$;
   wherein n is from 1 to 10; and
   wherein $Ar_1$ and $Ar_2$ are independently selected from the group consisting of benzene, biphenyl, naphthalene, triphenylene, carbazole, and heteroaromatic analogs thereof.

21. The first device of claim 19, wherein the host comprises a compound selected from the group consisting of: carbazole, dibenzothiophene, dibenzofuran, dibenzoselenophene, azacarbazole, aza-dibenzothiophene, aza-dibenzofuran, and aza-dibenzoselenophene.

22. The first device of claim 19, wherein the host is selected from the group consisting of:

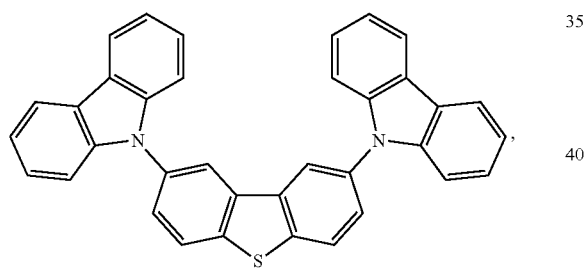

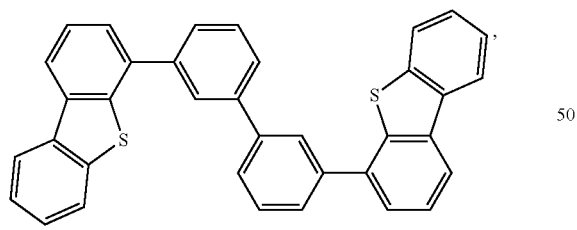

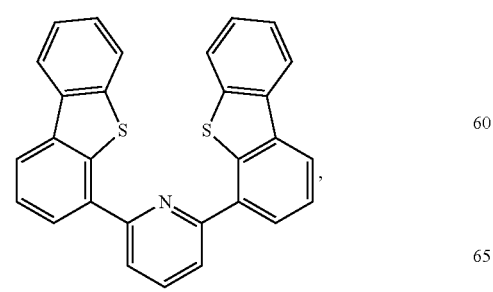

-continued

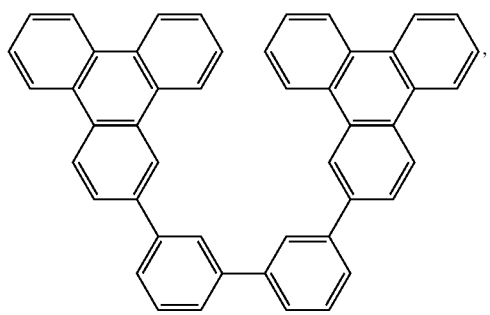

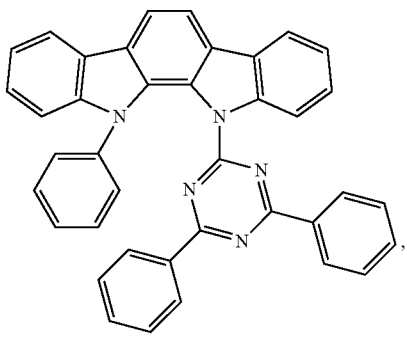

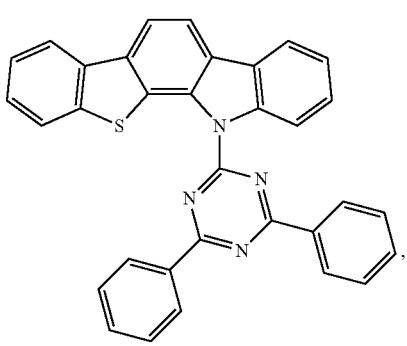

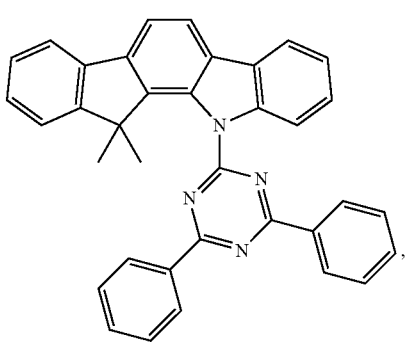

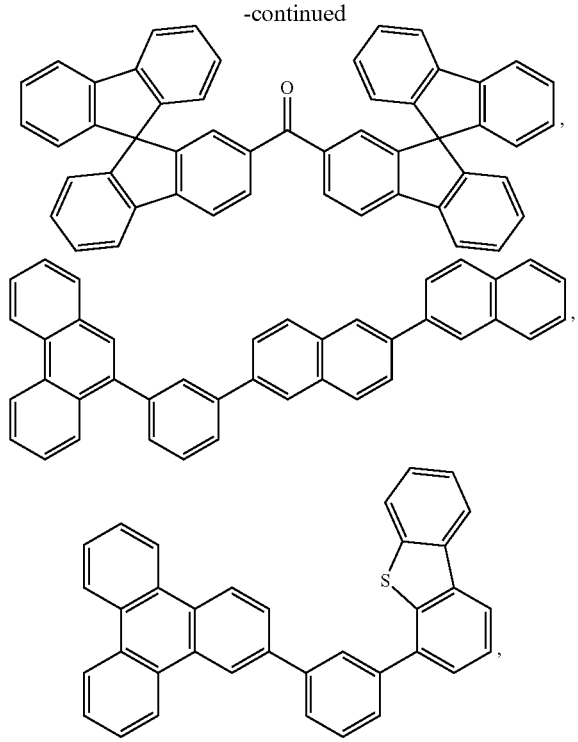
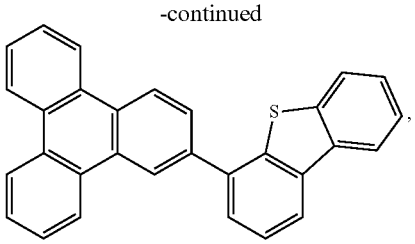

and combinations thereof.

23. The first device of claim 19, wherein the host comprises a metal complex.

24. The compound of claim 1, wherein $R^{21}$, $R^{22}$, and $R^{23}$ are selected from the group consisting of hydrogen and alkyl.

25. The compound of claim 24, wherein at least one of $R^{21}$, $R^{22}$, and $R^{23}$ is alkyl.

26. The compound of claim 1, wherein $R^{21}$, $R^{22}$, and $R^{23}$ are hydrogen.

27. The compound of claim 1, wherein $R^6$ is hydrogen, and $R^7$ is selected from the group consisting of alkyl, cycloalkyl, aryl, and combinations thereof.

28. The compound of claim 1, wherein $R^6$ and $R^7$ are selected from the group consisting of hydrogen and isopropyl, and at least one of $R^6$ and $R^7$ is isopropyl.

* * * * *

UNITED STATES PATENT AND TRADEMARK OFFICE
CERTIFICATE OF CORRECTION

PATENT NO. : 10,400,163 B2
APPLICATION NO. : 13/762612
DATED : September 3, 2019
INVENTOR(S) : Scott Beers et al.

Page 1 of 2

It is certified that error appears in the above-identified patent and that said Letters Patent is hereby corrected as shown below:

In the Claims

In Claim 14, Column 139, Lines 25-45, please delete compound 3 shown below:

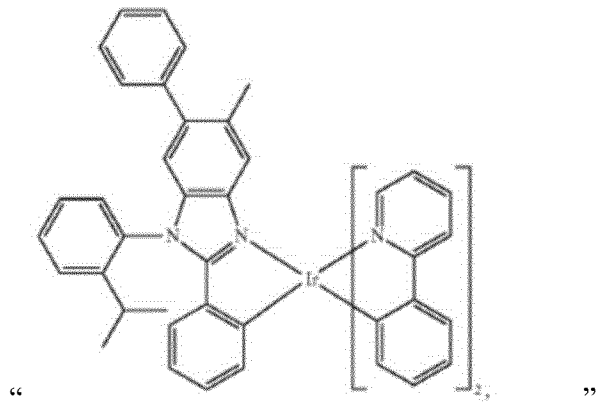

In Claim 14, Column 140, Lines 54-67, please delete compound 8 shown below:

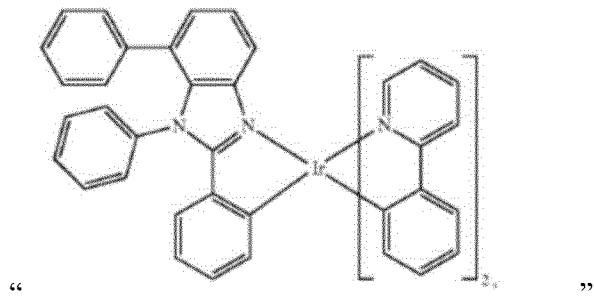

Signed and Sealed this
Eighteenth Day of February, 2020

Andrei Iancu
*Director of the United States Patent and Trademark Office*

CERTIFICATE OF CORRECTION (continued)
U.S. Pat. No. 10,400,163 B2

In Claim 14, Column 141, Lines 1-14, please delete compound 9 shown below:

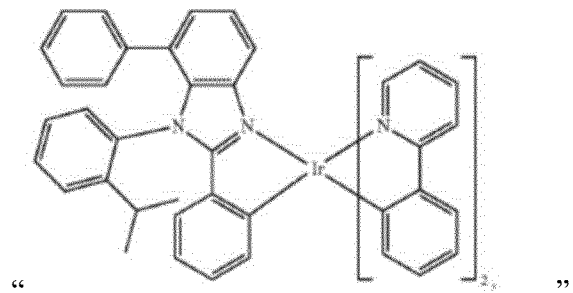

" "

In Claim 14, Column 142, Lines 1-14, please delete compound 13 shown below:

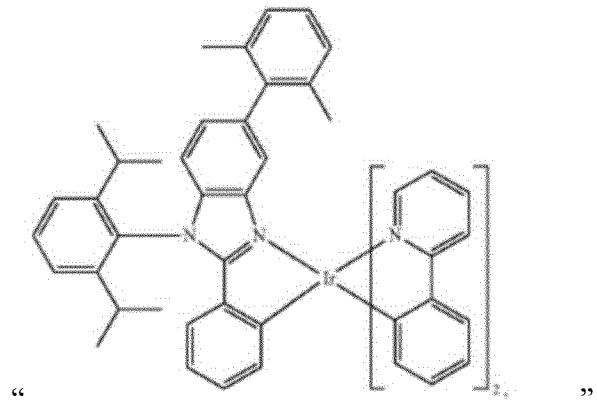

" "